(12) United States Patent
Hara et al.

(10) Patent No.: US 6,706,745 B1
(45) Date of Patent: Mar. 16, 2004

(54) BIPHENYLAMIDINE DERIVATIVES

(75) Inventors: Takayuki Hara, Hino (JP); Tomohisa Nakada, Hino (JP); Yasunobu Takano, Hino (JP); Satoshi Sugiura, Hino (JP); Takaharu Tsutsumi, Hino (JP); Yoshiharu Takazawa, Hino (JP); Reiko Takarada, Hino (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 09/554,799

(22) PCT Filed: Nov. 19, 1998

(86) PCT No.: PCT/JP98/05209

§ 371 (c)(1),
(2), (4) Date: May 18, 2000

(87) PCT Pub. No.: WO99/26918

PCT Pub. Date: Jun. 3, 1999

(30) Foreign Application Priority Data

Nov. 20, 1997 (JP) ............................................. 9/319698
May 11, 1998 (JP) ........................................... 10/127498

(51) Int. Cl.$^7$ .................. A61K 31/425; A61P 7/02; C07D 237/02; C07D 421/00; C07D 231/04
(52) U.S. Cl. ............ 514/369; 514/252.01; 514/255.02; 514/269; 514/403; 514/408; 514/637; 544/239; 544/298; 544/397; 544/398; 546/192; 546/216; 548/356.1; 548/400
(58) Field of Search .................. 514/637, 252.01, 514/255.02, 269, 369, 403, 408; 544/239, 298, 397, 398; 546/216, 192; 548/356.1, 400; 564/247

(56) References Cited

FOREIGN PATENT DOCUMENTS

| EP | 0496378 A | 7/1992 | |
|---|---|---|---|
| EP | 574808 | * 12/1993 | |
| EP | 1043311 A | 10/2000 | |
| JP | 4-334351 | 11/1992 | .......... C07C/211/44 |
| JP | 6-50977 | 2/1994 | .......... G01N/33/86 |
| JP | 10-1467 | 1/1998 | .......... C07C/257/18 |
| JP | 1001467 | 1/1998 | |

OTHER PUBLICATIONS

Translation of Japanese Patent Publication No. 10–1467, paragraphs [0001]–[0006] of Specification.

* cited by examiner

Primary Examiner—Richard L. Raymond
Assistant Examiner—Tamthom N. Truong
(74) Attorney, Agent, or Firm—Sughrue Mion, PLLC

(57) ABSTRACT

The present invention relates to a biphenylamidine derivative of the general formula (1):

$$HN=C(NH_2)-\text{Ar}-\text{Ar}'-(CH_2)_m-X-(CH_2)_n-Y \quad (1)$$

or a pharmaceutically acceptable salt thereof, which is a novel compound functioning as a clinically applicable FXa inhibitor.

9 Claims, No Drawings

BIPHENYLAMIDINE DERIVATIVES

TECHNICAL FIELD

The present invention relates to novel, and selective, activated blood coagulation factor Xa (hereafter, "FXa") inhibitors of the general formula (I).

Background Art

A therapy for anticoagulation plays an important part in the medical treatment and prophylaxis of thromboembolisms such as myocardial infarction, cerebral thrombosis, thrombosis of peripheral arteries, and thrombosis of deep veins.

In particular, for the prophylaxis of chronic thrombosis, harmless and appropriate oral anticoagulants which can be administrated over a long period of time are desired. However, to date, warfarin potassium agent which are difficult to control the extent of the anti-coagulation are the only above-mentioned anticoagulants, and thus a need for anticoagulants which are easy to use is left.

Though antithrombin agents have been developed as anticoagulants in the past, it is known that these agents, for example hirudin, have a risk of a tendency toward bleeding as a side effect. The fact that inhibition of FXa, located upstream of thrombin in the blood coagulation cascade is systematically more effective than inhibition of thrombin and that the FXa inhibitors do not cause the above significant side effect and is clinically preferable, has begun to be understood.

Biphenylamidine compounds, which exhibit FXa inhibition activity, were disclosed in The 17th Symposium on Medicinal Chemistry, The 6th Annual Meeting of Division of Medicinal Chemistry, Abstracts, 184–185, 1997. However, compounds of the present invention are novel compounds which differ distinctly in the use of a heteroatom in a linkage between the biphenylamidine structure which may interact with an S1 pocket and the cyclic structure which may interact with an aryl binding site, and in the presence of a substituent such as a carboxyl group on a linker benzene ring.

Further, Japanese Unexamined Patent Publication (Kokai) No. 4-264068 discloses biphenylamidine derivatives as cyclic imino-derivatives. However, compounds of the present invention differ in the presence of a bond, through a heteroatom, at a benzyl-position.

Therefore, an object of the present invention is to provide a novel compound which may be a FXa inhibitor having a clinical applicability.

Disclosure of the Invention

The inventors have made every effort to achieve the above purpose and, as a result, devised the following 1–10 inventions.

1. A biphenylamidine derivative of general formula (1):

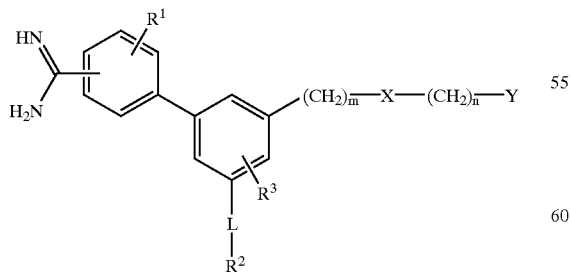

(1)

wherein $R^1$ is a hydrogen atom, a fluorine atom, a chlorine atom, a bromine atom; a hydroxyl group, an amino group, a nitro group, a $C_{1-8}$ alkyl group, or a $C_{1-8}$ alkoxy group;

L is a direct bond or a $C_{1-4}$ alkylene group;

$R^2$ is a fluorine atom; a chlorine atom; a bromine atom; a hydroxyl group; an amino group; a $C_{1-8}$ alkoxy group; a carboxyl group; a $C_{1-8}$ alkoxycarbonyl group; an aryloxycarbonyl group; an aralkoxycarbonyl group; a carbamoyl group wherein a nitrogen atom constituting the carbamoyl may be substituted with a mono- or di-$C_{1-8}$ alkyl group or may be a nitrogen atom in an amino acid; a $C_{1-8}$ alkylcarbonyl group; a $C_{1-8}$ alkylsulfenyl group; a $C_{1-8}$ alkylsulfinyl group; a $C_{1-8}$ alkylsulfonyl group; a mono- or di-$C_{1-8}$ alkylamino group; a mono- or di-$C_{1-8}$ alkylaminosulfonyl group; a sulfo group; a phosphono group; a bis(hydroxycarbonyl)methyl group; a bis(alkoxycarbonyl)methyl group; or a 5-tetrazolyl group;

$R^3$ is a hydrogen atom, a fluorine atom, a chlorine atom, a bromine atom, a hydroxyl group, an amino group, a nitro group, a $C_{1-8}$ alkyl group, a $C_{1-8}$ alkoxy group, a carboxyl group, or a $C_{1-8}$ alkoxycarbonyl group;

X is any of the formulae:
—O—, —S—, —SO—, —SO$_2$—, —NH—CO—NH—, —N(R$^4$)—, —CO—N(R$^5$)—, —N(R$^5$)—CO—, —N(R$^5$)—SO$_2$—, —SO$_2$—N(R$^5$)—, wherein $R^4$ is a hydrogen atom, a $C_{1-10}$ alkyl group, a $C_{1-10}$ alkylcarbonyl group, a $C_{1-10}$ alkylsulfonyl group, a $C_{3-8}$ cycloalkyl group, or an aryl group, $R^5$ is a hydrogen atom, a $C_{1-10}$ alkyl group, a $C_{3-8}$ cycloalkyl group, or an aryl group, wherein an alkyl group in the $R^4$ and $R^5$ may be substituted with an aryl group, a hydroxyl group, an amino group, a fluorine atom, a chlorine atom, a bromine atom, a $C_{1-8}$ alkoxy group, a carboxyl group, a $C_{1-8}$ alkoxycarbonyl group, an aryloxycarbonyl group, an aralkoxycarbonyl group, a carbamoyl group, or a 5-tetrazolyl group;

Y is a $C_{4-8}$ cycloalkyl group wherein a methylene group in the $C_{4-8}$ cycloalkyl may be replaced with a carbonyl group, or may be substituted with a fluorine atom, a chlorine atom, a bromine atom, a hydroxyl group, an amino group, a $C_{1-8}$ alkyl group, a $C_{1-8}$ alkoxy group, a carbamoyl group, a $C_{1-8}$ alkoxycarbonyl-group, a carboxyl group, an aminoalkyl group, a mono- or di-alkylamino group, or a mono- or di-alkylaminoalkyl group; or the following 5–8-membered ring of the formulae I-1 or I-2:

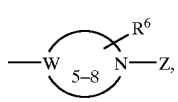

[I-1]

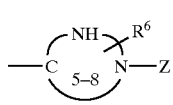

[I-2]

wherein, in the formulae I-1 and I-2, in each cyclic system, the methylene group may be replaced with a carbonyl group, and the cycle may have unsaturated bonds, $R^6$ is a hydrogen atom, a fluorine atom, a chlorine atom, a bromine atom, a hydroxyl group, an amino group, a nitro group, a $C_{1-8}$ alkyl group, or a $C_{1-8}$ alkoxy group, W is C—H, or a nitrogen atom, with the proviso that W is not a nitrogen atom when the cycle is 5-membered ring, Z is a hydrogen atom; a $C_{1-10}$ alkyl group wherein the alkyl group may be substituted with a hydroxyl group except when Z is a $C_1$ alkyl, an amino group, a $C_{1-8}$ alkoxy group except when Z is a $C_1$ alkyl, a carboxyl group, a $C_{1-8}$ alkoxycarbonyl group, an aryloxycarbonyl group or an aralkoxycarbonyl group; a $C_{1-8}$ alkylcarbonyl group; an arylcarbonyl group; an aralkylcarbonyl group; an amidino group; or the following group of the formula I-3:

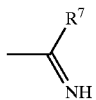

[I-3]

wherein, in the formula I-3,
$R^7$ is a $C_{1-8}$ alkyl group wherein the alkyl group may be substituted with a hydroxyl group or a $C_{1-8}$ alkoxy group; an aralkyl group; or an aryl group;
m is an integer of 1–3;
n is an integer of 0–3, with the proviso that W is not a nitrogen atom when n is 0–1; or a pharmaceutically acceptable salt thereof.

2. A biphenylamidine derivative wherein, in said formula (1),
$R^1$ is a hydrogen atom, a fluorine atom, a chlorine atom, a bromine atom, a hydroxyl group, an amino group, a $C_{1-4}$ alkyl group, or a $C_{1-4}$ alkoxy group;
L is a direct bond or a $C_{1-4}$ alkylene group;
$R^2$ is a fluorine atom; a chlorine atom; a bromine atom; a hydroxyl group; an amino group; a $C_{1-8}$ alkoxy group; a carboxyl group; a $C_{1-8}$ alkoxycarbonyl group; an aryloxycarbonyl group; an aralkoxycarbonyl group; a carbamoyl group wherein a nitrogen atom in the carbamoyl group may be substituted with a mono- or di-$C_{1-8}$ alkyl group or may be a nitrogen atom in an amino acid; a $C_{1-8}$ alkylcarbonyl group; a $C_{1-8}$ alkylsulfenyl group; a $C_{1-8}$ alkylsulfinyl group; a $C_{1-8}$ alkylsulfonyl group; a mono- or di-$C_{1-8}$ alkylamino group; a mono- or di-$C_{1-8}$ alkylaminosulfonyl group; a sulfo group; a phosphono group; a bis(hydroxycarbonyl)methyl group; a bis(alkoxycarbonyl)methyl group; or a 5-tetrazolyl group;
$R^3$ is a hydrogen atom;
X is any of the formulae:
—O—; —S—, —N($R^4$)—, —CO—N($R^5$)—, —N($R^5$)—CO—, —N($R^5$)SO$_2$—, or —SO$_2$—N($R^5$)—;
wherein
$R^4$ is a hydrogen atom, a $C_{1-10}$ alkyl group, a $C_{1-10}$ alkylcarbonyl group, or a $C_{1-10}$ alkylsulfonyl group,
$R^5$ is a hydrogen atom, or a $C_{1-10}$ alkyl group,
wherein an alkyl group in the $R^4$ and $R^5$ may be substituted with an aryl group, a hydroxy group, an amino group, a fluorine atom, a chlorine atom, a bromine atom, a $C_{1-8}$ alkoxy group, a carboxyl group, a $C_{1-8}$ alkoxycarbonyl group, an aryloxycarbonyl group, an aralkoxycarbonyl group, a carbamoyl group, or a 5-tetrazoyl group;
Y is a $C_{4-8}$ cycloalkyl group wherein a methylene group constituting the $C_{4-8}$ cycloalkyl may be replaced with a carbonyl group, or may be substituted with a fluorine atom, a chlorine atom, a bromine atom, a hydroxyl group, an amino group, a $C_{1-8}$ alkyl group, a $C_{1-8}$ alkoxy group, a carbamoyl group, a $C_{1-8}$ alkoxycarbonyl group, a carboxyl group, an aminoalkyl group, a mono- or di-alkylamino group, or a mono- or di-alkylaminoalkyl group; or the following 5–8-membered ring of the formula II-1:

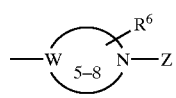

[II-1]

wherein, in formulae II-1,
in the cyclic system, the methylene may be replaced with a carbonyl group,
$R^6$ is a hydrogen atom, a fluorine atom, a chlorine atom, a bromine atom, a hydroxyl group, an amino group, a $C_{1-4}$ alkyl group, or a $C_{1-4}$ alkoxy group;
W is C—H, or a nitrogen atom, with the proviso that W is not a nitrogen atom when the cycle is 5-membered ring,
Z is a hydrogen atom; a $C_{1-10}$ alkyl group wherein the alkyl group may be substituted with a hydroxyl group except when Z is a $C_1$ alkyl, an amino group, a $C_{1-8}$ alkoxy group except when Z is a $C_{1-8}$ alkyl, a carboxyl group, a $C_{1-8}$ alkoxycarbonyl group, an aryloxycarbonyl group, or an aralkoxycarbonyl group; a $C_{1-8}$ alkylcarbonyl group; an arylcarbonyl group; an aralkylcarbonyl group; an amidino group; or the following group of the formula II-2:

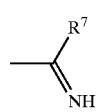

[II-2]

wherein, in formula II-2,
$R^7$ is a $C_{1-8}$ alkyl group wherein the alkyl group may be substituted with a hydroxyl group or a $C_{1-4}$ alkoxy group; an aralkyl group; or an aryl group;
m is an integer of 1–3;
n is an integer of 0–3, with the proviso that W is not a nitrogen atom when n is 0–1; or a pharmaceutically acceptable salt thereof.

3. A biphenylamidine derivative of general formula (2):

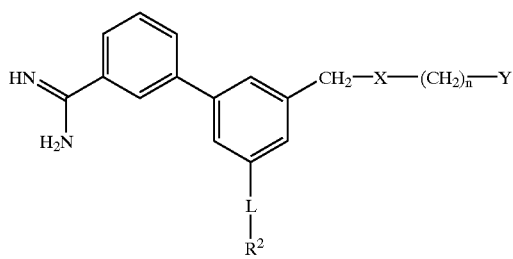

(2)

wherein
L is a bond or a $C_{1-4}$ alkylene group;
$R^2$ is a carboxyl group; a $C_{1-4}$ alkoxycarbonyl group; an aralkoxycarbonyl group; a carbamoyl group wherein a nitrogen atom constituting the carbamoyl group may be substituted with a mono- or di-$C_{1-4}$ alkyl group or may be a nitrogen atom in an amino acid; or a $C_{1-4}$ alkyl-carbonyl group;

X is —O—, —N($R^4$)—, or —NH—CO—, wherein $R^4$ is a hydrogen atom, a $C_{1-10}$ alkyl group, a $C_{1-10}$ alkylcarbonyl group or a $C_{1-10}$ alkylsulfonyl group, the alkyl group being optionally substituted with a hydroxyl group, an amino group, a fluorine group, a carboxyl group or a $C_{1-8}$ alkoxycarbonyl group;

Y is a $C_{5-6}$ cycloalkyl group wherein a methylene group constituting the $C_{5-6}$ cycloalkyl group may be substituted with a carbamonyl group, a $C_{1-4}$ alkoxy group or a carboxyl group; or the following 5–6-membered ring of the formula III-1:

[III-1]

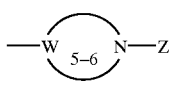

wherein, in formula III-1,

W is C—H, or a nitrogen atom, with the proviso that W is not a nitrogen atom when the cycle is 5-membered ring, Z is a hydrogen atom; a $C_{1-4}$ alkyl group wherein the alkyl group may be substituted with a hydroxyl group except when Z is a $C_1$ alkyl, an amino group, a carboxyl group or a $C_{1-4}$ alkoxycarbonyl group; a $C_{1-4}$ alkylcarbonyl group; an amidino group; or the following group of the formula III-2:

[III-2]

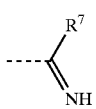

wherein, in formula III-2, $R^7$ is a $C_{1-4}$ alkyl group wherein the alkyl group may be substituted with a hydroxyl group;

n is an integer of 0–2; with the proviso that W is not a nitrogen atom when n is 0–1; or a pharmaceutically acceptable salt thereof.

4. A biphenylamidine derivative wherein; in said formula (2),

X is —O—, or —N($R^4$)—, wherein $R^4$ is a hydrogen atom, a $C_{1-10}$ alkyl group, a $C_{1-10}$ alkylcarbonyl group or a $C_{1-10}$ alkylsulfonyl group, wherein the alkyl being optionally substituted with a hydroxyl group, an amino group, a fluorine atom, a carboxyl group or a $C_{1-8}$ alkoxycarbonyl group; or a pharmaceutically acceptable salt thereof.

5. A biphenylamidine derivative wherein, in said formula (2),

X is —NH—CO—, or a pharmaceutically acceptable salt thereof.

6. A biphenylamidine derivative wherein, in general formula (2),

L is a bond;

$R^2$ is a carboxyl group or a methoxycarbonyl group;

X is —O—, or —N($R^4$)—, wherein $R^4$ is a hydrogen atom, a methyl group or a 2-hydroxyethyl group;

Y is any of the formulae:

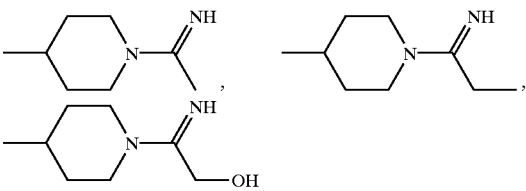

n is 1;

or a pharmaceutically acceptable salt thereof.

7. A prodrug which generates a biphenylamidine derivative or a pharmaceutically acceptable salt thereof according to any one of said 1–6, in vivo.

8. A blood coagulation inhibitor comprising at least a biphenylamidine derivative or a pharmaceutically acceptable salt thereof according to any one of said 1–7, and a pharmaceutically acceptable carrier.

9. A prophylactic agent for thrombosis or embolus, comprising at least a biphenylamidine derivative or a pharmaceutically acceptable salt thereof according to any one of said 1–7, and a pharmaceutically acceptable carrier.

10. A therapeutic agent for thrombosis or embolus, comprising at least a biphenylamidine derivative or a pharmaceutically acceptable salt thereof according to any one of said 1–7, and a pharmaceutically acceptable carrier.

Best Mode for Carrying Out the Invention

The present invention is detailed in the following description.

In the definition regarding the substituents in a compound of formula (1) of the present invention:

The term "$C_{1-8}$ alkyl" means a branched or straight carbon chain having 1 to 8 carbons, and includes for example, methyl, ethyl, propyl, isopropyl, butyl, isobutyl, tert-butyl, pentyl, neo-pentyl, isopentyl, 1,2-dimethylpropyl, hexyl, isohexyl, 1,1-dimethylbutyl, 2,2-dimethylbutyl, 1-ethylbutyl, 2-ethylbutyl, isoheptyl, octyl, or isooctyl, etc. Among them, one having 1 to 4 carbons is preferable and methyl or ethyl is particularly preferable.

The term "$C_{1-8}$ alkoxy" means an alkoxy group having 1 to 8 carbons, and includes for example, methoxy, ethoxy, propoxy, isopropoxy, butoxy, isobutoxy, sec-butoxy, tert-butoxy, pentyloxy, neo-pentyloxy, tert-pentyloxy, 2-methylbutoxy, hexyloxy, isohexyloxy, heptyloxy, isoheptyloxy, octyloxy, or isooctyloxy, etc. Among them, one having 1 to 4 carbons is preferable and methoxy or ethoxy is particularly preferable.

The term "$C_{1-4}$ alkylene" means a straight alkylene having 1 to 4 carbons, and includes methylene, ethylene, propylene, or butylene.

The term "$C_{1-8}$ alkoxycarbonyl" means methoxycarbonyl, ethoxycarbbnyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl, hexyloxycarbonyl, heptyloxycarbonyl, or octyloxycarbonyl, etc.; preferably, it is methoxycarbonyl, ethoxycarbonyl or tert-butoxycarbonyl; and more preferably, it is methoxycarbonyl.

The term "aryloxycarbonyl" means phenoxycarbonyl, naphthyloxycarbonyl, 4-methylphenoxycarbonyl, 3-chlorophenoxycarbonyl, or 4-methoxyphenoxycarbonyl, etc.; and preferably, it is phenbxycarbonyl.

The term "aralkoxycarbonyl" means benzyloxycarbonyl, 4-methoxybenzyloxycarbonyl, or 3-trifluoromethylbenzyloxycarbonyl, etc.; and preferably, it is benzyloxycarbonyl.

The term "amino acid" means a natural or non-natural commercially available amino acid; preferably, is glycine, alanine or β-alanine; and more preferably, it is glycine.

The term "$C_{1-8}$ alkylcarbonyl" means a carbonyl group having a straight or branched carbon chain having 1 to 8 carbons, and includes for example, hormyl, acetyl, propionyl, butyryl, isobutyryl, valeryl; isovaleryl, pivaloyl, hexanoyl, heptanoyl, or octanoyl, etc.; preferably, it is the one having 1 to 4 carbons; and more preferably, it is acetyl or propionyl.

The term "$C_{1-6}$ alkylsulfenyl" means an alkylsulfenyl group having 1 to 8 carbons, and includes for example, methylthio, ethylthio, butylthio, isobutythio, pentylthio, hexylthio, heptylthio, or octylthio, etc., and preferably, it is methylthio.

The term "$C_{1-8}$ alkylsulfinyl" means an alkylsulfinyl group having 1 to 8 carbons, and includes for example, methylsulfinyl, ethylsulfinyl, butylsulfinyl, hexylsulfinyl, or octylsulfinyl, etc., and preferably, it is methylsulfinyl.

The term "$C_{1-8}$ alkylsulfonyl" means an alkylsulfonyl group having 1 to 8 carbons, and includes for example, methylsulfonyl, ethylsulfonyl, butylsulfonyl, hexylsulfonyl, or octylsulfonyl, etc., and preferably, it is methylsulfonyl.

The term "mono- or di-$C_{1-8}$ alkylamino" means methylamino, dimethylamino, ethylamino, propylamino, diethylamino, isopropylamino, diisopropylamino, dibutylamino, butylamino, isobutylamino, sec-butylamino, tert-butylamino, pentylamino, hexylamino, heptylamino, or octylamino, etc.; preferably, it is methylamino, dimethylamino, ethylamino, diethylamino or propylamino; and more preferably, it is methylamino or dimethylamino.

The term "mono- or di-$C_{1-8}$ alkylaminosulfonyl" means for example methylaminosulfonyl, dimethylaminosulfonyl, ethylaminosulfonyl, propylaminosulfonyl, diethylaminosulfonyl, isopropylamninosulfonyl, diisopropylaminosulfonyl, dibutylaminosulfonyl, butylaminosulfonyl, isobutylaminosulfonyl, sec-butylaminosulfonyl, tert-butylaminosulfonyl, pentylaminosulfonyl, hexylaminosulfonyl, heptylaminosulfonyl, or octylaminosulfonyl, etc.; preferably, it is methylaminosulfonyl, dimethylaminosulfonyl, ethylaminosulfonyl, diethylaminosulfonyl or propylaminosulfonyl; and more preferably, it is methylaminosulfonyl or dimethylaminosulfonyl.

The term "bis(alkoxycarbonyl)methyl" means, particularly, bis(methoxycarbonyl)methyl, or bis(ethoxycarbonyl)methyl, etc.; preferably it is bis(methoxycarbonyl)methyl.

The term "$C_{1-10}$ alkyl" means a straight or branched carbon chain having 1 to 10 carbons, and includes for example, methyl, ethyl, propyl, isopropyl, butyl, isobutyl, tert-butyl, pentyl, neo-pentyl, isopentyl, 1,2-dimethylpropyl, hexyl, isohexyl, 1,1-dimethylbutyl, 2,2-dimethylbutyl, 1-ethylbutyl, 2-ethylbutyl, heptyl, isoheptyl, 1-methylhexyl, 2-methylhexyl, octyl, 2-ethylhexyl, nonyl, decyl, or 1-methylnonyl, etc. Among them, the one having 1 to 4 carbons is preferable, and methyl or ethyl is particularly preferable.

The term "$C_{1-10}$ alkylcarbonyl" means-a carbonyl group having a straight or branched carbon chain having 1 to 10 carbons, and includes for example, hormyl, acetyl, propionyl, butyryl, isobutyryl, valeryl, isovaleryl, pivaloyl, hexanoyl, heptanoyl, octanoyl, nonanoyl, or decanoyl, etc.; preferably, it is one having 1 to 4 carbons; and more preferably, it is acetyl or propionyl.

The term "$C_{1-10}$ alkylsulfonyl" means an alkylsulfonyl group having 1 to 10 carbons, and includes for example, methylsulfonyl, ethylsulfonyl, propylsulfonyl, isopropylsulfonyl, butylsulfonyl, isobutylsulfonyl, pentylsulfonyl, isopentylsulfonyl, neopentylsulfonyl, hexylsulfonyl, heptylsulfonyl, octylsulfonyl, nonylsulfonyl, or decylsulfonyl, etc.; preferably, it is one having 1 to 4 carbons; and more preferably, it is methylsulf onyl or ethylsulfonyl.

The term "$C_{3-8}$ cycloalkyl" means a cycloalkyl group having 3 to 8 carbons, and includes particularly, cyclopropyl, cyclobutyl, cyclopentyl, cyclohexyl, cycloheptyl, or cyclooctyl; and is preferably cyclopropyl.

The term "aryl" means particularly a carbocyclic aryl group such as phenyl or naphthyl, or heteroaryi such as pyridyl or furyl, and preferably, it is phenyl.

The term "$C_{4-8}$ cycloalkyl" means a cycloalkyl group having 4 to 8 carbons, and includes particularly, cyclobutyl, cyclopentyl, cyclohexyl, cycloheptyl, or cyclooctyl, etc.; and it ispreferably, cyclopentyl or cycohexyl.

The term "aminoalkyl" means an straight alkyl having an amino group and 1 to 8 carbons, and includes particularly, 8-aminooctyl, 6-aminohexyl, 4-aminobutyl, 2-aminoethyl, or aminomethyl; preferably, it is 2-aminoethyl or aminomethyl.

The term "mono- or di-alkylamino" means methylamino, dimethylamino, ethylamino, propylamino, diethylamino, isopropylamino, diisopropylamino, dibutylamino, butylamino, isobutylamino, sec-butylamino, tert-butylamino, etc.; preferably, it is methylamino, dimethylamino, ethylamino, diethylamino, isopropylamino, or diisopropylamino; and more preferably, it is ethylamino, diethylamino, or isopropylamino.

The term "mono- or di-alkylaminoalkyl" means particularly, methylaminoethyl, dimethylaminoethyl, ethylaminoethyl, methylaminopropyl, dimethylaminopropyl, ethylaminopropyl, diethylaminopropyl, methylaminobutyl, or dimethylaminobutyl, etc.; preferably, it is methylaminoethyl, dimethylaminoethyl, or ethylaminoethyl. "$C_{1-10}$ alkyl" which binds to a nitrogen atom as Z means a straight or branched carbon chain having 1 to 10 carbons, and is for example, methyl, ethyl, propyl, isopropyl, butyl, isobutyl, tert-butyl, pentyl, neo-pentyl, isopentyl, 1,2-dimethylpropyl, hexyl, isohexyl, 1,1-dimethylbutyl, 2,2-dimethylbutyl, 1-ethylbutyl, 2-ethylbutyl, heptyl, isoheptyl, 1-methylhexyl, 2-methylhexyl, octyl, 2-ethylhexyl, nonyl, decyl, or 1-methylnonyl, etc. Among them, one having 1 to 4 carbons is preferable, and isopropyl or propyl is particularly preferable.

The term "arylcarbonyl" means benzoyl, 4-methoxybenzoyl, or 3-trifluoromethylbenzoyl, etc., and preferably, it is benzoyl.

The term "aralkylcarbonyl" includes particularly, benzylcarbonyl, phenethylcarbonyl, phenylpropylcarbonyl, 1-naphthylmethylcarbonyl, or 2-naphthylmethylcarbonyl, etc.; and preferably, it is benzylcarbonyl.

The term "aralkyl" includes particularly, benzyl, phenethyl, phenylpropyl, 1-naphthylmethyl, or 2-naphthylmethyl, etc.; and preferably, it is benzyl, Further, in the definition regarding the substituent in a compound of formula (2) of the present invention:

The term "$C_{1-4}$ alkoxycarbonyl" means methoxycarbonyl, ethoxycarbonyl, propoxycarbonyl, isopropoxycarbonyl, butoxycarbonyl, isobutoxycarbonyl, sec-butoxycarbonyl, or tert-butoxycarbonyl; preferably, it is methoxycarbonyl, ethoxycarbonyl, or tert-butoxycarbonyl; and more preferably, it is methoxycarbonyl.

The term "$C_{1-4}$ alkyl" means a straight or branched carbon chain having 1 to 4 carbons, and includes for example, methyl, ethyl, propyl, isopropyl, butyl, isobutyl, or tert-butyl; and preferably, it is methyl or ethyl.

The term "$C_{1-4}$ alkylcarbonyl" means a carbonyl group having a straight or branched carbon chain having 1 to 4 carbons, and includes for example, hormyl, acetyl, propionyl, butyryl, or isobutyryl, etc.; and preferably, it is acetyl or propionyl.

The term "$C_{5-6}$ cycloalkyl" means a cycloalkyl group having 5 to 6 carbons, and includes cyclopentyl or cyclohexyl; and it is preferably cyclohexyl.

The term "$C_{1-4}$ alkoxy" means an alkoxy group having 1 to 4 carbons, and includes particularly, methoxy, ethoxy, propoxy, isopropoxy, butoxy, isobutoxy, sec-butoxy, or tert-butoxy, etc. Among them, methoxy or ethoxy is preferable.

The compound (1) of the present invention may form acid addition salts. Further, it may form salts with bases, depending on the species of the substituent. These salts are not restricted insofar as they are pharmaceutically acceptable, and include particularly, mineral salts such as hydrochloride, hydrobromide, hydroiodide, phosphate, nitrate or sulfate, etc.; organic sulfonates such as methanesulfonate, 2-hydroxyethanesulfonate or p-toluenesulfonate, etc.; and organic carbonates such as acetate, trifluoroacetate, propionate, oxalate, citrate, malonate, succinate, glutarate, adipate, tartrate, maleate, malate, or mandelate, etc. As salts with bases, salts with inorganic bases such as sodium salts, potassium salts, magnesium salts, calcium salts or alminium salts, and salts with organic bases such as methylamine salts, ethylamine salts, lysine salts or ornithine salts, etc. are included.

The preferred compounds of the invention are found in Table 1.

More preferred compounds of the invention are compounds specified by the following compound numbers, among compounds listed in Table 1.

Compound No.: 23, 29, 30, 31, 53, 54, 57, 58, 59, 60, 91, 92, 93, 115, 119, 120, 121, 156, 166, 168, 201, 205, 206, 207, 244, 245 and 246.

The representative strategies for syhthesizing compounds of formula (1) of the present invention are detailed in the following description.

According to the present invention, in the case that starting compounds or intermediates have substituents which influence the reaction such as hydroxyl, amino or carboxyl, etc., it is preferred to adequately protect such functional groups to carry out the reaction, and then detach the protecting group. The protecting group is not limited insofar as it is one which is usually employed on respective substituents and does not have an adverse effect on the other elements during processes of the protection and deprotection, and includes for example, trialkyllsilyl, $C_{1-4}$ alkoxymethyl, tetrahydropyranyl, acyl or $C_{1-4}$ alkoxycarbonyl as a protecting group on hydroxyl; $C_{1-4}$ alkoxycarbonyl, benzyloxycarbonyl or acyl as a protecting group on amino; and $C_{1-4}$ alkyl as a protecting group on carboxyl. The deprotection reaction can be carried out according to processes which are usually practiced on respective protecting groups.

Among nitriles which are precursors of the present compounds of formula (1), compounds having an oxygen as X can be synthesized, for example, according to the following reaction:

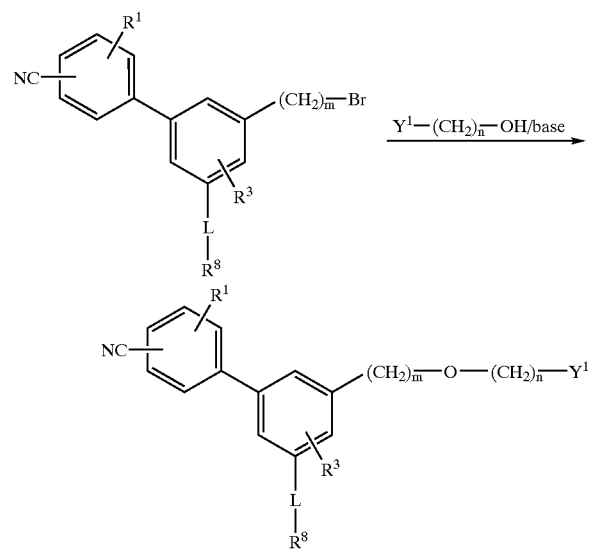

(a-1)

wherein $R^1$, $R^3$, L, m, and n are as defined in formula (1); $Y^1$ means a substituent Y defined in formula (1) except for the one having the structures defined in the formula I-3 as a substituent Z on Y; $R^8$ means hydrogen, fluorine, chlorine, bromine, hydroxyl or protected hydroxyl, amino or protected amino, or $C_{1-8}$ alkoxy.

That is, as seen in the above reaction (a-1), nitrites which are precursors of the compound of the invention can be produced by mixing alcohol represented by formula: $Y^1$—$(CH_2)_n$—OH with a raw material, biphenylalkyl bromide in the presence of bases.

Moreover, among nitriles which are precursors of the present compounds of formula (1), compounds having an oxygen as X can be synthesized, for example, according to the following reaction:

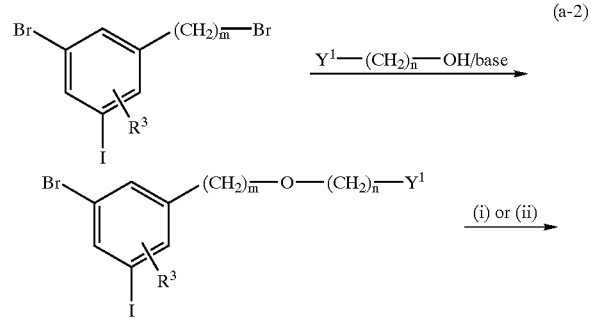

(a-2)

-continued

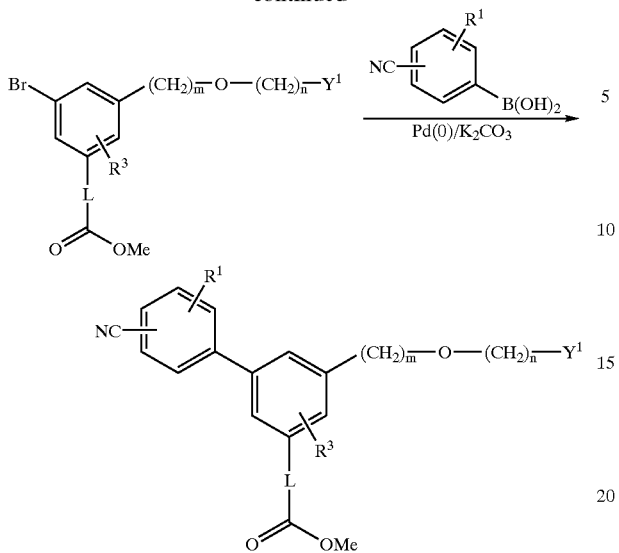

wherein $R^1$, $R^3$, L, m, and n are as defined in formula (1); $Y^1$ means a substituent Y defined in formula (1) except for the one having the structures defined in the formula I-3 as a substituent Z on Y.

That is, nitrites which are precursors of the present compound can be produced by mixing alcohol represented by formula $Y^1$—$(CH_2)_n$—OH with a raw material, 3-bromo-5-iodophenylalkyl bromide in the presence of bases to produce 3-bromo-5-iodophenylalkyl ether, then introducing substituent —L—COOMe into the resulting ether by the monocarbonylation or monoalkylation to produce 3-bromophenylalkylether, and then carrying out the coupling reaction with a cyanophenyl-boronic acid derivative.

The etherification of the first step in reactions (a-1) and (a-2) is carried out using aliphatic ether solvent, such as tetrahydrofuran or diethylether, aprotic hydrocarbons such as benzene or toluene, aprotic polar solvents such as DMF or HMPA, or a mixture thereof, etc., and as bases, a metal6oxide such as barium oxide or zinc oxide, metal hydroxide such as sodium hydroxide or potassium hydroxide, or a metal hydride such as sodium hydride, etc. are used. The reaction proceeds at 0–100° C. for 3–72 hours with stirring. Preferably, it is carried out at 20–80° C. for 8–36 hours, using sodium hydride, in absolute aliphatic ethers such as THF or ether.

The reaction for introducing a-substituent: —L—COOMe to ethers, which is the second step of reaction (a-2), can be carried out according to the-following reactions (i) or (ii):

(i) Monocarbonylation by introduction of carbon monoxide (in the case that L is a bond): Iodine can be substituted with methoxycarbonyl group by dissolving the ethers obtained from the first step of reaction (a-1) into methanol, adding bivalent palladium catalyst and bases such as tertiary amine such as triethylamine, and optionally phosphine ligand such as triphenylphosphine, and stirring for 3–48 hours under room temperature or under heating in an atmosphere of carbon monoxide. Preferably, it is carried out using, as a catalyst, bistriphenylphosphine palladium or palladium acetate and as a base, diisopropylethylamine or tributylalmine at 60–80° C. for 12–36 hours.

(ii) Monoalkylation using an organic zinc reagent (in the case that L is $C_{1-8}$ alkylene): Iodine can be substituted with alkyl by dissolving the ethers obtained from the first step of reaction (a-1) and 0-valence palladium catalyst such as tetrakistriphenylphosphine palladium into the solvent such as THF or DMF, benzene, or toluene, or a mixture thereof, adding, to this solution, THF solution containing alkyl zinc reagent of formula: I—Zn—L—COOMe, and stirring for 3–48 hours under room temperature or under heating. Preferably, it is carried out using, as a catalyst, tetrakistriphenylphosphine palladium and as a solvent, THF, at 20–80° C. for 6–36 hours.

The biphenylation which is the third step of the reaction (a-2) can be carried out by reacting monohalide with cyanophenyl boron acid in presence of palladium catalyst. This reaction proceeds usually by heating, with stirring in DMF, the monohalide obtained from the second step of the reaction (a-2) and bivalent palladium catalyst such as palladium acetate, and additionally, bases-such as triethylamine, and triarylphosphines to produce the cyanobiphenyl compound of interest. Preferably, it is carried out at 60–100° C. for 2–24 hours.

Moreover, among nitrites which are precursors of the present compounds of formula (1), compounds having a nitrogen as X can be synthesized, for example, according to the following reactions (b-1) and (b-2):

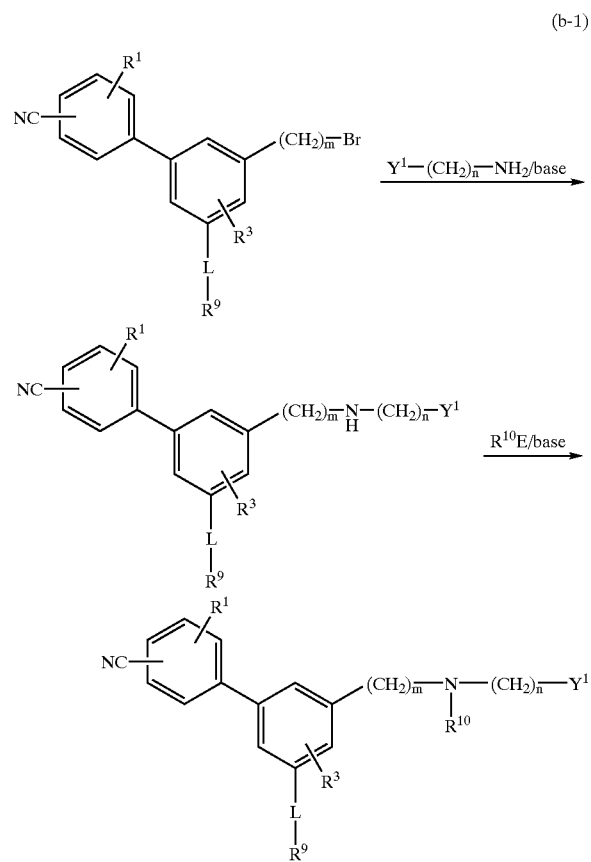

(b-1)

wherein $R^1$, $R^3$, L, m, and n are as defined in formula (1); $R^9$ means fluorine, chlorine, bromine, hydroxyl or protected hydroxyl, amino or protected amino, $C_{1-8}$ alkoxy, or methoxycarbonyl among substituent $R^2$ defined in formula (1); $Y^1$ means a substituent Y defined in formula (1) except for the one having the structures defined in the formula I-3 as a substituent Z on Y; $R^{10}$ means a substituent $R^4$ except for hydrogen and aryl; E is a leaving group such as chlorine, bromine, iodine, acyloxy or sulfonyloxy.

(b-2)

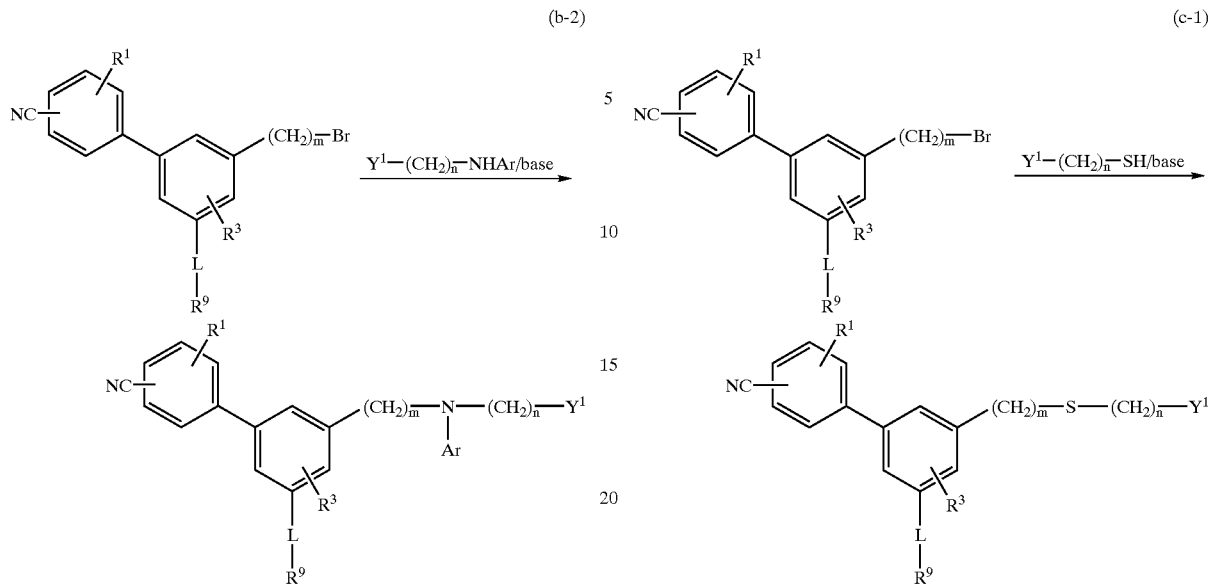

wherein $R^1$, $R^3$, L, m, and n are as defined in formula (1): $R^9$ means fluorine, chlorine, bromine, hydroxyl or protected hydroxyl, amino or protected amino, $C_{1-8}$ alkoxy, or methoxycarbonyl among substituent $R^2$ defined in formula (1); $Y^1$ means a substituent Y defined in formula (1) except for the one having the structures defined in the formula I-3 as a substituent Z on Y; Ar means aryl; E is a leaving group such as chlorine, bromine, iodine, acyloxy or sulfonyloxy.

The N-alkylation of reactions (b-1) and (b-2) can be carried out using a condition for alkylation which is known. That is, the starting material, biphenylalkylbromide can be reacted with amines of formula: $Y^1$—$(CH_2)_n$—$NH_2$ in the presence of mineral salts such as potassium carbonate or amines such as tertiary amines which act as a base, to produce a secondary amine which is a compound of the present invention. This compound can be reacted with alkylating agent of formula: $R^4$—E to produce a tertiary amine which is a compound of the present invention. The above reactions are carried out usually by mixing amines with alkylating agents at optional rate in suitable solvents, and stirring then for 1–96 hours under cooling, under room temperature or under heating. Usually, the reactions are carried out using, as a base, mineral salts such as potassium carbonate or sodium carbonate or organic tertiary amines such as triethylamine or pyridine, and using, as a solvent, alcohols such as methanol or ethanol, hydrocarbons such as benzene or toluene, or a solvents which do not influence the reaction such as THF, dioxane, acetonitrile, DMF or DMSO, or a mixture thereof, at the rate of alkylating agents to amines of 1:10–10:1. Preferably, it is done at an alkylating agents to amines rate of 1:5–1:1, under room temperature or under heating, for 2–24 hours.

Among nitriles which are precursors of the present compounds of formula (1), compounds having a sulfur as X can be snthesized, for example, according to the following reactions (c-1) and (c-2):

(c-1)

wherein $R^1$, $R^3$, L, m, and n are as defined in formula (1): $R^9$ means fluorine, chlorine, bromine, hydroxyl or protected hydroxyl, amino or protected amino, $C_{1-8}$ alkoxy, or methoxycarbonyl among substituent $R^2$ defined in formula (1); $Y^1$ means a substituent Y defined in formula (1) except for the one having the structures defined in the formula I-3 as a substituent Z on Y; and E is a leaving group such as chlorine, bromine, iodine, sulfonate.

(c-2)

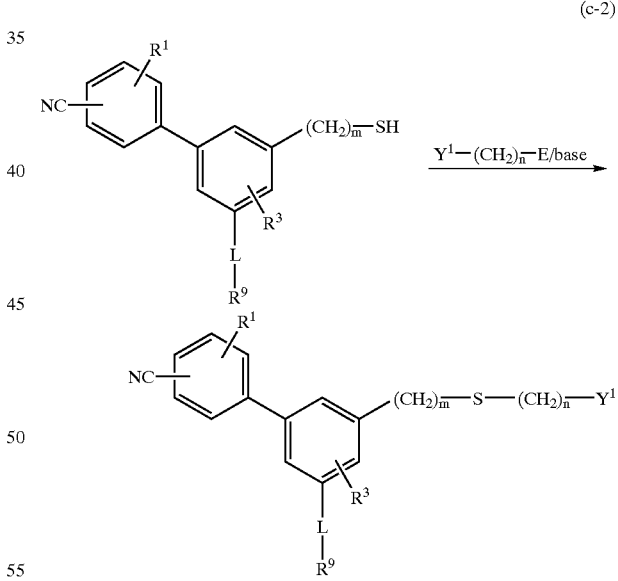

wherein $R^1$, $R^3$, L, m, and n are as defined in formula (1): $R^9$ means fluorine, chlorine, bromine, hydroxyl or protected hydroxyl, amino or protected amino, $C_{1-8}$ alkoxy, or methoxycarbonyl among substituent $R^2$ defined in formula (1); $Y^1$ means a substituent Y defined in formula (1) except for the one having the structures defined in the formula I-3as a substituent Z on Y; and E is a leaving group such as chlorine, bromine, iodine, or sulfonate.

The thioetherification of reactions (c-1) and (c-2) can be carried out-using a condition for thioetherification which is known. Usually, it is done by mixing alkyl halides with thiols at an optional rate in suitable solvents in the presence of bases such as sodium hydroxide or ammonia, and stirring them under cooling, under room temperature or under heating for minutes to 96 hours. As a solvent, compounds which do not act on the reaction such as water, ethanol, DMF or toluene are employed, and as a base, sodium hydroxide, ammonia or cesium carbonate, etc. is employed. The reactions are carried out preferably by mixing at the rate of alkyl halides to thiols being 1:5–5:1, and stirring under room temperature or under heating for 30 minutes to 24 hours.

Moreover, the resulting sulfide can be subjected to oxidation such as in the following reaction (d) to produce a compound having sulfoxide or sulfone as X among the compound of formula (1).

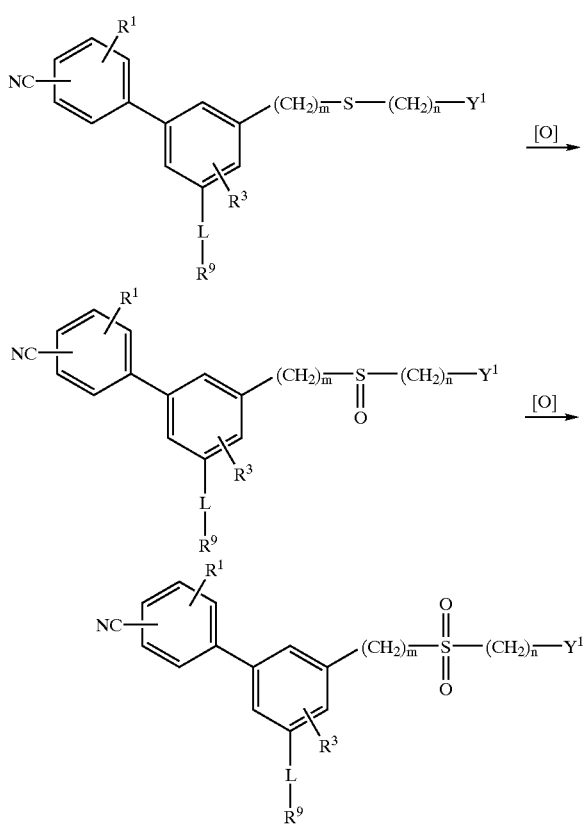

wherein $R^1$, $R^3$, L, m, and n are as defined in formula (1): $R^9$ means fluorine, chlorine, bromine, hydroxyl or protected hydroxyl, amino or protected amino, $C_{1-8}$ alkoxy, or methoxycarbonyl among substituent $R^2$ defined in formula (1): and $Y^1$ means a substituent Y defined in formula (1) except for the one having the structures defined in the formula I-3 as a substituent Z on Y.

The oxidation of reaction (d) can be carried out according to a process described in Jikken Kagaku Kohza (The 4th Edition), 24, Organic Synthesis VI—heteroelement.metallic element compounds—, p.350–373, edited by the Japan Chemical Association. Usually, the reaction is carried out using sulfides or sulfoxides using alcohols such as water or ethanol, etc. as a solvent and hydrogen peroxide, peracetic acid, metaperiodic acid or m-chloroperbenzoic acid, etc. as an oxidizing agent under cooling, under room temperature or under heating with stirring for 30 minutes to 24 hours. Preferably, the sulfoxide is produced for 30 min to 12 hours at 0–20° C., while the sulfone is produced for 1–12 hours at 0–80° C.

Further, among nitrites which are precursors of the present compounds of formula (1), compounds having an amido linkage as X can be synthesized, for example, according to the following reactions (e-1) and (e-2):

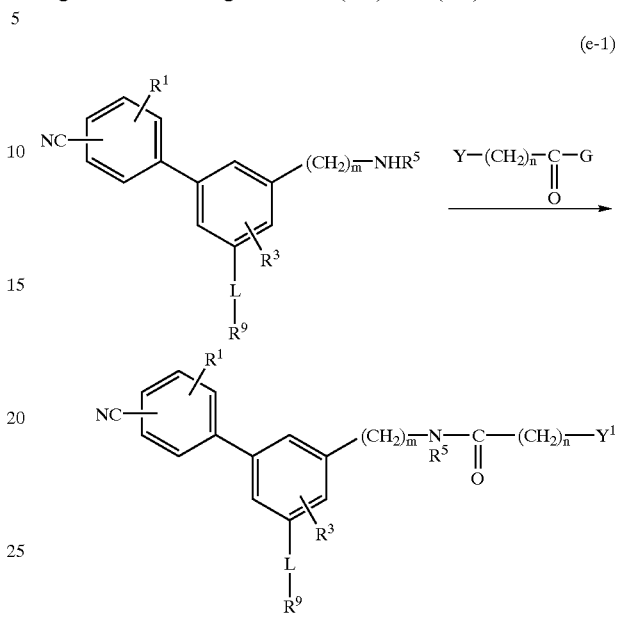

wherein $R^1$, $R^3$, $R^5$, L, m, and n are as defined in formula (1); $R^9$ means fluorine, chlorine, bromine, hydroxyl or protected hydroxyl, amino or protected amino, $C_{1-8}$ alkoxy, or methoxycarbonyl among substituent $R^2$ defined in formula (1): $Y^1$ means a substituent Y defined in formula (1) except for the-one having the structures defined in the formula I-3 as a substituent Z on Y; and G is halogen, acyloxy, p-nitrophenoxy or hydroxyl, etc.

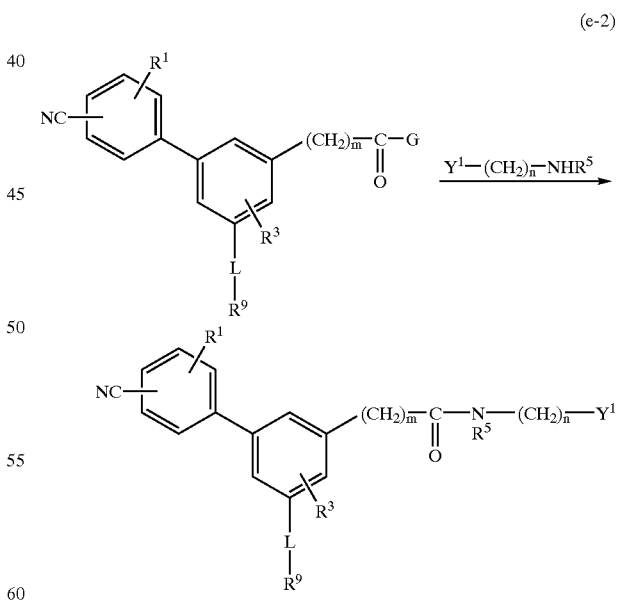

wherein $R^1$, $R^3$, $R^5$, L, m, and n are as defined in formula (1): $R^9$ means fluorine, chlorine, bromine, hydroxyl or protected hydroxyl, amino or protected amino, $C_{1-8}$ alkoxy, or methoxycarbonyl-among substituent $R^2$ defined in formula (1); $Y^1$ means a substituent Y defined in formula (1) except for the one having the structures defined in the formula I-3 as a substituent Z on Y; and G is halogen, acyloxy, p-nitrophenoxy or hydroxyl, etc.

The reactions of (e-1) and (e-2) can be carried out using a condition for amidation which is known. Usually, the amides can be obtained by mixing active derivatives of carboxylic acids with amine compounds in suitable solvents in the presence of bases, for acylation. As the active derivatives of carboxylic; acids for use, active esters such as acid halides, mixed acid anhydrides or p-nitrophenol, etc. are employed under cooling or under room temperature for 30 minutes to 24 hours. Preferably, it is done in halogenated hydrocarbons such as dichloromethane, aliphatic ethers such as THF or diethylether, or solvents such as acetonitrile or DMF, or a solvent mixture thereof, using tertiary amines such as triethylamine as bases, at 0–20° C. for 1–18 hours.

Also, these amides can be obtained by the condensation between amines and carboxylic acids in presence of condensating agents such as carbodiimides. In this case, halogenated hydrocarbons such as DMF or chloroform as solvents are suitable while N,N-dicyclohexylcarbodiimide, 1-ethyl-(3-(N,N-dimethylamino)propyl)carbodiimide, carbonyldiimidazole, diphenylphosphorylazide, or diethylphosphorylcyanide are suitable as condensating agents. The reaction is usually carried out under cooling or under room temperature for 2–48 hours.

Moreover, among nitrites which are precursors of the present compounds of formula (1), compounds having a sulfoneamide structure as X can be synthesized, for example, according to the following reactions (f-1) or (f-2)

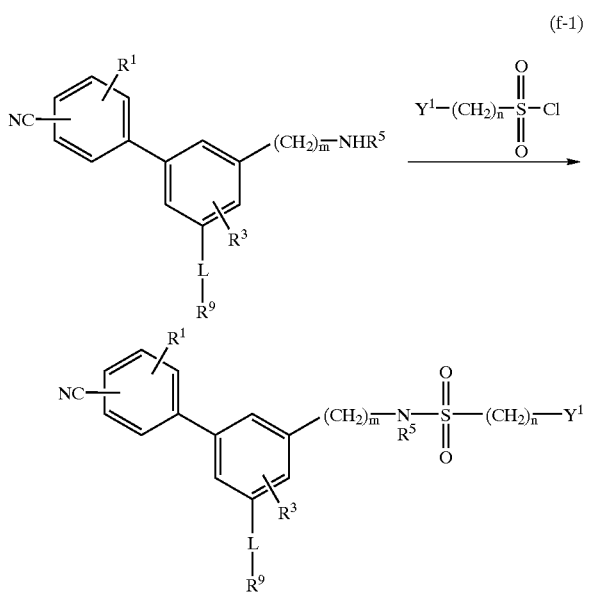

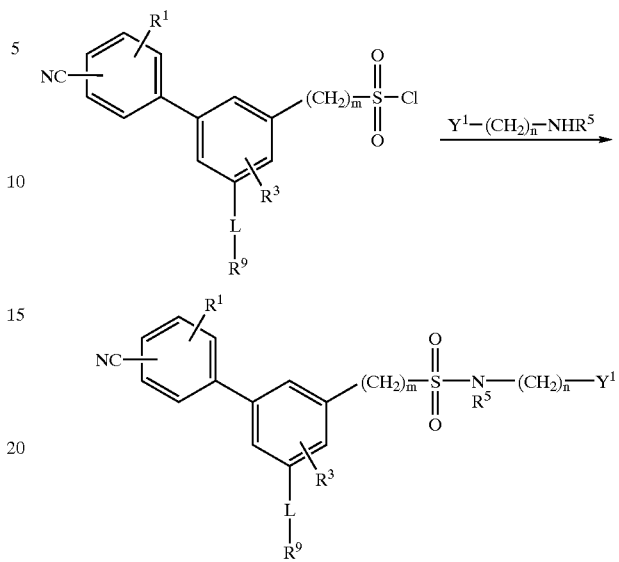

wherein $R^1$, $R^3$, $R^5$, L, m, and n are as defined in formula (1); $R^9$ means fluorine, chlorine, bromine, hydroxyl or protected hydroxyl, amino or protected amino, $C_{1-8}$ alkoxy, or methoxycarbonyl among substituent $R^2$ defined in formula (1); and $Y^1$ means a substituent Y defined in formula (1) except for the one having the structures defined in the formula I-3 as a substituent Z on Y.

The reactions of (f-1) and (f-2) can be carried out by reacting an amine with active derivatives of sulfonic acids in suitable solvents in the presence of bases to produce sulfonamids of interest. As the active derivatives of sulfonic acids, sulfonyl halide is preferable, and the reaction is carried out in, halogenated hydrocarbons such as dichloromethane, aliphatic ethers such as THF or diethylether; a solvent such as acetonitrile or DMF, or a mixture of the solvents at 0–20° C. for 1–24 hours, using tertiary amines such as triethylamine as a base.

Also, among nitrites which are precursors of the present compounds of formula (1), compounds having a urea structure as X can be synthesized, for example, according to the following reaction (g):

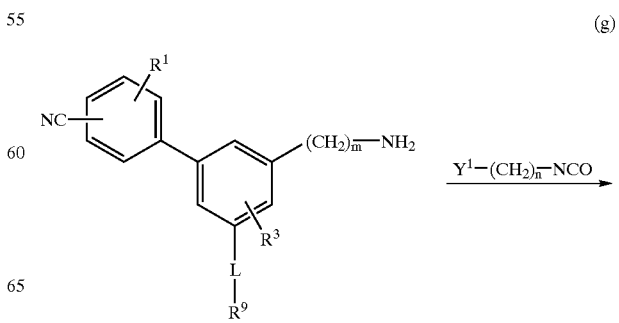

-continued

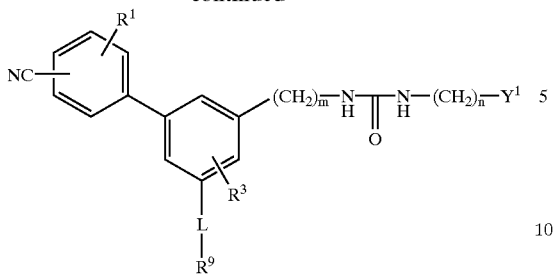

wherein $R^1$, $R^3$, L, m and n are as defined in formula (1): $R^9$ means fluorine, chlorine, bromine, hydroxyl or protected hydroxyl, amino or protected amino, $C_{1-8}$ alkoxy, or methoxycarbonyl among substituent $R^2$ defined in formula (1); and $Y^1$ means a substituent Y defined in formula (1) except for the one having the structures defined in the formula I-3 as a substituent Z on Y.

That is, compounds having a urea structure as X can be produced by reacting, as a raw material, amine with isocyanate derivatives in a suitable solve under cooling to heating. A solvent used in this reaction can be DMF, THF, dioxane, dichloroethane, chloroform, acetnitrile, DMSO, benzene, or toluene, etc.

The nitrites which are precursors of the compound of the present invention produced by the above reactions (a-1), (a-2), (b-1), (b-2), (c-1), (c-2), (d), (e-1), (e-2), (f-1), (f-2), and (g) can be converted to the biphenylamidine derivatives which are a compound of the present invention by the reaction of amidination as follows:

(h)

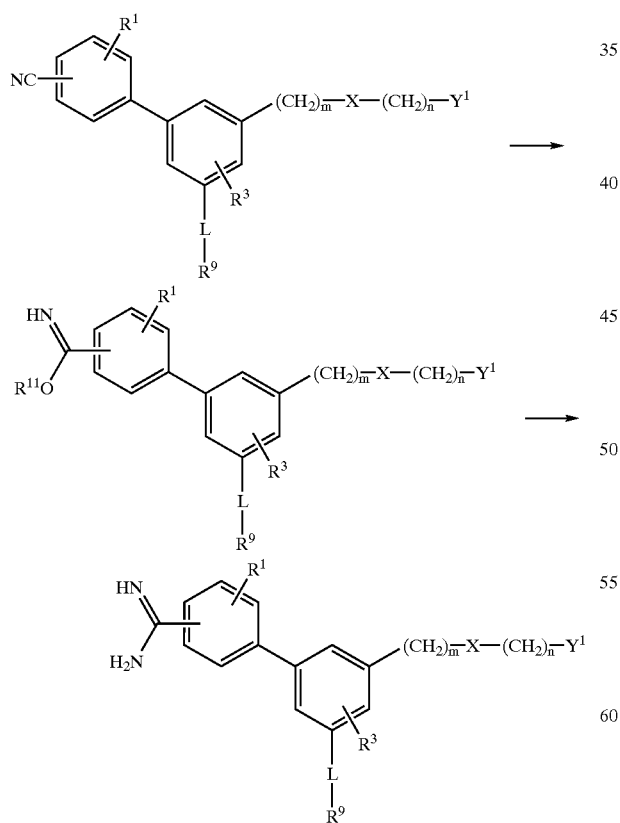

wherein $R^1$, $R^3$, L, X, m and n are as defined in formula (1); $Y^1$ means a substituent Y defined in formula (1) except for the one having the structures defined in the formula I-3 as a substituent Z on Y; $R^9$ means fluorine, chlorine, bromine, hydroxyl or protected hydroxyl, amino or protected amino, $C_{1-8}$ alkoxy, or methoxycarbonyl among substituent $R^2$ defined in formula (1); and $R^{11}$ means $C_{1-4}$ alkyl. This amidination is carried out according to the condition for reaction detailed in the following (iii) or (iv):

(iii) Amidination through imidation using hydrogen halide in alcohol solution: The reaction by which the imidates are obtained from nitriles and alcohols, proceeds, for example, by dissolving alkoxymethylphenylbenzonitriles in alcohols having 1 to 4 carbons ($R^{11}OH$) containing hydrogen halides such as hydrogen chloride or hydrogen bromide, etc. with stirring. The reaction is usually carried out at −20−+30° C., for 12–96 hours. Preferably, it is done in a hydrogen chloride in methanol or ethanol solution, at −10−+30° C., for 24–72 hours. The reaction between the imidate and ammonia proceeds by stirring the imidate in an alcohol having 1 to 4 carbons such as methanol or ethanol containing ammonia or amines such as hydroxylamine, hydrazine or carbamate ester, or in aliphatic ethers such as diethylether, or in halogenated hydrocarbons such as dichloromethane or chloroform, or a mixture thereof to produce the biphenylamidine derivative which is a compound of the present invention. The reaction is usually carried out at the temperature of −10−+50° C., for 1 to 48 hours. Preferably, it is carried out at 0–30° C. for 2–12 hours.

(iv) Amidination through an imidate prepared by direct bubbling of hydrogen halide: The reaction between nitriles and alcohols proceeds, for example by dissolving nitriles in aliphatic ethers such as diethylether, or halogenated hydrocarbons such as chloroform, or aprotic solvents such as benzene, adding the equivalent or an excess of an alcohol having 1 to 4 carbons ($R^{11}OH$), bubbling hydrogen halides such as hydrogen chloride or hydrogen bromide at −30–0° C. for 30 minutes to 6 hours with stirring, then stopping the bubbling, and stirring at 0–50° C. for 3–96 hours. Preferably, it is done by bubbling hydrogen chloride for 1–3 hours at −10–0° C. with stirring in halogenated hydrocarbons containing the equivalent or excess methanol or ethanol, then stopping the bubbling, and stirring at 10–40° C. for 8–24 hours. The resulting imidates can be converted to biphenylamidine derivatives (1) which are compounds of the present invention by stirring them in alcohol solvents having 1 to 4 carbons such as methanol or ethanol containing ammonia or amines such as hydroxylamine, hydrazine or carbamate ester, or aliphatic ether solvents such as diethylether, or halogenated hydrocarbon solvents such as chloroform, or a ixture thereof. The reaction is usually carried out at the temperature of −20−+50° C. for 1–4 hours. Preferably, it is carried out in saturated ammonia ethanol solution at 0–30° C. for 2–12 hours.

Among the compounds of the present invention of formula (1), compounds having a substituent Y wherein a substituent Z has the structures defined in formula I-3 can be produced by carrying out the imidoylation of the, following (j-1) and (j-2), after yielding the biphenylamidine compounds having a secondary amino group in a substituent Y by the above reaction (h):

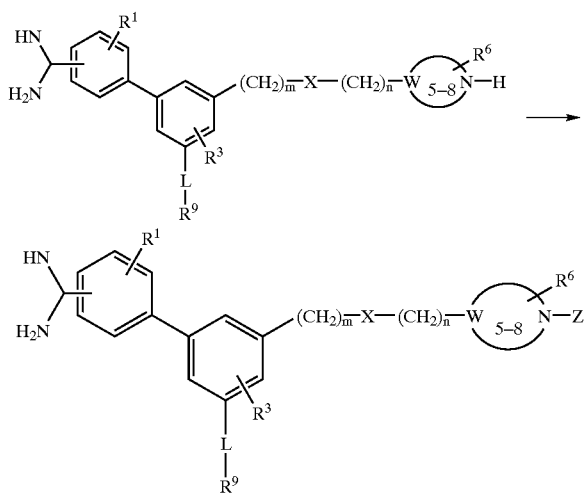

(j-1)

wherein $R^1$, $R^3$, $R^6$, L, W, X, Z, m and n are as defined in formula (1); $R^9$ means fluorine, chlorine, bromine, hydroxyl or protected hydroxyl, amino or protected amino, $C_{1-8}$ alkoxy, or methoxycarbonyl among substituent $R^2$ defined in formula (1).

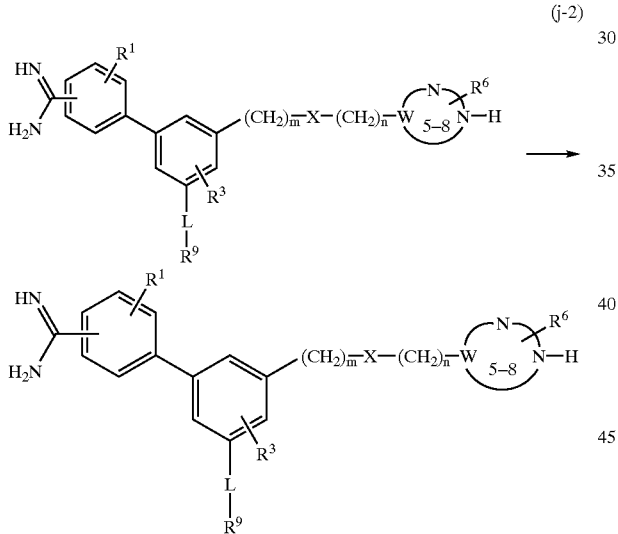

(j-2)

wherein $R^1$, $R^3$, $R^6$, L, X, Z, m and n are as defined in formula (1); $R^9$ means fluorine, chlorine, bromine, hydroxyl or protected hydroxyl, amino or protected amino, $C_{1-8}$ alkoxy, or methoxycarbonyl among substituent $R^2$ defined in formula (1).

This imidoylation, proceeds by mixing biphenylamidine compounds having a secondary amino group in a substituent Y with the equivalent, or excess imidates in water, or alcohols having, 1 to 4carbons such as methanol or ethanol, or aliphatic ethers such as diethylether, or halogenated hydrocarbons such as chloroform, or polar solvents such as DMF or DMSO, or a mixture thereof in presence of bases, with stirring. The reaction is usually carried out at room temperature for 1–24 hours. As a base, N-methylmorphpline, triethylamine, diisopropylethylamine, sodium hydroxide, or potassium hydroxide, etc. can be used.

Among the compounds of the present invention of formula (1), compounds having a carboxyl as $R^2$ are produced by ester hydrolysis of compounds having methoxycarbonyl as $R^9$ among the biphenylamidine compounds produced by the above reaction (h), (j-1) and (j-2). This hydrolysis can be carried out under a basic condition, an acidic condition, or a neutral condition, if necessary. In the reaction under the basic condition, as a base, sodium hydroxide, potassium hydroxide, lithium hydroxide, or barium hydroxide, etc. can be used, and under the acidic condition, hydrochloric acid, sulfuric acid, or Lewis acids such as boron trichloride, trifluoroacetic acid, or p-toluenesulfonic acid, etc., are included, while under the neutral condition, a halogen ion such as lithium iodide or lithium bromide, alkali metal salts with thiol or selenol, iodotrimethylsilane, and enzymes such as esterase are included. The solvent for use includes polar solvents such as water, alcohols, acetone, dioxane, THF, DMF, DMSO, etc., or a mixture thereof. The reaction is usually carried out at room temperature or under heating for 2–96 hours. The suitable condition of the reaction temperature or the reaction time, etc. differs, depending on the reaction condition used, and can be selected appropriately by a conventional process.

In the compounds having a carboxyl is a substituent $R^2$, obtained from the above process, the carboxyl can be converted to the other esters by the following process (v), (vi), or (vii):

(v) Conversion from carboxyl to alkoxycarbonyl: The carboxyl can be converted to the alkoxycarbonyl by reacting compounds having carboxyl as a substituent $R^2$ among compounds of formula (1) with the equivalent or excess alkylating agents (for example, methyl acyloxychlorides such as methyl acetoxychloride or methyl pivaloyloxychloride, or allyl chlorides, or benzyl chlorides) in halogenated hydrocarbons such as dichloromethane, or aliphatic ethers such as THF, or aprotic polar solvents such as DMF, or a mixture thereof, under presence of tertiary amines such as triethylamine or diisopropylethylamine, at −10–+80° C. for 1–48 hours. Preferably, it is done using the equivalent to a slight excess of alkylating agent, in the presence of diisopropylethylamine, at 20–60° C., for 2–24 hours.

(vi) Conversion from carboxyl to aralkoxycarbonyl: The carboxyl can be converted to the aralkoxycarbonyl by reacting compounds having carboxyl as a substituent $R^2$ among compounds of formula (1) with the equivalent or excess alcohols such as benzyl alcohol in a solvent of halogenated hydrocarbons such as dichloromethane, in the presence of acid catalysts such as hydrogen chloride, sulfuric acid or sulfonic acid. The reaction is usually carried out at room temperature or under heating for 1–72 hours. Preferably, it is done using the equivalent to a sight excess of alcohols under presence of diisopropylethylamine, at 20–60° C., for 2–24 hours.

(vii) Conversion of carboxyl to aryloxycarbonyl: The carboxyl can be converted to the aryloxycarbonyl by reacting compounds having carboxyl as a substituent $R^2$ among compounds of formula (1) with the equivalent or an excess of aromatic compound having hydroxyl such as phenol in a solvent of aliphatic ethers such as diethylether, under presence of the condensating agents such as dicyclohexylcarbodiimide. The reaction is usually carried out at 0–50° C. for 1–48 hours. Preferably, it is done at room temperature for 3–24 hours.

Also, compounds having a carboxyl as $R^2$ can be converted to ones having carbamoyl by known techniques, for example, by treating the carboxyl with oxalyl chloride, etc. to produce acid halides, and reacting with ammonia solution. Similarly, it can be converted to N-methyl-N-methoxycarbamoyl by acid halides with N-methyl-N-methoxyamine, and further this can be converted to alkylcarbonyl by reacting with various alkylmagnesium reactants.

Among the present compounds synthesized by the above processes, compounds having an amidino group as a substituent A can be introduced through one of the nitrogen atoms constituting the amidino group with various carbonyls by the following process (ix), (x), or (xi).

(ix) Aryloxycarbonylation of amidino: Aryloxycarbonyl can be introduced through one of the nitrogen atoms constituting an amidino by stirring compounds having, an amidino as a substituent A among the compounds of formula (1) with the equivalent to excess aryl chloroformates such as phenyl chloroformate in a mixed solvent of water and halogenated hydrocarbons such as dichloromethane in the presence of bases such as sodium hydroxide or potassium hydroxide. The reaction is usually carried out at −10−+40° C. for 3–48 hours. Preferably, it is done using the equivalent or a little excess aryl chloroformate at 0–30° C. for 6–24 hours.

(x) Alkoxycarbonylation of amidino: Alkoxycarbonyl can be introduced through one of the nitrogen atoms constituting an amidino by reacting compounds having an amidino as a substituent A among the compounds of formula (1) with the equivalent to excess alkylcarbonic acid p-nitrophenyl ester in an absolute solvent such as THF or DMF in the presence of bases such as metal hydrides such as sodium hydride or tertiary amines, at −10−+30° C. for 3–48 hours. Preferably, it is done with the equivalent to a slight excess of p-nitrophenyl ester of alkylcarbonates under presence of tertiary amines such as triethylamine or diisopropylethylamine, at −10−+40° C. for 6–24 hours.

(xi) Arylcarbonylation of amidino: Arylcarbonyl can be introduced through one of the nitrogen atoms constituting an amidino by reacting compounds having an amidino as a substituent A among the compounds of formula (1) with the equivalent to excess aromatic carboxylic acid chloride such as benzoylchloride in halogenated hydrocarbons such as methylene chloride or solvents such as THF, DMF or pyridine, or a mixture thereof in the presence of bases such as amines, at −10−+30° C. for 1–48 hours. Preferably, it is done with the equivalent to a slight excess of aromatic carboxylic acid chloride under presence of amines such as triethylamine, diisopropylethylamine or pyridine, at −10−+40° C. for 2–24 hours.

Furthermore, the compounds of formula (1) can be produced by an optional combination of other well-known etherification, amidination, hydrolysis, alkylimidoylation, amidationor esterification processes, or process which is usually employed by those skilled in the art.

The biphenylamidine derivatives (1) produced as above, can be isolated and purified by the known techniques for example by extraction, precipitation, fractional chromatography, fractional crystallization, or recrystallization, etc. Further, a pharmaceutically acceptable salt of the compound of the present invention can be produced by subjecting it to a usual salt-forming reaction.

The biphenylamidine derivatives and pharmaceutically acceptable salts thereof of the invention have an effect of inhibiting FXa activity, and can be used as a prophylactic agent and/or a therapeutic agent which are clinically applicable against thromboembolism such as myocardial infarction, cerebral thrombosis, thrombosis of peripheral artery or thrombosis of deep vein as a FXa inhibitor.

Moreover, the biphenylamidine derivatives of the invention can constitute pharmaceutihcal compositions with pharmaceutically acceptable carriers, and be administered orally or parenterally in various dosage form. Parenterally administration includes for example, administration by intravenous, subcutaneous, intramusclar, transdermal, intrarectal, transnasal and instillation methods.

The dosage form of the pharmaceutical composition includes the following: For example, in the case of oral administration, tablets, pills: granules, powder, solution, suspension, syrup, or capsules, etc. can be used.

As a method for producing a tablet, it can be formed by conventional techniques using a pharmaceutically acceptable carrier such as excipient, binder or disintegrant, etc. Also, the form of a pill, granules, or powder can be produced by the conventional techniques using excipient, etc. in the same manner as the tablet. The form of a solution, suspension or syrup can be produced by the conventional techniques using glycerol esters, alcohols, water or vegetable oils, etc. The form of capsule can be produced by filling a capsule made of gelatine, etc. with the granules, powder or a solution, etc.

Among the agents for parenteral administration, in the case of intravenous, subcutaneous or intramuscular administration, it can be administered as injection. A injection can be produced by dissolving the biphenylamidine derivatives in water soluble solutions such as, for example physiological salt solution, or water insoluble solutions consisting of organic esters such as for example, propylene glycol, polyethylene glycol, or vegetable oils, etc.

In the case of transdermal administration, for example, a dosage form as an ointment or a cream can be employed. The ointment can be produced by using the biphenylamidine derivative in the mixture of fats and oils or vasehlines, etc., and the cream can be produced by mixing the biphenylamidine derivative with emulsifiers.

In the case of rectal administration, it may be in the form of suppository using a gelatine soft capsule, etc.

In the case of transnasal administration, it can be used as an formulation consisting of a liquid or powdery composition. As a base of a liquid formulation, water, salt solution, phosphate buffer, or acetate buffer, etc. are used, and also, it may contain surfactants, antioxidants, stabilizers, preservatives, or tackifiers. A base of powdery formulation may include water-absorbing materials such as, for example, highly water-soluble polyacrylates, cellulose low-alkylethers, polyethylene glycol polyvinylpyrrolidone, amylose or pullulan, etc., or water-unabsorbing materials such as, for example, celluloses, starches, proteins, gums or cross-linked vinyl polymers. The water-absorbing materials are preferable. These materials may be mixed for use. Further, antioxidants, colorants, conservatives, preservatives or, antiseptic etc. may be added to the powdery formulation. The liquid or powdery formulation can administrated, for example, using a spray apparatus.

In the case of eye drop administration, an aqueous or non-aqueous eye drop can be employed. In the aqueous eye drop, as a solvent, sterilized and purified water or physiological salt solution, etc. can be used. When only the sterilized and purified water is employed as a solvent, an aqueous suspended eye drop can be formed by adding a suspension such as surfactants or high-molecular tackifiers, or a soluble eye drop by adding solubilizers such as nonionic surfactants. In the non-aqueous eye drop, a non-aqueous suspended eye drop can be formed by using injectable non-aqueous solvents as a solvent.

In the case of administering through the eyes by means other than eye drops, the dosage form such as eye-ointments, applicating solutions, diffusing agents or insert agents can be used.

Further, in the case of the inhalation through nose or mouth, a solution or suspension containing a biphenylamidine derivative and a pharmaceutical excipient which is generally utilized is inhaled through, for example, an inhalant aerosol spray, etc. Also, a biphenylamidine derivative which is in the form of dry powder can be administered through inhalator, etc. which contacts directly with lung.

To these formulations, if necessary, pharmaceutically acceptable carriers such as isotonic agents, preservatives, conservatives, wetting agents, buffers, emulsifiers, dispersions or stabilizers, etc. may be added.

Also, if necessary, these formulations can be sterilized by the addition of a sterilant, filtration using a bacteria-retaining filter, or treatment with heat or irradiation, etc. Alternatively, it is possible to produce an aseptic solid formulation, which can be used to be dissolved or suspended in a suitable aseptic solution immediately before use.

The dose of the biphenylamidine of the invention differs depending on kinds of disease, route of administration, or condition, age, sex or weight of the patient, etc., but generally, is about 1–500 mg/day/human body, preferably 10–300 mg/day/human body in the case of oral administration, while is about 0.1–100 mg/day/human body, preferably 0.3–30 mg/day/human body in the case of intravenous, subcutaneous, intramuscle, transdermal, intrarectal, transnasal, instillation or inhalation.

When the biphenylamidine of the invention is used as a prophylactic agent, it can be administered according to well-known processes, depending on the respective condition.

Embodiments

The present invention will be illustrated using the following Productive Examples, Embodiments, and Experiments. However, the scope of the invention is not restricted in any means by these examples.

PRODUCTIVE EXAMPLE 1

Methyl 3-Amino-5-hydroxymethylbenzoate

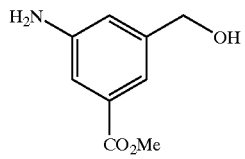

85 g of 3-nitro-5-methoxycarbonylbenzoic acid was dissolved in 200 ml of THF under a flow of nitrogen, and 43.4 ml of borane dimethylsulfide complex was added with stirring under ice-cooling. After stirring for 18 hours, 200 ml of water was added, and then 96 g of potassium carbonate was added. It was extracted with ethyl acetate, and theorganic layer was washed with salt solution. After drying with magnesium sulfate, the resulting solid was dissolved in 800 ml of ethyl acetate, 750 mg of 10% Pd/C was added, and stirring was continued under the flow of hydrogen. After the reaction was completed, it was subjected to the filtration, and then the filtrate was concentrated to produce 64 g of the title compound.

1H-NMR (270 MHz, CDCl$_3$): δ 2.30 (s, 1H ), 3.89 (s, 3H), 4.64 (s, 1H), 6.89 (s, 1H), 7.26 (s, 1H), 7.39 (s, 1H).

PRODUCTIVE EXAMPLE 2

Methyl 5-Hydroxymethyl-3-iodobenzoate

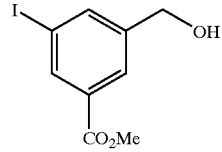

34.3 g of the compound obtained from Productive Example 1 was dissolved in 200 ml of THF, and 75 g of hydroiodic acid was added with stirring under ice-cooling. A 100 ml solution containing 13.73 g of sodium nitrite was added. After stirring at 0° C. for 40 min., a 150 ml solution containing 34.6 g of potassium iodide was added. After stirring at 40° C. for 2 hours, 300 ml of water was added and was concentrated. It was extracted with ethyl acetate, and the organic layer was washed with salt solution. After drying with sodium sulfate, it was purified through silica gel column chromatography to produce 23.1 g (42%) of the title compound.

1H-NMR (270 MHz , CDCl$_3$): δ 1.81 (t, 1H, J=5.6 Hz), 3.92 (s, 3H), 4.72 (d, 1H, J=5.6 Hz), 7.93 (s, 1H), 7.98 (s, 1H), 8.29 (s, 1H).

PRODUCTIVE EXAMPLE 3

Dihydroxy-(3-cyanophenyl)borane

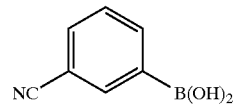

20 g of 3-bromobenzonitrile was dissolved in 100 ml of dry THF and, under a nitrogen atmosphere, 37.6 ml of triisopropoxyborane was added. This solution was cooled to −78° C., and 98.3 ml of 1.6M n-butyllithium hexane solution was dropped for 30 min. with stirring. After stirring at room temperature for 30 min., it was cooled to 0° C., 220 ml of 4M sulfuric acid was added. This solution was refluxed with heating overnight, and then cooled to 0° C. again. 340 ml of 5M sodium hydroxide was added, and extracted with 200 ml of diethyl ether. The aqueous layer was removed, and 6M hydrochloric acid was added until the pH was 2. It was extracted twice with 300 ml of ethyl acetate, dried with magnesium sulfate, and then the solvent was removed. The resulting crude product was recrystallized from DMF-water to produce 11.6 g (72%) of the title compound as acicular light-yellow crystals.

1H-NMR (270 MHz, DMSO-d$_6$): δ 7.6~8.3 (m, 4H), 8.5 (brs, 2H).

PRODUCTIVE EXAMPLE 4

Methyl 3-(3-Cyanophenyl)-5-(hydroxymethyl) benzoate

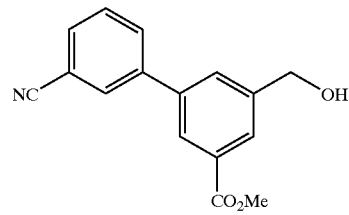

3.08 g of the compound obtained from the above Productive Example 2 was dissolved in 500 ml of dry THF under the flow of nitrogen, and to this solution, 2.32 g of the compound obtained from Productive Example 3, 2.18 g of potassium carbonate, and 456 mg of tetrakis (triphenylphosphine) palladium were added and stirred with heating at 90° C., overnight. The reaction was quenched by adding water, extracted with ethyl acetate, and dried on magnesium sulfate, and then the solvent was removed. It was purified with silica gel column chromatography to produce 2.05 g (73%) of the title compound as colorless crystals.

1H-NMR (270 MHz, CDCl$_3$): δ 2.1 (brs, 1H), 3.96 (s, 3H ), 4.84 (d, 2H, J=3.7 Hz), 7.5~8.2 (m, 7H).

According to the same process of Productive Example 4, compounds of Productive Examples 5–10 which are listed in table 2 were synthesized.

PRODUCTIVE EXAMPLE 11

Methyl 3-(3-Cyanophenyl)-5-(bromomethyl) benzoate

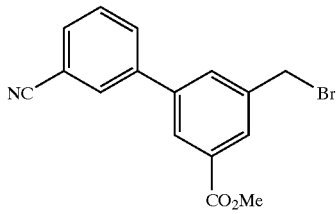

To 1.0 g of the compound obtained from the above Productive Example 4, 20 ml of diethyl ether was added to produce a suspension, and then 0.5 ml of phosphorus tribromide was dropped slowly. The reactant solution was stirred at room temperature for 19 hours, and subjected to extraction. The organic layer was washed with saturated salt solution, dried with sodium sulfate, and then the solvent was removed under vacuum to produce the title compound in the form of a light-yellow solid (1.2 g, 98%)

1H-NMR (270 MHz, CDCl$_3$): δ 3.97 (s, 3H), 4.58 (s, 2H ), 7.5~7.9 (m, 5H ), 8.1~8.2 (m, 2H).

PRODUCTIVE EXAMPLE 12

Methyl 3-(3-Cyanophenyl)-5-(aminomethyl) benzoate

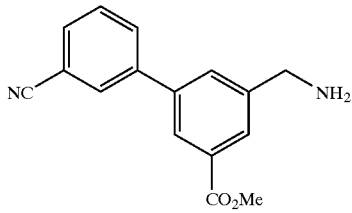

1.1 g of the compound obtained from the above Productive Example 11 was dissolved in 33 ml of DMF, and 325 mg of sodium azide was added. After the reactant solution was stirred at room temperature for 2 hours, 80 mL of water and 120 mL of ethyl acetate were added to extract organic substances, and the aqueous layer was extracted twice with 100 mL of ethyl acetate. The extraction was washed with a saturated salt solution, dried with anhydrous sodium sulfate, and the solvent was removed under vacuum to produce light-yellow-colored, oily methyl 3-(3-cyanophenyl)5-(azidomethyl)benzoate as a crude product.

GC-MS(M−N$_2$)=264.

The Methyl 3-(3-cyanophenyl)-5-(azidomethyl)benzoate obtained as above was put in a flask, dissolved in 66 mL of ethanol, and after 1.1 g of palladium-barium carbonate was added, the air in flask was displaced with hydrogen. Stirring was continued at room temperature for 6 hours, the catalyst was subjected to celite-filtration, and the filtrate was concentrated and purified with silica gel chromatography to produce 794 mg of the title compound (Yield of the two steps: 90%).

GC-MS(M−H)=265

PRODUCTIVE EXAMPLE 13

Methyl 3-(3-Cyanophenyl)-5-[((N-t-butoxycarbonyl) piperidin-4-ylmethyl)aminomethyl)benzoate

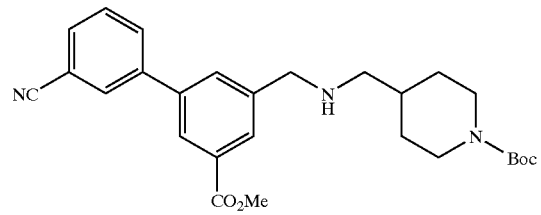

5.5 g of the compound obtained from the above Productive Example 11 was dissolved in 150 ml of dry THF. To this solution, 7.92 g of 4-aminomethyl-(N-t-butoxycarbonyl) piperidine was added and stirred, at room temperature, overnight. This reaction was quenched by pouring this solution into a 0.5M potassium bisulfate solution, and extracted with ethyl acetate. After drying with sodium sulfate, the solvent was removed to produce 10 g of the title compound (potassium bisulfate salt, quantitative).

1H-NMR (270 MHz CDCl$_3$): δ 1.0~1.3 (m, 2H), 1.43 (s, 9H), 1.7~2.0 (m, 3H), 2.6~2.8 (m, 4H), 3.95 (s, 3H), 4.0~4.2 (brs, 4H ), 7.5~7.7 (m, 2H), 7.9~8.0 (m, 2H), 8.20 (s, 2H).

According to the same process of Productive Example 13, compounds of Productive Example 14 which are listed in table 2 were synthesized.

PRODUCTIVE EXAMPLE 15

Methyl 3-(3-Cyanophenyl)-5-[((N-t-butoxycarbonyl) piperidin-4-carbonyl)aminomethyl)benzoate

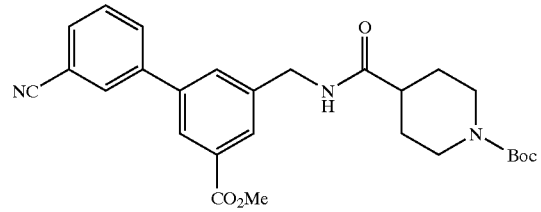

53 mg of the compound obtained from the above Productive Example 12 was dissolved in 2.0 ml of chloroform. To this solution, 57 mg of (N-t-butoxycarbonyl) isonipecotic acid, 27 mg of HOBt, and 48 mg of EDCI hydrochloride was added and stirred, at room temperature, overnight. This reaction was subjected to the cation exchange resin column SCX for the solid-phase extraction and the anion exchange resin column SAX for solid-phase extraction, manufactured by Barian company, and extracted with methanol with removal of impurity. The extract was concentrated to produce 100 mg of the title compound, quantitatively.

MS(M+1)=478.

According to the same process of Productive Example 15, compounds of Productive Examples 16–22 which are listed in table 2 were synthesized.

PRODUCTIVE EXAMPLE 23

Methyl 3-(3-Cyanophenyl)-5-[N-[(N-t-butoxycarbonylpiperidin)-4-7ylmethyl]-N-methylaminomethyl]benzoate

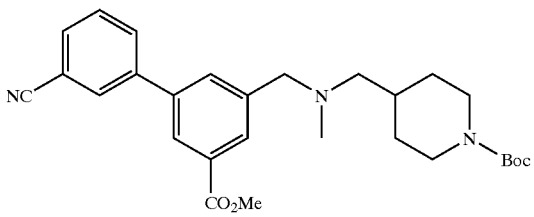

464 g of the compound of the above Productive. Example 13 was dissolved in 13 mL of dimethylformamide, 276 mg of potassium carbonate and 94 μL of methyl iodide were added, and after stirring for 6 hours, the extraction was carried out. The organic layer was washed with salt solution and dried with sodium sulfate, the solvent was removed under vacuum, and it was purified through silica gel chromatography to produce 289 mg of the title compound (Yield: 61%).

1H-NMR (270 MHz, CDCl$_3$): δ 1.0~1.9 (m, 5H), 1.49 (s, 9H), 2.22 (s, 3H), 2.2~2.3 (m, 2H), 2.5~2.8 (m, 2H), 2.70 (t, 2H, J=12.0 Hz), 3.57 (s, 2H), 3.96 (s, 3H), 4.0~4.2 (m, 2H), 4.64 (s, 1H), 4.72 (s, 1H), 7.5~7.7 (m, 2H), 7.72 (s, 1H), 7.85 (d, 1H J=7.6 Hz), 8.01 (s, 1H), 8.12 (s, 1H).

According to the same process of Productive Example 23, compounds of Productive Examples 24–27 which are listed in table 2 were synthesized.

PRODUCTIVE EXAMPLE 28

Methyl 3-(3-Cyanophenyl)-5-[N-[(N-t-butoxycarbonyl)piperidin-4-ylmethyl]-N-acetylaminomethyl]benzoate

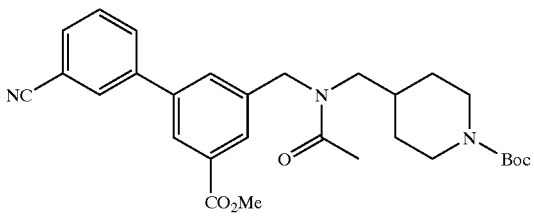

464 g of the compound of the above Productive Example 13 was dissolved in 10 mL of dimethylformamide, and 277 μL of triethylamine was added. 92 μL of acetylchloride was added and stirring was continued for 2 hours. It was poured onto sodium hydrogencarbonate solution and extracted with ethyl acetate. The organic layer was washed with salt solution and dried with sodium sulfate, the solvent was removed under vacuum, and it was purified through silica gel chromatography to produce 349 mg of the title compound (Yield: 69%).

1H-NMR (270 MHz CDCl$_3$): δ 1.0~2.0 (m, 5H), 1.45 & 1.46 (s, 9H), 2.15 & 2.21 (s, 3H), 2.5~2.8 (m, 2H), 3.2~3.3 (m, 2H), 3.96 & 3.97 (s, 3H), 4.0~4.3 (m, 2H), 4.64 & 4.72 (s, 2H), 7.4~8.0 (m, 6H), 8.1~8.2 (m, 1H).

According to the same process of Productive Example 28, compounds of Productive Examples 29–32 which are listed in table 2 were synthesized.

PRODUCTIVE EXAMPLE 33

Methyl 3-(3-Cyanophenyl)-5-[N-[(N-t-butobxycarbonylpiperidin-4-yl) methyl]-N-trifluoroacetylaminomethy]benzoate

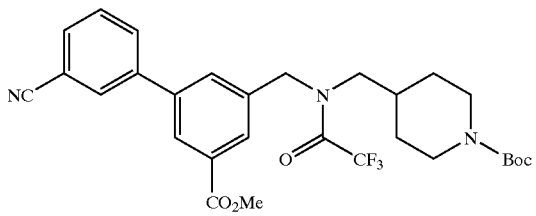

Under the atmosphere of nitrogen, 2.0 g of the compound of the above Productive Example 13 was dissolved in 20 mL of dry DMF, and this solution was cooled to 0° C. With stirring, 1.38 mL of triethylamine was added, and further, 0.70 mL of trifluoroacetic anhydride was added. After stirring under room temperature for 5 hours, water and ethyl acetate were added. The extraction with ethyl acetate was carried out, the organic layer was washed with diluted hydrochloric acid and sodium hydrogencarbonate solution and dried with magnesium sulfate, and the solvent was removed. The purification through silica gel column chromatography resulted in 1.46 g (78%) of the title compound.

MS(M+1)=560.

PRODUCTIVE EXAMPLE 34

Methyl 3-(3-Cyanophenyl)-5-[[2-[(4-t-butoxycarbonyl)piperazin-1-yl]-ethoxy]methyl] benzoate

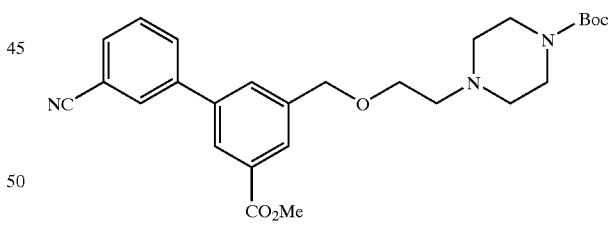

After 24 g of sodium hydride (60% in oil) was suspended in 2.0 mL of dimethylformamide, 2.0 mL of dimethylformamide solution containing 154 mg of 1-t-butoxycarbonyl-4-(2-hydroxyethyl)piperazine was added, and it was stirred for 10 min. After cooling to −30° C., 143 mg of the compound of the Productive Example 11 dissolved in 2.0 mL of dimethylformamide was added, and stirred at −30° C. to room temperature for 4 hours. It was poured onto aqueous saturated ammonium chloride solution, and extracted with ethyl acetate. The combined organic layer was washed with saturated salt solution and dried on magnesium sulfate. After the solvent was removed under vacuum, the purification with silica gel chromatography resulted in 21 mg (Yield: 10%) of the title compound.

1H-NMR (270 MHz, CDCl$_3$): δ 1.45 (s, 9H), 2.4~2.5 (m, 4H), 2.66 (t, 2H, j=5.9 Hz), 3.4~3.5 (m, 4H), 3.66 (t, 2H, j=5.8 Hz), 3.97 (s, 3H), 4.65 (s, 2H), 7.5~8.2 (m, 7H)

PRODUCTIVE EXAMPLE 35

Methyl 3-(3-Cyanophenyl)-5-[(1-acetylpiperidin-4-yl)-methoxymethyl]benzoate

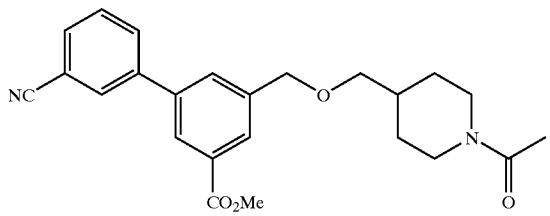

400 mg of the compound of the Productive Example 9 was dissolved in 20 mL of methanol, and 20 mL of 2N hydrochloric acid was added with stirring under ice-cooling. After stirring at 0° C. to room temperature for 7 hours, the concentration yielded the crude product of methyl 3-(3-cyanophenyl)-5-(piperidin-4-ylmethoxymethyl)benzoate. This product was dissolved in 20 mL of dichloromethane, and 3.0 mL of triethylamine was added. 460 μL of acetyl chloride was added with stirring under ice-cooling, the stirring was continued at 0° C. to room temperature for 18 hours, it was poured onto saturated potassium hydrogensulfate solution, and extracted with ethyl acetate. The organic layer was washed with saturated sodium hydrogencarbonate solution and then saturated salt water, dried with magnesium sulfate. After the solvent was removed under vacuum, the purification with silica gel column chromatography resulted in 260 mg (Yield: 74%) of the title compound.

1H-NMR (270 MHz, CDCl$_3$): δ 1.0~1.3 (m, 2H), 1.7~2.0 (m, 3H), 2.09 (s, 3H), 2.56 (td, 1H, J=12.8, 2.9 Hz), 3.06 (td, 1H, J=13.2, 2.0 Hz), 3.2~3.5 (m, 2H), 3.83 (brd, 1H, J=1.35 Hz), 3.97 (s, 3H), 4.65 (s, 2H), 4.5~4.8 (m, 1H), 7.58 (t, 1H, J=7.8 Hz), 7.6~7.8 (m, 1H), 7.72 (s, 1H), 7.85 (d, 1H, J=7.9 Hz), 7.90 (s, 1H), 8.03 (s, 1H), 8.17 (s, 1H).

PRODUCTIVE EXAMPLE 36

Methyl 3-(3-Cyanophenyl)-5-((1-(t-butoxycarbonylmethyl)-4-piperidyl-)-methoxymethyl)benzoate

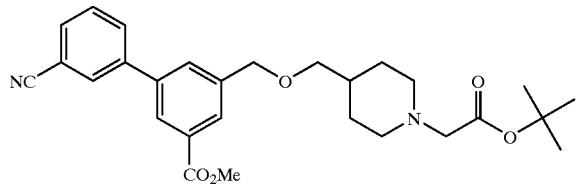

Under the atmosphere of nitrogen, 100 mg of Methyl 3-(3-cyanophenyl)-5-(piperidin-4-yl-methoxymetihyl) benzoate which is obtained as Productive Example 35 was dissolved in 5 ml of dry ethanol, and 56 mg of potassium carbonate and 69 μL of t-Butyl Bromoacetate are added and stirred at 60° C., overnight. The solvent was removed and the purification through silica gel chromatography to produce 10 mg (7.6%) of the title compound.

1H-NMR (270 MHz, CDCl$_3$): δ 1.2~1.4 (m, 2H), 1.46 (s, 9H), 1.6~1.8 (m, 3H), 2.17 (d, J=11 Hz, 2H), 2.96 (d, J=9 Hz, 2H), 3.11 (s, 2H), 3.38 (d, J=6.3 Hz), 3.96 (s, 3H), 4.60 (s, 2H), 7.5~7.9 (m, 5H), 8.03 (s, 1H), 8.15 (s, 1H)

PRODUCTIVE EXAMPLE 37

Methyl 3-(3-Cyanophenyl)-5-[[N-[-(2-hydroxyethyl)piperidine-4-yl-methyl]-N-trifluoroacetyl]aminomethyl]benzoate

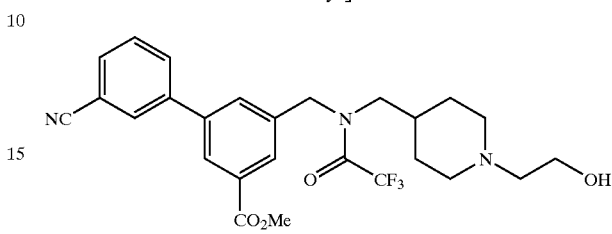

To the compound obtained from the Productive Example 35, 5 mL of trifluoroacetic acid was added at 0° C., and stirred for 30 min. The solvent was removed. Under the atmosphere of nitrogen, to this solution, 20 mL of dry methanol was added, and 300 mg of potassium carbonate and 250 μL of 2-bromoethanol were added and stirred at 60° C., overnight. The solvent was removed, and the purification with silica gel chromatography resulted in 220 mg (71%) of the title compound.

MS(M+H)=504.

PRODUCTIVE EXAMPLE 38

3-(3-Cyanophenyl)-5-[2-(N-tbutoxycarbonylpiperidin-4-yl)-methoxymethyl]benzoic Acid

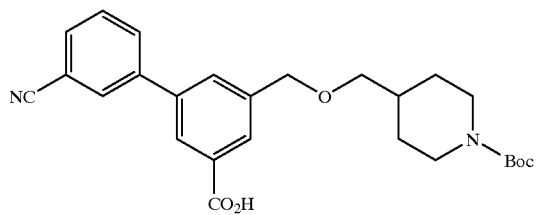

1.43 g of the compound of the Productive Example 9 was dissolved in 20 mL of methanol, and 2 mL of water was added. 1.54 mL of 4N lithium hydroxide solution was added and stirred at room temperature for 3 hours. After acidification by adding a saturated ammonium chloride aqueous solution, the extraction with ethyl acetate was carried out. The organic layer was washed with saturated salt water and dried with magnesium sulfate, the solvent was removed, and the purification through silica gel column chromatography results in 1.03 g (Yield: 74%) of the title compound.

1H-NMR (270 MHz, CDCl$_3$): δ 1.0~1.3 (m, 2H), 1.46 (s, 9H), 1.7~2.0 (m, 3H), 2.56 (td, 1H, J=12.8, 2.9 Hz), 3.05 (td, 1H, J=13.2, 2.0 Hz), 3.2~3.5 (m, 2H), 3.83 (brd, 1H, J=13.5 Hz), 4.65 (s, 2H), 4.6~4.8 (m, 1H), 7.60 (t, 1H, J=7.8 Hz), 7.6~7.8 (m, 1H), 7.74 (s, 1H), 7.85 (d, 1H, J=7.9 Hz), 7.90 (s, 1H), 8.03 (s, 1H), 8.16 (s, 1H)

PRODUCTIVE EXAMPLE 39

3-(3-Cyanophenyl)-5-[(1-tbutoxycarbonylpiperidin-4-yl)methoxymethyl]benzoic Dimethylamide

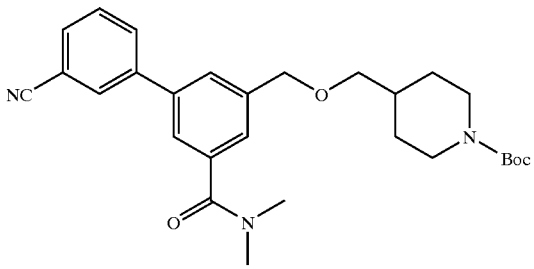

300 mg of the compound of the Productive Example 38 was dissolved in 10 mL of dichloromethane, 116 µL of oxalyl chloride and then 135 µL of pyridine were added at 0° C. and it was stirred at 0° C. for 1 hour. To this reaction solution, 40% dimethylamine solution was dropped and it was stirred at room temperature for 1 hour. Saturated sodium hydrogencarbonate solution was added and extracted with ethyl acetate. The organic layer was washed with saturated salt water, and dried with magnesium sulfate, and the solvent was removed. The resulting crude product was purified through silica gel column chromatography to produce 268 mg (Yield: 84%) of the title compound.

1H-NMR (270 MHz, CDCl$_3$): δ 1.0~1.3 (m, 2H), 1.46 (s, 9H), 1.7~2.0 (m, 3H), 2.56 (td, 1H, J=12.8, 2.9 Hz), 3.0 (brs, 4H), 3.14 (s, 3H), 3.2~3.5 (m, 2H), 3.83 (brd, 1H, J=13.5 Hz), 465 (s, 2H), 4.6~4.9 (m, 1H), 7.60 (t, 1H, J=7.8 Hz), 7.6~7.8 (m, 1H), 7.74 (s, 1H), 7.86 (d, 1H, J=7.8 Hz), 7.92 (s, 1H), 8.04 (s, 1H), 8.17 (s, 1H).

PRODUCTIVE EXAMPLE 40

1-Acetyl-3-(3-cyanophenyl)-5-[(N-t-butoxycarbonylpiperidin-4-yl)methoxymethyl] benzene

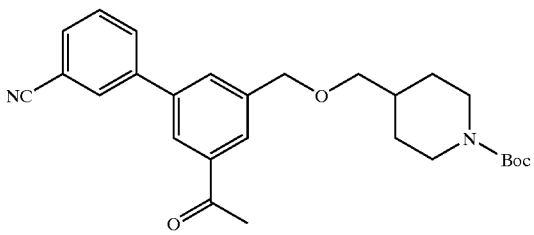

291 mg of the compound of the Productive Example 38 was, dissolved in 10 mL of dichloromethane, 116 µL of oxalyl chloride and then 135 µL of pyridine were added at 0° C. and it was stirred at 0° C. for 1 hour. Then, 76 mg of N,O-dimethylhydroxylamine hydrochloride was added and stirred at room temperature for 1 hour. Saturated sodium hydrogencarbonate aqueous solution was added and extracted with ethyl acetate. The organic layer was washed with saturated salt solution dried with magnesium sulfate, and the solvent was removed. The resulting crude product was dissolved in 10 mL of tetrahydrofuran, and under an atmosphere of nitrogen, at 0° C., 2.29 mL of methylmagnesium bromide was added. After stirring at 0° C. for 40 minutes diluted hydrochloric acid solution was added and extracted with ethyl acetate. The organic layer was washed with saturated salt water and dried with magnesium sulfate. The solvent was removed under vacuum and the purification through silica gel column chromatography resulted in 190 mg (Yield: 65%) of the title compound.

1H-NMR (270 MHz, CDCl$_3$): δ 1.0~1.3 (m, 2H), 1.46 (s, 9H), 1.72~2.0 (m, 3H), 2.09 (s, 3H), 2.56 (td, 1H, J=12.8, 2.9 Hz), 3.06 (td , 1H, J=13.2, 2.0 Hz), 3.2~3.5 (m, 2H), 3.83 (brd, 1H, J=13.5 Hz), 4.65 (s, 2H), 4.5~4.7 (m, 1H), 7.60 (t, 1H J=7.9 Hz), 7.6~7.8 (m, 1H), 7.70 (s, 1H), 7.85 (d, 1H, J=7.9 Hz), 7.90 (s, 1H), 8.02 (s, 1H), 8.16 (s, 1H).

EXAMPLE 1

Methyl 3-(3-Amidinophenyl)-5-[(4-piperidinyl)methoxymehthyl]-benzoate.salt

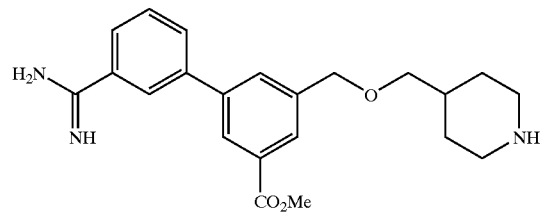

6.0 g of the compound of the Productive Example 9 was dissolved in 60 mL of dichloromethane and 3.0 mL of methanol was added. The gas of hydrochloric acid was bubbled into the solution with stirring under ice-cooling. After stirring at 0° C. for 30 minutes and then at room temperature for 20 hours, it was concentrated to a dry solid. 30 mL of saturated ammonia-ethanol solution was added, stirred at room temperature for 5 hours, and concentrated. The resulting crude product was purified using HP-20 column chromatography (30 g, Eluent: water-methanol) to produce the title compound (4.89 g, Yield: 99%).

1H-NMR (270 MHz DMSO-d$_6$): δ 1.3 1.5 (m, 2H), 1.7 2.0 (m, 3H), 2.7 2.9 (m, 2H), 3.2 3.3 (m, 2H), 3.38 (d, 2H, J=6.3 Hz), 3.91 (s, 3H), 4.64 (s, 2H), 7.69 (t, 1H , J=7.9 Hz), 7.86 (d, 1H , J=7.9 Hz), 7.99 (s, 1H), 8.02 (s, 1H), 8.07 (d, 1H, J=7.6 Hz), 8.15 (s, 1H), 8.28 (s, 1H), 8.55& 8.85 (brs, 1H), 9.19 & 9.52 (s, 2H).

According to the same reaction of the above Example 1 except that HPLC (ODS, Eluent: water-methanol) was used instead of HP-20 column chromatography for isolation and purification, the compounds of Example 2–40 which are listed in table 3 were synthesized.

EXAMPLE 41

Methyl 3-(3-Amidinophenyl)-5-[(1-acetoimidoyl-4-piperidinyl)methoxymethyl]benzoate.salt

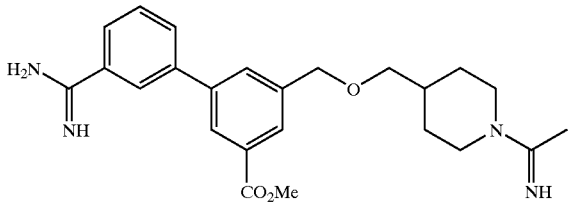

To 4.79 g of the compound of the Example 1 and 3.10 g of ethylacetoimidate.monohydrochloride, 50 mL of ethanol was added. 5.25 ml of triethylamine was dropped with stirring under ice-cooling. After increasing the temperature from 0° C. to room temperature, stirring was continued for 36 hours and the product was concentrated to form a dry solid. The purification with HPLC (ODS, Eluent: water-methanol) resulted in the title compound (4.37 g, Yield: 82%).

1H-NMR (270 MHz, DMSO-$d_6$): δ 1.1~1.4 (m, 2H), 1.7~2.1 (m, 3H), 2.50 (s, 3H), 3.0~3.5 (m, 4H), 3.8~4.0 (m, 1H), 3.91 (s, 3H), 4.0~4.2 (m, 1H), 4.64 (s, 2H), 7.74 (t, 1H, J=7.8 Hz), 7.87 (d, 1H, J=7.6 Hz), 8.00 (s, 1H), 8.03 (s, 1H), 8.07 (d, 1H, J=7.6 Hz), 8.16 (s, 1H), 8.28(s, 1H), 8.64 & 9.20 (brs, 1H), 9.25 & 9.54 (brs, 2H).

According to the same reaction of the above Example 41, the compounds of Example 42–57 which are listed in table 3 were synthesized.

Further, using the same reaction as above except for using ethyl propioneimidate.monohydrochloride instead of ethylacetoimidate-monohydrochloride, the compounds of Examples 58–59 which are listed in table 3 were synthesized.

Further, using the same reaction as above except for using ethyl hydroxyacetoimidate.monohydrochloride instead of ethylacetoimidate.monohydrochloride, the compounds of Example 60 which are listed in table 3 were synthesized.

EXAMPLE 61

3-(3-Amidinophenyl)-5-[(1-acetoimidoyl-4-piperidinyl)methoxymethyl]benzoic Acid.hydrochloride

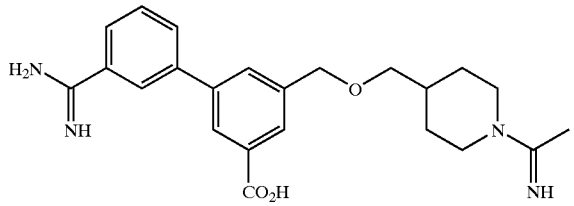

2.71 g of the compound of the Example 41 was dissolved in 27 ml of 2N hydrochloric acid, stirred at 70° C. for 24 hours, concentrated to form a dry solid, and isolated and purified using HPLC (ODS, Eluent: water-methanol) to produce the title compound (2.00 g, Yield: 76%).

1H-NMR (270 MHz DMSO-$d_6$): δ 1.2~1.6 (m, 2H), 1.9~2.2 (m, 3H), 2.31 (s, 3H), 3.0~3.4 (m, 2H), 3.47 (d, 2H, J=5.9 Hz), 3.9~4.1 (m, 2H), 4.65 (s, 2H), 7.6~7.8 (m, 3H), 8.0~8.1 (m, 2H), 8.10 (s, 1H), 8.24 (s, 1H).

According to the same reaction of the above Example 61, the compounds of Examples 62–68, 70 and 72–83 which are listed in table 3 were synthesized.

EXAMPLE 69

3-(3-Amidinophenyl)-5-[[(4-piperidyl)methyl] aminomethyl]phenylcarbonylaminoacetic Acid.salt

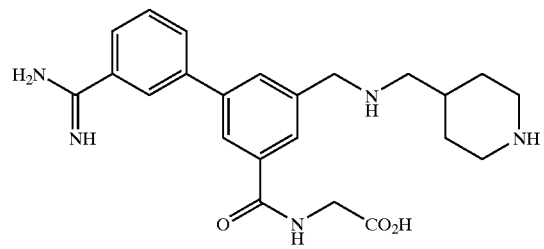

73 mg of the compound of the Example 68 was dissolved in 5 mL of DMF, and to this solution, 38 mg of 1-(3-dimethylaminopropyl)-3-ethylcarbodiimide hydrochloride, 20 mg of glycine, and 50 mg of triethylamine were added and stirred at room temperature, overnight. The solvent was removed and the isolation and purification using HPLC (ODS, Eluent: water-methanol) results in the title compound (25 mg, Yield: 30%).

According to the same reaction of the above Example 69, the compounds of Example 71 which are listed in table 3 were synthesized.

EXPERIMENT 1

(1) Determination of Inhibiting Activity of Activated Blood Coagulation Factor X (FXa):

The substance for analysis was dissolved in water or water wherein a suitable concentration of organic solvents (DMSO ethanol or .methanol) had been added, as a specimen. To 70 μL of the specimen serially diluted with water, 90 μL of 100 mM Tris buffer (pH 8.4), 20 μL of 50 mM Tris buffer (pH 8.4) containing 50 mU/mL human FXa, and 2 mM substrate (Daiichi Chemical S-2765) were added and incubated for 30 min., 50 μL of 50% acetic acid was added, and the absorbance (A405) were determined. As a blank, Tris buffer was added instead of FXa while, as a control, water was added instead of the specimen. The 50% inhibition activity (IC50) was determined as the indication of FXa inhibiting activity. The inhibiting activity of human FXa by the present compound was listed in table, 4.

(2) Determination of Thrombin Inhibiting Activity:

To 70 μL of the specimen serially diluted with water, 90 μL of 100 mM Tris buffer (pH 8.4), 20 μL of 50 mM Tris buffer (pH 8.4) containing 1 U/mL human thrombin, and 2 mM substrate (Daiichi Chemical S-2238) were added and incubated for 30 min., 50μL of 50% acetic acid was added, and the absorbance (A405) were determined. As, a blank, Tris buffer was added instead of thrombin while as a control, water is added instead of the specimen. The 50% inhibition activity ($IC_{50}$) was determined as the indication of thrombin inhibiting activity. The inhibiting activity of human thrombin by the present compound is listed in table 4.

(3) Determination of Anticoagulation Activity (APTT):

To 100 μL of normal human plasma (Ci-Trol®) manufactured by DADE, 100 μL of the specimen was added, and incubated at 37° C. for 1 minute. To this solution, 100 μL of APTT reagent (manufactured by DADE) which was, retained at 37° C. was added, and after incubating at 37° C. for 2 minutes, 100 μL of 25 mM calcium chloride solution was added, and the coagulation time was determined using the coagulation measurement apparatus manufactured by AMELUNG. The coagulation time when physiological salt solution was added instead of the analyte is used as a control, the concentration of the specimen corresponding to the 2-fold elongation of this coagulation time (CT2) is calculated, and this value is used as, the indication of the anticoagulation activity. The human APTT elongation activities of the present compounds were listed in table 4.

(4) Determination of Acetylcholine Esterase (AChE) Inhibiting Activity

The substance for analysis was dissolved in distilled water as specimen. To 50 μL of the specimen serially diluted, 50 μL of enzyme solution, wherein human acetylcholine esterase (manufactured by Sigma, C-5400) had been dissolved in distilled water at 0.1 U/mL was added. To this solution, 50 μL of the solution which was prepared by dissolving 5,5'-dithiobis (manufactured by Nacarai Tesque, 141-01) in phosphate buffer (0.1M $NaH_2PO_4$—$Na_2HPO_4$, pH 7.0) at 0.5 mM is,added and mixed, and reacted with 50 μL of the solution wherein acetylthiocholine iodide (Wako Company, 017-09313) had been dissolved in phosphate buffer at 3 mM, at room temperature. As a control distilled water was added instead of the substance for analysis and the absorbance (A450) was determined over time. As a blank, phosphate buffer was added instead of the enzyme solution and the 50% inhibition activity (IC50),was determined.

The human AChE inhibiting activity of the present compound was listed in table 4.

(5) Determination of Bioavailability (BA):

The substance for analysis was dissolved in distilled water (for oral administration; 10 mg/kg) or physiological salt solution (for intravenous administration; 3 mg/kg) to prepare a solution for administration. This solution was administered to fasted ICR mice (male, 6 weeks aged), the whole blood was extracted from the heart under ether anesthesia at 5 min. (intravenous administration group only), 15 min., 30 min., 1 hr., 2 hr. and 4 hr. after the administration, and the plasma was separated by the centrifugation (3,500 rpm, 30 min., 4° C.) to produce the specimen (n=4). Using the above method for determining FXa inhibiting activity, the calibration curve for the substance for analysis was previously prepared and the concentration of the substance for analysis in the specimen was determined. The lower area of the concentration in plasma—time curve (AUC) was calculated and then the bioavailavility in the mouse (BA) was calculated according to the following formula:

$$BA(\%) = (AUC\ po)/(AUC\ iv) \times (Dose\ iv)/(Dose\ po) \times 100$$

The bioavailability for the compound of the invention in the mouse was listed in table 4.

Industrial Applicability

A biphenylamidine derivative, and pharmaceutically acceptable salt thereof, of the invention have an effect of inhibiting FXa activity, and can be used as a prophylactic agent and/or a therapeutic agent which are clinically applicable against thromboembolisms such as myocardial infarction, cerebral thrombosis, thrombosis of peripheral arteries or thrombosis of deep veins as a FXa inhibitor.

TABLE 1

| Compound No. | L | $R^2$ | X | n | Y |
|---|---|---|---|---|---|
| 1 | Bond | —$CO_2Me$ | —NH— | 1 | cyclopentyl |
| 2 | Bond | —$CO_2Me$ | —NH— | 1 | cyclohexyl |
| 3 | Bond | —$CO_2Me$ | —NH— | 1 | cyclohexyl-$CONH_2$ |
| 4 | Bond | —$CO_2Me$ | —NH— | 1 | cyclohexyl-$CO_2Me$ |
| 5 | Bond | —$CO_2Me$ | —NH— | 1 | cyclohexyl-$CO_2H$ |

TABLE 1-continued
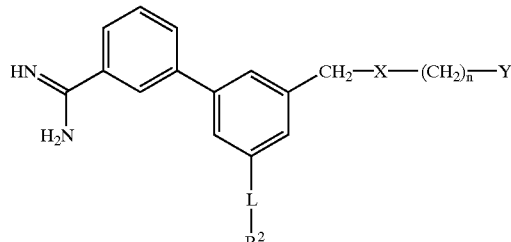
| Compound No. | L | R² | X | n | Y |
|---|---|---|---|---|---|
| 6 | Bond | —CO₂Me | —NH— | 1 | 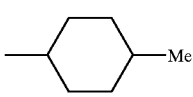 |
| 7 | Bond | —CO₂Me | —NH— | 1 | 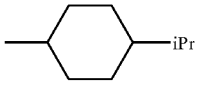 |
| 8 | Bond | —CO₂Me | —NH— | 1 | 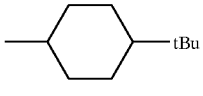 |
| 9 | Bond | —CO₂Me | —NH— | 1 | 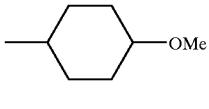 |
| 10 | Bond | —CO₂Me | —NH— | 1 | 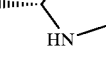 |
| 11 | Bond | —CO₂Me | —NH— | 1 | 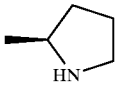 |
| 12 | Bond | —CO₂Me | —NH— | 1 | 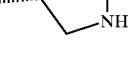 |
| 13 | Bond | —CO₂Me | —NH— | 1 | 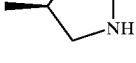 |
| 14 | Bond | —CO₂Me | —NH— | 1 | 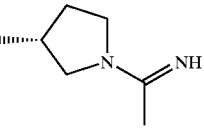 |
| 15 | Bond | —CO₂Me | —NH— | 1 | 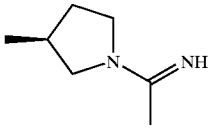 |
| 16 | Bond | —CO₂Me | —NH— | 1 | 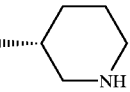 |

TABLE 1-continued
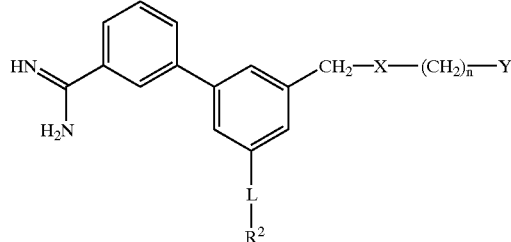
| Compound No. | L | R² | X | n | Y |
|---|---|---|---|---|---|
| 17 | Bond | —CO₂Me | —NH— | 1 | 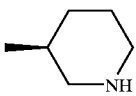 |
| 18 | Bond | —CO₂Me | —NH— | 1 | 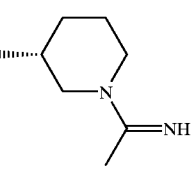 |
| 19 | Bond | —CO₂Me | —NH— | 1 | 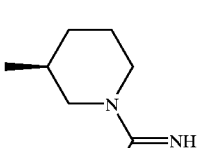 |
| 20 | Bond | —CO₂Me | —NH— | 1 | 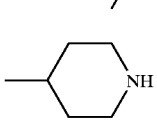 |
| 21 | Bond | —CO₂Me | —NH— | 1 | 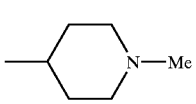 |
| 22 | Bond | —CO₂Me | —NH— | 1 | 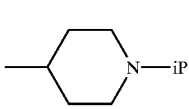 |
| 23 | Bond | —CO₂Me | —NH— | 1 | 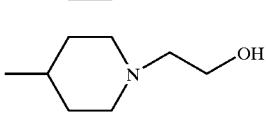 |
| 24 | Bond | —CO₂Me | —NH— | 1 | 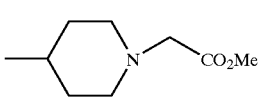 |
| 25 | Bond | —CO₂Me | —NH— | 1 | 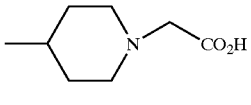 |
| 26 | Bond | —CO₂Me | —NH— | 1 | 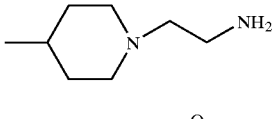 |
| 27 | Bond | —CO₂Me | —NH— | 1 | 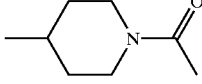 |

TABLE 1-continued

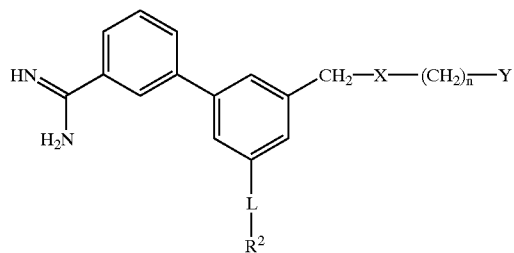

| Compound No. | L | R² | X | n | Y |
|---|---|---|---|---|---|
| 28 | Bond | —CO₂Me | —NH— | 1 | piperidine-N-C(=O)-CH₂CH₃ |
| 29 | Bond | —CO₂Me | —NH— | 1 | piperidine-N-C(=NH)-NH₂ |
| 30 | Bond | —CO₂Me | —NH— | 1 | piperidine-N-C(=NH)-CH₃ |
| 31 | Bond | —CO₂Me | —NH— | 1 | piperidine-N-C(=NH)-CH₂CH₃ |
| 32 | Bond | —CO₂Me | —NH— | 1 | piperidine-N-C(=NH)-CH₂OH |
| 33 | Bond | —CO₂Me | —NH— | 1 | piperidine-N-C(=NH)-CH₂CH₂OH |
| 34 | Bond | —CO₂H | —NH— | 1 | cyclopentyl |
| 35 | Bond | —CO₂H | —NH— | 1 | cyclohexyl |
| 36 | Bond | —CO₂H | —NH— | 1 | 4-(CO₂H)-cyclohexyl |
| 37 | Bond | —CO₂H | —NH— | 1 | 4-Me-cyclohexyl |
| 38 | Bond | —CO₂H | —NH— | 1 | 4-iPr-cyclohexyl |
| 39 | Bond | —CO₂H | —NH— | 1 | 4-tBu-cyclohexyl |

TABLE 1-continued
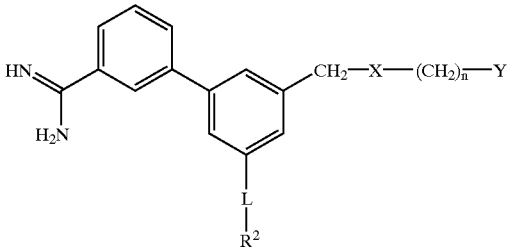
| Compound No. | L | R² | X | n | Y |
|---|---|---|---|---|---|
| 40 | Bond | —CO₂H | —NH— | 1 | 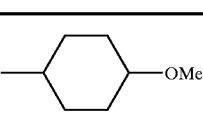 |
| 41 | Bond | —CO₂H | —NH— | 1 | 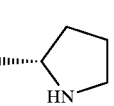 |
| 42 | Bond | —CO₂H | —NH— | 1 | 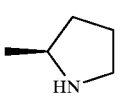 |
| 43 | Bond | —CO₂H | —NH— | 1 | 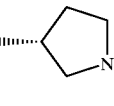 |
| 44 | Bond | —CO₂H | —NH— | 1 | 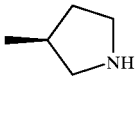 |
| 45 | Bond | —CO₂H | —NH— | 1 | 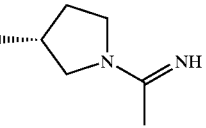 |
| 46 | Bond | —CO₂H | —NH— | 1 | 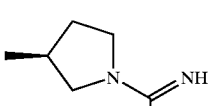 |
| 47 | Bond | —CO₂H | —NH— | 1 | 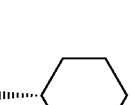 |
| 48 | Bond | —CO₂H | —NH— | 1 | 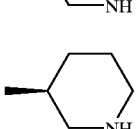 |
| 49 | Bond | —CO₂H | —NH— | 1 | 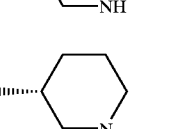 |

TABLE 1-continued
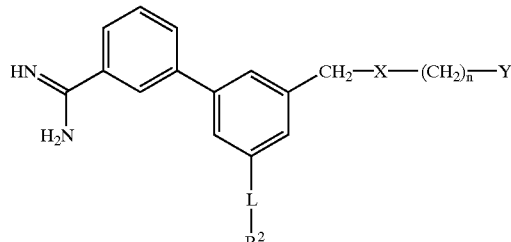
| Compound No. | L | R² | X | n | Y |
|---|---|---|---|---|---|
| 50 | Bond | —CO₂H | —NH— | 1 | 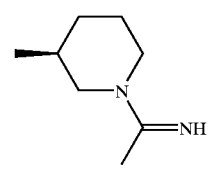 |
| 51 | Bond | —CO₂H | —NH— | 1 | 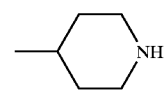 |
| 52 | Bond | —CO₂H | —NH— | 1 | 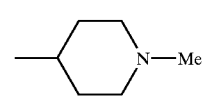 |
| 53 | Bond | —CO₂H | —NH— | 1 | 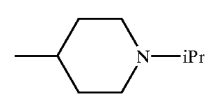 |
| 54 | Bond | —CO₂H | —NH— | 1 | 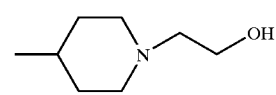 |
| 55 | Bond | —CO₂H | —NH— | 1 | 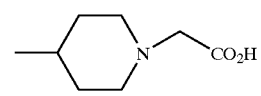 |
| 56 | Bond | —CO₂H | —NH— | 1 | 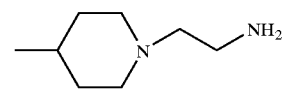 |
| 57 | Bond | —CO₂H | —NH— | 1 | 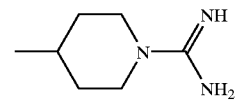 |
| 58 | Bond | —CO₂H | —NH— | 1 | 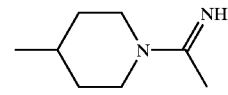 |
| 59 | Bond | —CO₂H | —NH— | 1 | 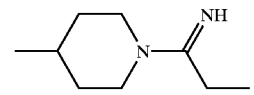 |
| 60 | Bond | —CO₂H | —NH— | 1 | 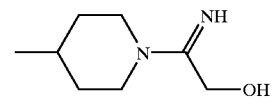 |

TABLE 1-continued
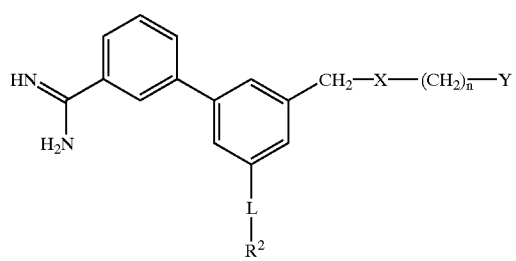
| Compound No. | L | R² | X | n | Y |
|---|---|---|---|---|---|
| 61 | Bond | —CO₂H | —NH— | 1 | 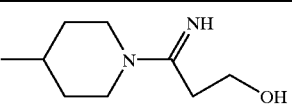 |
| 62 | Bond | —CO₂Me | —O— | 1 | 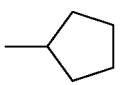 |
| 63 | Bond | —CO₂Me | —O— | 1 | 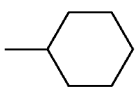 |
| 64 | Bond | —CO₂Me | —O— | 1 | 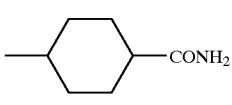 |
| 65 | Bond | —CO₂Me | —O— | 1 | 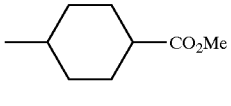 |
| 66 | Bond | —CO₂Me | —O— | 1 | 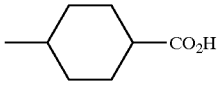 |
| 67 | Bond | —CO₂Me | —O— | 1 | 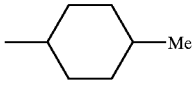 |
| 68 | Bond | —CO₂Me | —O— | 1 |  |
| 69 | Bond | —CO₂Me | —O— | 1 | 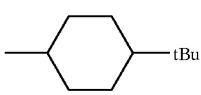 |
| 70 | Bond | —CO₂Me | —O— | 1 | 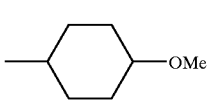 |
| 71 | Bond | —CO₂Me | —O— | 1 | 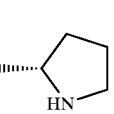 |
| 72 | Bond | —CO₂Me | —O— | 1 | 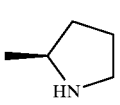 |

TABLE 1-continued
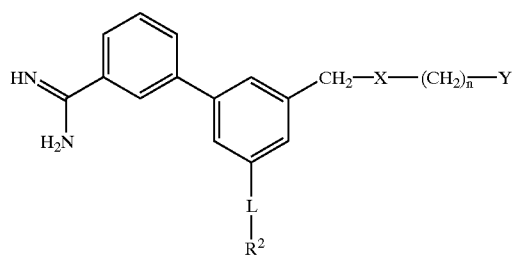
| Compound No. | L | R² | X | n | Y |
|---|---|---|---|---|---|
| 73 | Bond | —CO₂Me | —O— | 1 | 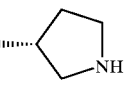 |
| 74 | Bond | —CO₂Me | —O— | 1 | 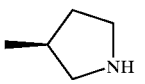 |
| 75 | Bond | —CO₂Me | —O— | 1 | 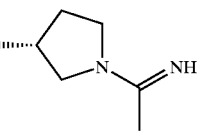 |
| 76 | Bond | —CO₂Me | —O— | 1 | 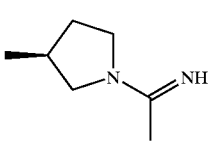 |
| 77 | Bond | —CO₂Me | —O— | 1 | 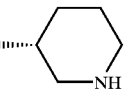 |
| 78 | Bond | —CO₂Me | —O— | 1 | 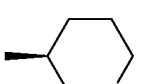 |
| 79 | Bond | —CO₂Me | —O— | 1 | 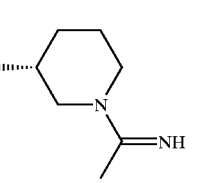 |
| 80 | Bond | —CO₂Me | —O— | 1 | 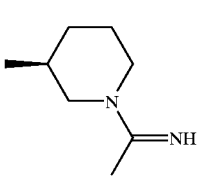 |
| 81 | Bond | —CO₂Me | —O— | 1 | 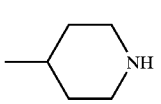 |
| 82 | Bond | —CO₂Me | —O— | 1 | 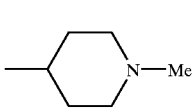 |

TABLE 1-continued

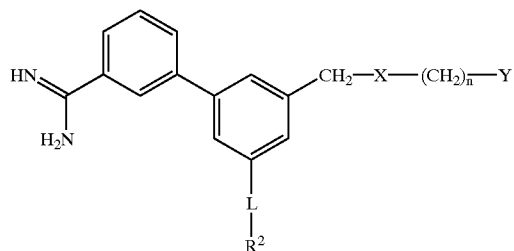

| Compound No. | L | R² | X | n | Y |
|---|---|---|---|---|---|
| 83 | Bond | —CO₂Me | —O— | 1 | piperidine-N-iPr |
| 84 | Bond | —CO₂Me | —O— | 1 | piperidine-N-CH₂CH₂OH |
| 85 | Bond | —CO₂Me | —O— | 1 | piperidine-N-CH₂CO₂Me |
| 86 | Bond | —CO₂Me | —O— | 1 | piperidine-N-CH₂CO₂H |
| 87 | Bond | —CO₂Me | —O— | 1 | piperidine-N-CH₂CH₂NH₂ |
| 88 | Bond | —CO₂Me | —O— | 1 | piperidine-N-C(=O)CH₃ |
| 89 | Bond | —CO₂Me | —O— | 1 | piperidine-N-C(=O)CH₂CH₃ |
| 90 | Bond | —CO₂Me | —O— | 1 | piperidine-N-C(=NH)NH₂ |
| 91 | Bond | —CO₂Me | —O— | 1 | piperidine-N-C(=NH)CH₃ |
| 92 | Bond | —CO₂Me | —O— | 1 | piperidine-N-C(=NH)CH₂CH₃ |
| 93 | Bond | —CO₂Me | —O— | 1 | piperidine-N-C(=NH)CH₂OH |
| 94 | Bond | —CO₂Me | —O— | 1 | piperidine-N-C(=NH)CH₂CH₂OH |

TABLE 1-continued

| Compound No. | L | R² | X | n | Y |
|---|---|---|---|---|---|
| 95 | Bond | —CO₂H | —O— | 1 | cyclopentyl |
| 96 | Bond | —CO₂H | —O— | 1 | cyclohexyl |
| 97 | Bond | —CO₂H | —O— | 1 | 4-CO₂H-cyclohexyl |
| 98 | Bond | —CO₂H | —O— | 1 | 4-Me-cyclohexyl |
| 99 | Bond | —CO₂H | —O— | 1 | 4-iPr-cyclohexyl |
| 100 | Bond | —CO₂H | —O— | 1 | 4-tBu-cyclohexyl |
| 101 | Bond | —CO₂H | —O— | 1 | 4-OMe-cyclohexyl |
| 102 | Bond | —CO₂H | —O— | 1 | (2S)-pyrrolidinyl |
| 103 | Bond | —CO₂H | —O— | 1 | (2R)-pyrrolidinyl |
| 104 | Bond | —CO₂H | —O— | 1 | (3S)-pyrrolidinyl |
| 105 | Bond | —CO₂H | —O— | 1 | (3R)-pyrrolidinyl |
| 106 | Bond | —CO₂H | —O— | 1 | (3S)-N-acetimidoyl-pyrrolidinyl |

TABLE 1-continued
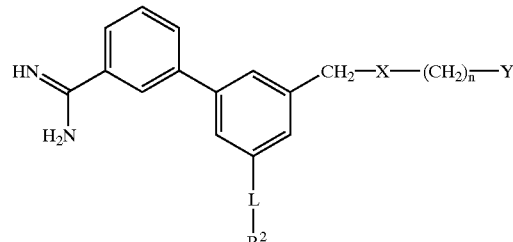
| Compound No. | L | R² | X | n | Y |
|---|---|---|---|---|---|
| 107 | Bond | —CO₂H | —O— | 1 | 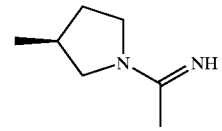 |
| 108 | Bond | —CO₂H | —O— | 1 | 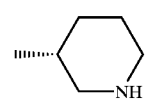 |
| 109 | Bond | —CO₂H | —O— | 1 | 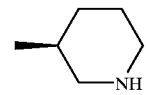 |
| 110 | Bond | —CO₂H | —O— | 1 | 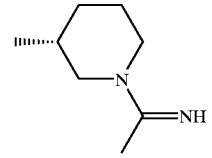 |
| 111 | Bond | —CO₂H | —O— | 1 | 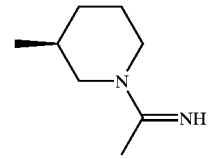 |
| 112 | Bond | —CO₂H | —O— | 1 | 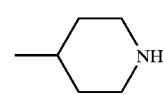 |
| 113 | Bond | —CO₂H | —O— | 1 | 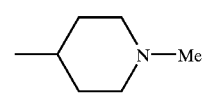 |
| 114 | Bond | —CO₂H | —O— | 1 | 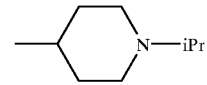 |
| 115 | Bond | —CO₂H | —O— | 1 | 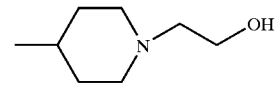 |
| 116 | Bond | —CO₂H | —O— | 1 | 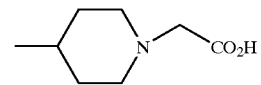 |

TABLE 1-continued
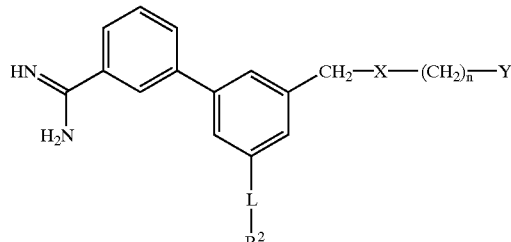
| Compound No. | L | R² | X | n | Y |
|---|---|---|---|---|---|
| 117 | Bond | —CO₂H | —O— | 1 | 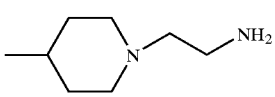 |
| 118 | Bond | —CO₂H | —O— | 1 | 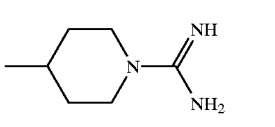 |
| 119 | Bond | —CO₂H | —O— | 1 | 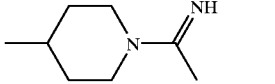 |
| 120 | Bond | —CO₂H | —O— | 1 | 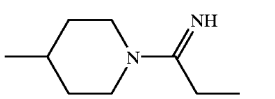 |
| 121 | Bond | —CO₂H | —O— | 1 | 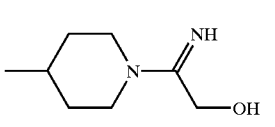 |
| 122 | Bond | —CO₂H | —O— | 1 | 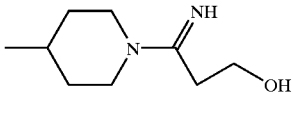 |
| 123 | Bond |  | —NH— | 1 | 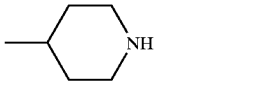 |
| 124 | Bond |  | —NH— | 1 | 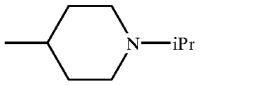 |
| 125 | Bond |  | —NH— | 1 | 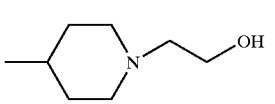 |
| 126 | Bond |  | —NH— | 1 | 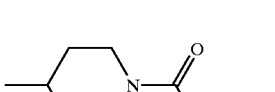 |
| 127 | Bond |  | —NH— | 1 |  |

TABLE 1-continued

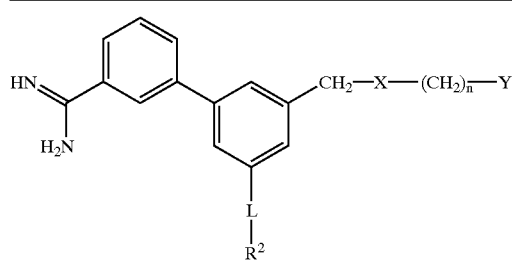

| Compound No. | L | R² | X | n | Y |
|---|---|---|---|---|---|
| 128 | Bond | COMe | —NH— | 1 | piperidine-N-C(=NH)NH₂ |
| 129 | Bond | COMe | —NH— | 1 | piperidine-N-C(=NH)Me |
| 130 | Bond | COMe | —NH— | 1 | piperidine-N-C(=NH)Et |
| 131 | Bond | COMe | —NH— | 1 | piperidine-N-C(=NH)CH₂OH |
| 132 | Bond | COMe | —O— | 1 | piperidine-NH |
| 133 | Bond | COMe | —O— | 1 | piperidine-N-iPr |
| 134 | Bond | COMe | —O— | 1 | piperidine-N-CH₂CH₂OH |
| 135 | Bond | COMe | —O— | 1 | piperidine-N-C(=O)Me |
| 136 | Bond | COMe | —O— | 1 | piperidine-N-C(=O)Et |
| 137 | Bond | COMe | —O— | 1 | piperidine-N-C(=NH)NH₂ |
| 138 | Bond | COMe | —O— | 1 | piperidine-N-C(=NH)Me |

TABLE 1-continued

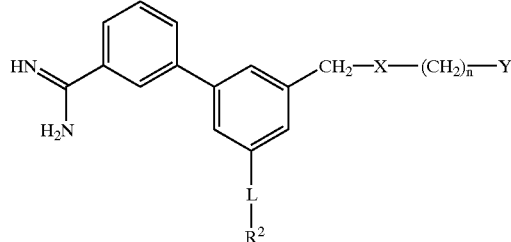

| Compound No. | L | R² | X | n | Y |
|---|---|---|---|---|---|
| 139 | Bond |  C(O)Me | —O— | 1 | 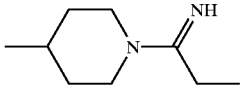 piperidine-N-C(=NH)Et |
| 140 | Bond |  C(O)NH₂ | —O— | 1 | 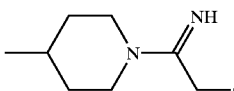 piperidine-N-C(=NH)CH₂OH |
| 141 | Bond |  C(O)NH₂ | —NH— | 1 | 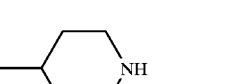 piperidine-NH |
| 142 | Bond |  C(O)NH₂ | —NH— | 1 | 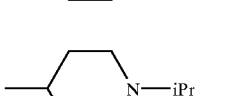 piperidine-N-iPr |
| 143 | Bond |  C(O)NH₂ | —NH— | 1 | 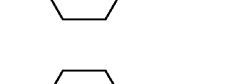 piperidine-N-CH₂CH₂OH |
| 144 | Bond |  C(O)NH₂ | —NH— | 1 | 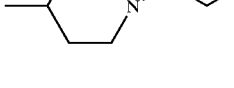 piperidine-N-C(O)Me |
| 145 | Bond |  C(O)NH₂ | —NH— | 1 | 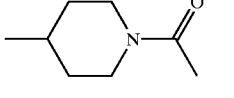 piperidine-N-C(O)Et |
| 146 | Bond |  C(O)NH₂ | —NH— | 1 | 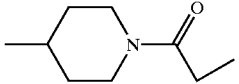 piperidine-N-C(=NH)NH₂ |
| 147 | Bond |  C(O)NH₂ | —NH— | 1 | 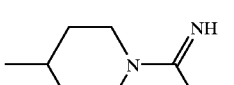 piperidine-N-C(=NH)Me |
| 148 | Bond |  C(O)NH₂ | —NH— | 1 | 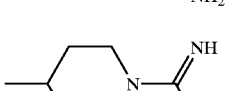 piperidine-N-C(=NH)Et |
| 149 | Bond |  C(O)NH₂ | —NH— | 1 | 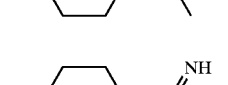 piperidine-N-C(=NH)CH₂OH |

TABLE 1-continued
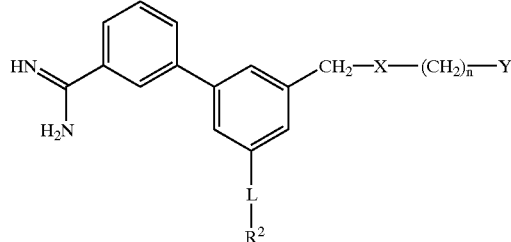
| Compound No. | L | R² | X | n | Y |
| --- | --- | --- | --- | --- | --- |
| 150 | Bond |  | —O— | 1 | 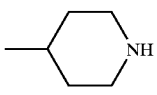 |
| 151 | Bond |  | —O— | 1 | 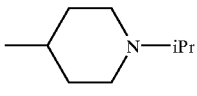 |
| 152 | Bond |  | —O— | 1 | 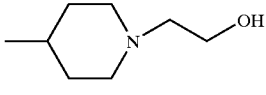 |
| 153 | Bond |  | —O— | 1 | 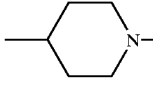 |
| 154 | Bond |  | —O— | 1 | 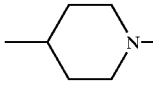 |
| 155 | Bond |  | —O— | 1 | 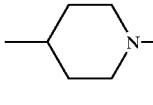 |
| 156 | Bond |  | —O— | 1 | 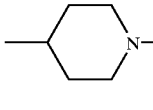 |
| 157 | Bond |  | —O— | 1 | 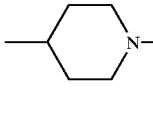 |
| 158 | Bond |  | —O— | 1 | 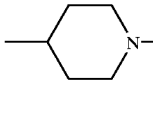 |
| 159 | Bond |  | —O— | 1 | 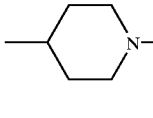 |
| 160 | Bond | 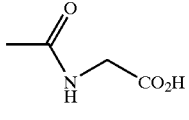 | —NH— | 1 | 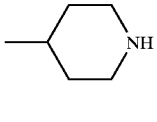 |

TABLE 1-continued
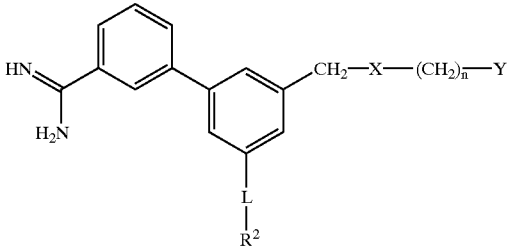
| Compound No. | L | R² | X | n | Y |
|---|---|---|---|---|---|
| 161 | Bond | 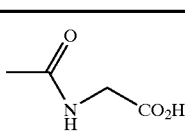 | —NH— | 1 | 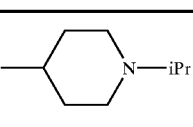 |
| 162 | Bond | 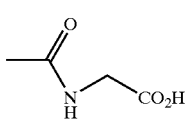 | —NH— | 1 | 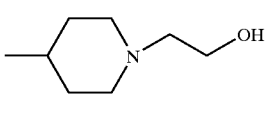 |
| 163 | Bond | 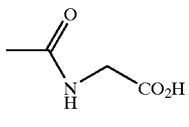 | —NH— | 1 | 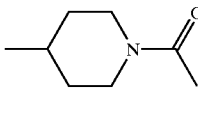 |
| 164 | Bond | 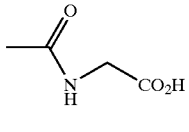 | —NH— | 1 | 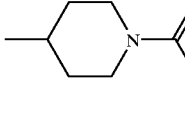 |
| 165 | Bond | 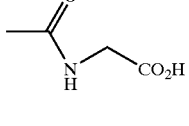 | —NH— | 1 | 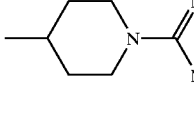 |
| 166 | Bond | 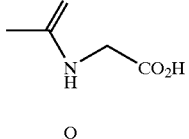 | —NH— | 1 | 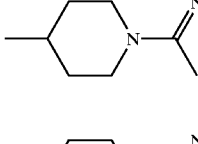 |
| 167 | Bond | 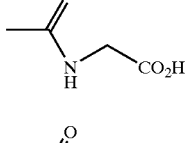 | —NH— | 1 | 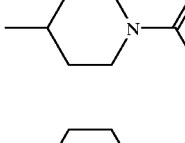 |
| 168 | Bond | 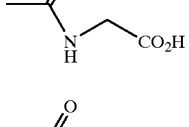 | —NH— | 1 | 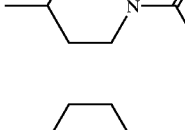 |
| 169 | Bond | 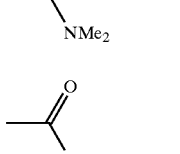 | —O— | 1 | 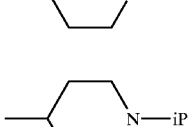 |
| 170 | Bond | 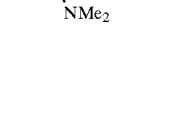 | —O— | 1 | 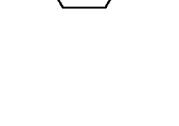 |

TABLE 1-continued
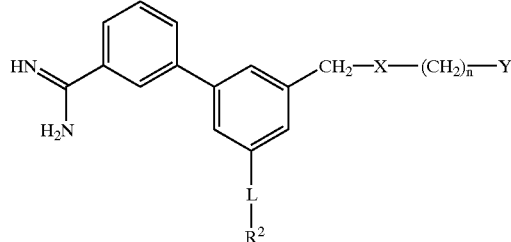
| Compound No. | L | R² | X | n | Y |
|---|---|---|---|---|---|
| 171 | Bond | 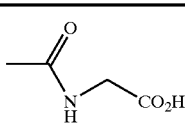 | —O— | 1 | 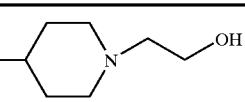 |
| 172 | Bond | 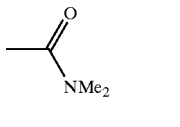 | —O— | 1 | 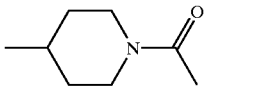 |
| 173 | Bond | 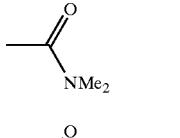 | —O— | 1 | 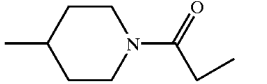 |
| 174 | Bond | 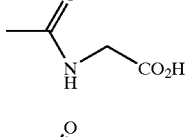 | —O— | 1 | 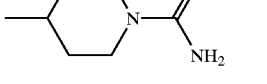 |
| 175 | Bond | 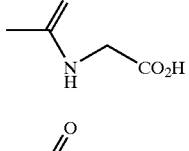 | —O— | 1 | 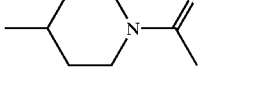 |
| 176 | Bond | 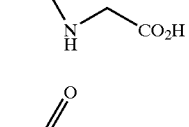 | —O— | 1 | 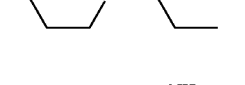 |
| 177 | Bond | 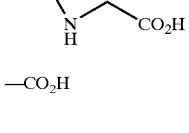 | —O— | 1 |  |
| 178 | Bond | —CO₂H | —O— | 0 | 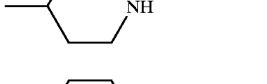 |
| 179 | Bond | —CO₂H | —O— | 0 | 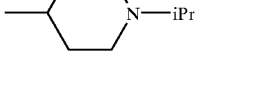 |
| 180 | Bond | —CO₂H | —O— | 0 | 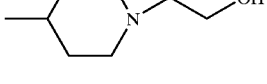 |
| 181 | Bond | —CO₂H | —O— | 0 | 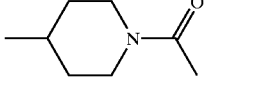 |

TABLE 1-continued

| Compound No. | L | R² | X | n | Y |
|---|---|---|---|---|---|
| 182 | Bond | —CO₂H | —O— | 0 | 4-(propanoyl)piperidin-1-yl |
| 183 | Bond | —CO₂H | —O— | 0 | 4-(carbamimidoyl)piperidin-1-yl |
| 184 | Bond | —CO₂H | —O— | 0 | 4-(1-iminoethyl)piperidin-1-yl |
| 185 | Bond | —CO₂H | —O— | 0 | 4-(1-iminopropyl)piperidin-1-yl |
| 186 | Bond | —CO₂H | —O— | 0 | 4-(2-hydroxy-1-iminoethyl)piperidin-1-yl |
| 187 | Bond | —CO₂H | —N(Me)— | 1 | piperidin-4-yl (NH) |
| 188 | Bond | —CO₂H | —N(Me)— | 1 | 1-methylpiperidin-4-yl |
| 189 | Bond | —CO₂H | —N(Me)— | 1 | 1-isopropylpiperidin-4-yl |
| 190 | Bond | —CO₂H | —N(Me)— | 1 | 1-(2-hydroxyethyl)piperidin-4-yl |
| 191 | Bond | —CO₂H | —N(Me)— | 1 | 1-(carboxymethyl)piperidin-4-yl |
| 192 | Bond | —CO₂H | —N(Me)— | 1 | 1-(2-aminoethyl)piperidin-4-yl |
| 193 | Bond | —CO₂H | —N(Me)— | 1 | 1-(carbamimidoyl)piperidin-4-yl |

TABLE 1-continued
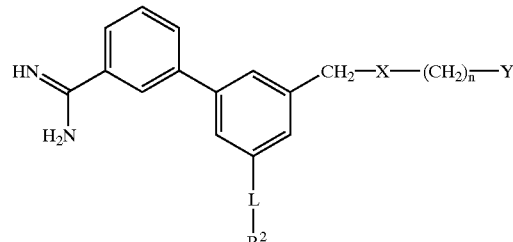
| Compound No. | L | R² | X | n | Y |
|---|---|---|---|---|---|
| 194 | Bond | —CO₂H | —N(Me)— | 1 | 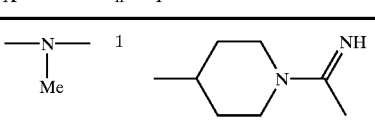 |
| 195 | Bond | —CO₂H | —N(Me)— | 1 | 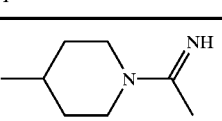 |
| 196 | Bond | —CO₂H | —N(Me)— | 1 | 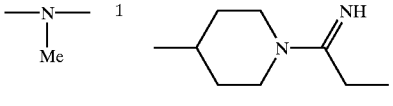 |
| 197 | Bond | —CO₂H | —N(Me)— | 1 | 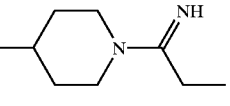 |
| 198 | Bond | —CO₂H | —N(CH₂CH₂OH)— | 1 | 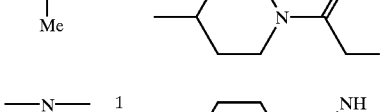 |
| 199 | Bond | —CO₂H | —N(CH₂CH₂OH)— | 1 | 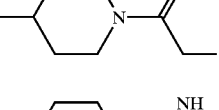 |
| 200 | Bond | —CO₂H | —N(CH₂CH₂OH)— | 1 | 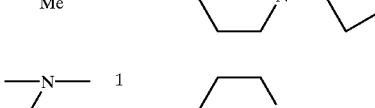 |
| 201 | Bond | —CO₂H | —N(CH₂CH₂OH)— | 1 | 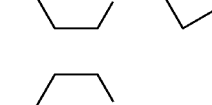 |
| 202 | Bond | —CO₂H | —N(CH₂CH₂OH)— | 1 | 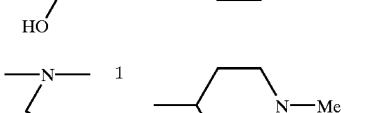 |
| 203 | Bond | —CO₂H | —N(CH₂CH₂OH)— | 1 | 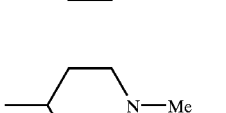 |

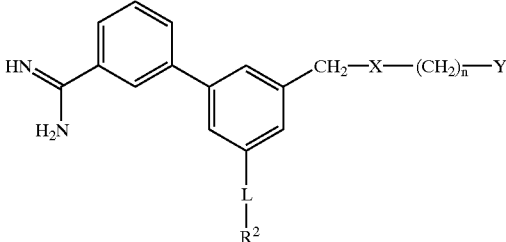

TABLE 1-continued

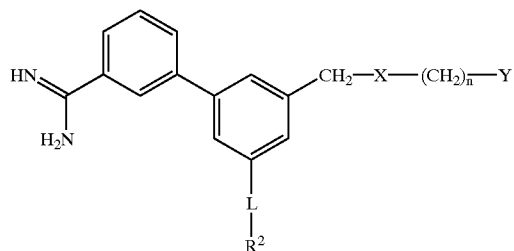

| Compound No. | L | R² | X | n | Y |
|---|---|---|---|---|---|
| 215 | Bond | —CO₂H | —N(C(O)CF₃)— | 1 | 4-(N-C(=NH)NH₂)-piperidinyl |
| 216 | Bond | —CO₂H | —N(C(O)CF₃)— | 1 | 4-(N-C(=NH)Me)-piperidinyl |
| 217 | Bond | —CO₂H | —N(SO₂Me)— | 1 | 4-(N-C(=NH)Et)-piperidinyl |
| 218 | Bond | —CO₂H | —N(SO₂Me)— | 1 | 4-(N-C(=NH)CH₂OH)-piperidinyl |
| 219 | Bond | —CO₂H | —N(SO₂Me)— | 1 | 4-(N-C(=NH)CH₂CH₂OH)-piperidinyl |
| 220 | —CH₂CH₂— | —CO₂H | —NH— | 1 | cyclopentyl |
| 221 | —CH₂CH₂— | —CO₂H | —NH— | 1 | cyclohexyl |
| 222 | —CH₂CH₂— | —CO₂H | —NH— | 1 | 4-CO₂H-cyclohexyl |
| 223 | —CH₂CH₂— | —CO₂H | —NH— | 1 | 4-Me-cyclohexyl |
| 224 | —CH₂CH₂— | —CO₂H | —NH— | 1 | 4-iPr-cyclohexyl |
| 225 | —CH₂CH₂— | —CO₂H | —NH— | 1 | 4-tBu-cyclohexyl |
| 226 | —CH₂CH₂— | —CO₂H | —NH— | 1 | 4-OMe-cyclohexyl |

TABLE 1-continued

| Compound No. | L | R² | X | n | Y |
|---|---|---|---|---|---|
| 227 | —CH₂CH₂— | —CO₂H | —NH— | 1 | (S)-pyrrolidin-2-yl (dashed wedge) |
| 228 | —CH₂CH₂— | —CO₂H | —NH— | 1 | (R)-pyrrolidin-2-yl (solid wedge) |
| 229 | —CH₂CH₂— | —CO₂H | —NH— | 1 | (S)-pyrrolidin-3-yl (dashed wedge) |
| 230 | —CH₂CH₂— | —CO₂H | —NH— | 1 | (R)-pyrrolidin-3-yl (solid wedge) |
| 231 | —CH₂CH₂— | —CO₂H | —NH— | 1 | (S)-1-(iminoethyl)pyrrolidin-3-yl (dashed wedge) |
| 232 | —CH₂CH₂— | —CO₂H | —NH— | 1 | (R)-1-(iminoethyl)pyrrolidin-3-yl (solid wedge) |
| 233 | —CH₂CH₂— | —CO₂H | —NH— | 1 | (S)-piperidin-3-yl (dashed wedge) |
| 234 | —CH₂CH₂— | —CO₂H | —NH— | 1 | (R)-piperidin-3-yl (solid wedge) |
| 235 | —CH₂CH₂— | —CO₂H | —NH— | 1 | (S)-1-(iminoethyl)piperidin-3-yl (dashed wedge) |
| 236 | —CH₂CH₂— | —CO₂H | —NH— | 1 | (R)-1-(iminoethyl)piperidin-3-yl (solid wedge) |

TABLE 1-continued
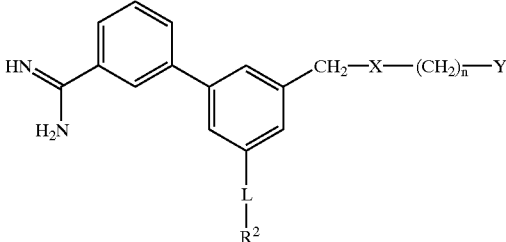
| Compound No. | L | R² | X | n | Y |
|---|---|---|---|---|---|
| 237 | —CH₂CH₂— | —CO₂H | —NH— | 1 | 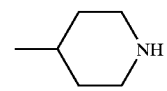 |
| 238 | —CH₂CH₂— | —CO₂H | —NH— | 1 | 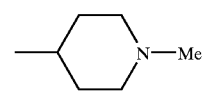 |
| 239 | —CH₂CH₂— | —CO₂H | —NH— | 1 | 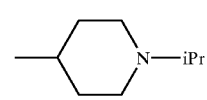 |
| 240 | —CH₂CH₂— | —CO₂H | —NH— | 1 | 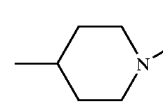 |
| 241 | —CH₂CH₂— | —CO₂H | —NH— | 1 | 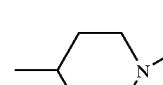 |
| 242 | —CH₂CH₂— | —CO₂H | —NH— | 1 | 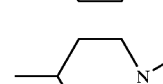 |
| 243 | —CH₂CH₂— | —CO₂H | —NH— | 1 | 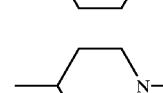 |
| 244 | —CH₂CH₂— | —CO₂H | —NH— | 1 | 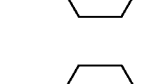 |
| 245 | —CH₂CH₂— | —CO₂H | —NH— | 1 | 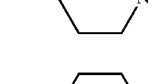 |
| 246 | —CH₂CH₂— | —CO₂H | —NH— | 1 | 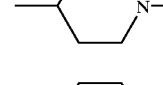 |
| 247 | —CH₂CH₂— | —CO₂H | —NH— | 1 | 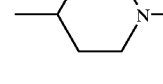 |
| 248 | Bond | —CO₂H | —NH— | 2 | 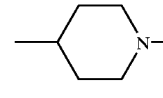 |

TABLE 1-continued
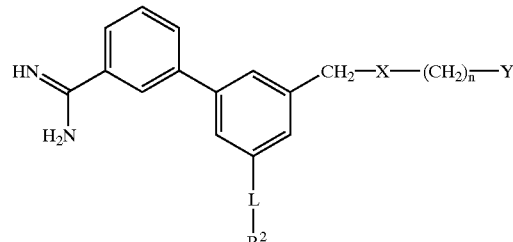
| Compound No. | L | R² | X | n | Y |
|---|---|---|---|---|---|
| 249 | Bond | 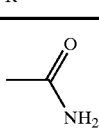 | —NH— | 2 | 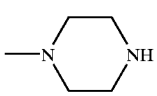 |
| 250 | Bond | —CO₂H | —NH— | 2 | 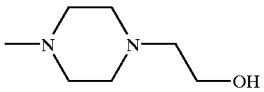 |
| 251 | Bond | 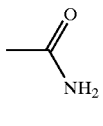 | —NH— | 2 | 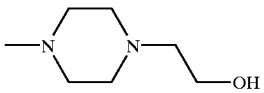 |
| 252 | Bond | —CO₂H | —NH— | 2 | 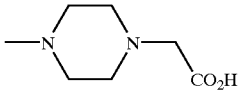 |
| 253 | Bond | 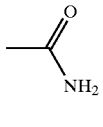 | —NH— | 2 | 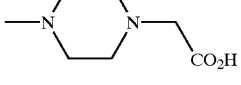 |
| 254 | Bond | —CO₂H | —NH— | 2 | 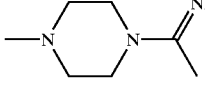 |
| 255 | —CH₂CH₂— | —CO₂H | —NH— | 2 | 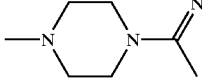 |
| 256 | Bond | 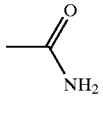 | —NH— | 2 | 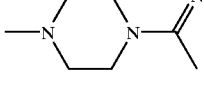 |
| 257 | Bond | —CO₂H | —NH— | 2 | 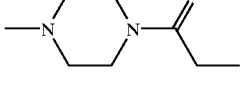 |
| 258 | Bond | —CO₂H | —NH— | 2 | 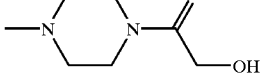 |
| 259 | —CH₂— | —CO₂H | —NH— | 1 | 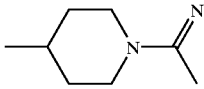 |

TABLE 1-continued
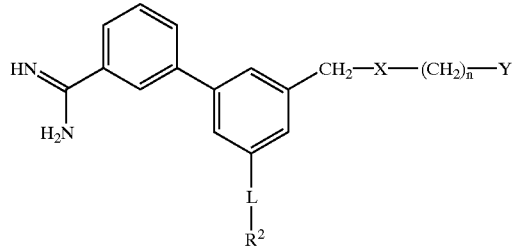
| Compound No. | L | R² | X | n | Y |
|---|---|---|---|---|---|
| 260 | —CH₂— | —CO₂H | —NH— | 1 | 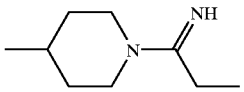 |
| 261 | —CH₂— | —CO₂H | —NH— | 1 | 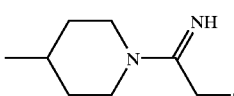 |
| 262 | Bond | —CO₂H | —NHCO— | 0 | 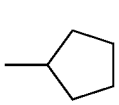 |
| 263 | Bond | —CO₂H | —NHCO— | 0 | 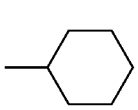 |
| 264 | Bond | —CO₂H | —NHCO— | 0 | 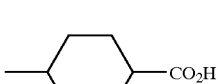 |
| 265 | Bond | —CO₂H | —NHCO— | 0 | 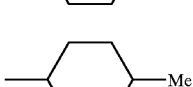 |
| 266 | Bond | —CO₂H | —NHCO— | 0 | 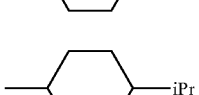 |
| 267 | Bond | —CO₂H | —NHCO— | 0 | 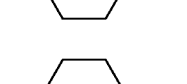 |
| 268 | Bond | —CO₂H | —NHCO— | 0 | 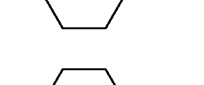 |
| 269 | Bond | —CO₂H | —NHCO— | 0 | 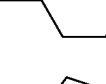 |
| 270 | Bond | —CO₂H | —NHCO— | 0 | 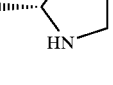 |
| 271 | Bond | —CO₂H | —NHCO— | 0 | 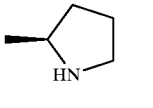 |

TABLE 1-continued
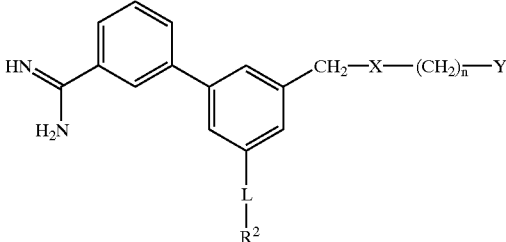
| Compound No. | L | R² | X | n | Y |
|---|---|---|---|---|---|
| 272 | Bond | —CO₂H | —NHCO— | 0 | 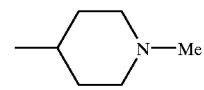 |
| 273 | Bond | —CO₂H | —NHCO— | 0 | 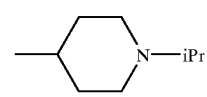 |
| 274 | Bond | —CO₂H | —NHCO— | 0 | 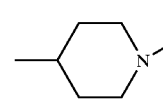 |
| 275 | Bond | —CO₂H | —NHCO— | 0 | 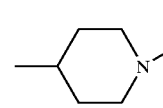 |
| 276 | Bond | —CO₂H | —NHCO— | 0 | 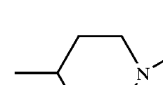 |
| 277 | Bond | —CO₂H | —NHCO— | 0 | 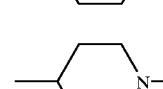 |
| 278 | Bond | —CO₂H | —NHCO— | 0 | 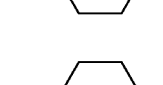 |
| 279 | Bond | —CO₂H | —NHCO— | 0 | 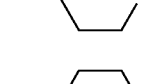 |
| 280 | Bond | —CO₂H | —NHCO— | 0 | 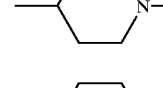 |
| 281 | Bond | —CO₂H | —NHCO— | 0 | 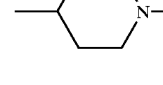 |
| 282 | Bond | —CO₂H | —NHCO— | 1 | 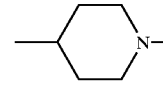 |
| 283 | Bond | —CO₂H | —NHCO— | 1 | 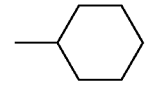 |

TABLE 1-continued
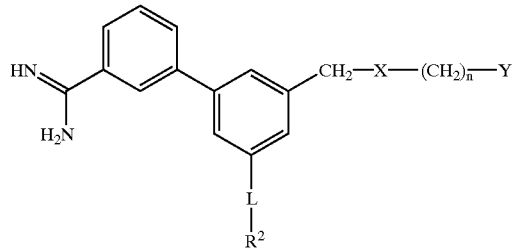
| Compound No. | L | R² | X | n | Y |
|---|---|---|---|---|---|
| 284 | Bond | —CO₂H | —NHCO— | 1 |  |
TABLE 2
| Production Example | Structure | Structural data |
|---|---|---|
| 4 | 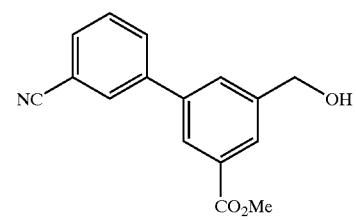 | ¹H-NMR(270MHz,CDCl₃)δ 2.1(brs, 1H), 3.96(s, 3H), 4.84(d, 2H, J=3.7Hz), 7.5–8.2(m, 7H). |
| 5 | 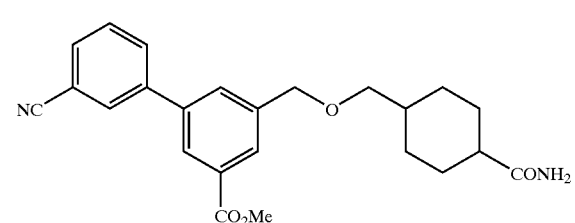 | ¹H-NMR(270MHz, CDCl₃)δ 0.9~1.2(m, 2H), 1.4~1.8(m, 4H), 1.9~2.2(m, 4 H), 3.36(d, 2H, J=6.3Hz), 3.97(s, 3H), 7.5~8.2(m, 7 H). |
| 6 | 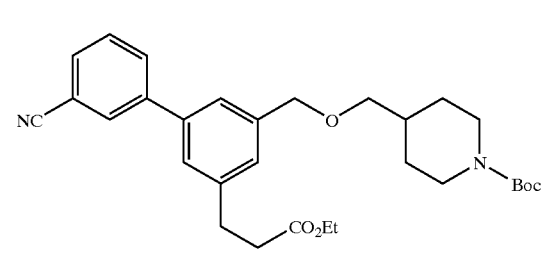 | ¹H-NMR(270MHz, CDCl₃)δ 1.0~1.3(m, 5H), 1.45(s, 9H), 1.7~1.9(m, 4H), 2.6~2.8(m, 4H), 3.03(t, 2H, J=7.6Hz), 3.36(d, 2H, J=6.3 Hz), 4.0~4.2(m, 3H), 4.53(s, 2H), 7.1~7.9(m, 7H). |
| 7 | 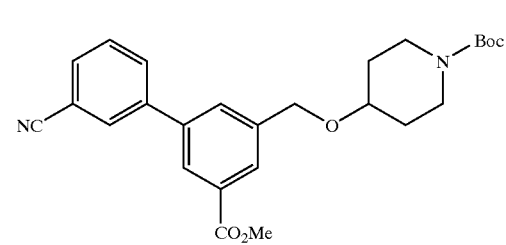 | ¹H-NMR(270MHz, CDCl₃)δ 1.46(s, 9H), 1.5~2.0(m, 4H), 3.0~3.2(m, 2H), 3.5~3.7(m, 1H), 3.7~3.9(m, 2 H), 3.97(s, 3H), 4.66(s, 2H), 7.5~8.2(m, 7H). |

TABLE 2-continued

| Production Example | Structure | Structural data |
|---|---|---|
| 8 | 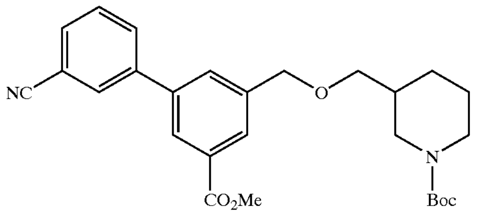 | ¹H-NMR(270MHz, CDCl₃)δ 1.44(s, 9H), 1.1~2.0(m, 5H), 2.6~3.0(m, 2H), 3.40(d, 2H, J=6.3Hz), 3.8~4.1(m, 2H), 3.97(s, 3H), 4.60(s, 2H), 7.5~8.2(m, 7H). |
| 9 | 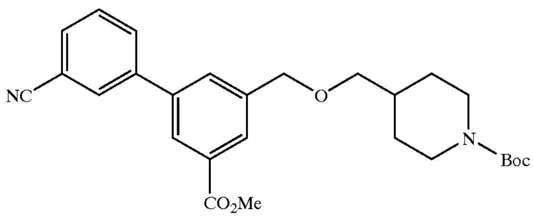 | ¹H-NMR(270MHz, CDCl₃)δ 1.0~1.3(m, 2H), 1.45(s, 9H), 1.5~1.6(m, 1H), 1.6~1.9(m, 2H), 2.71(t, 2H, J=12.2Hz), 3.38(d, 2H, J=5.9Hz), 3.97(s, 3H), 4.0~4.2(m, 2H), 4.60(s, 2H), 7.5~7.9(m, 4H), 7.90(s, 1H), 8.03(s, 1H), 8.16(s, 1H). |
| 10 | 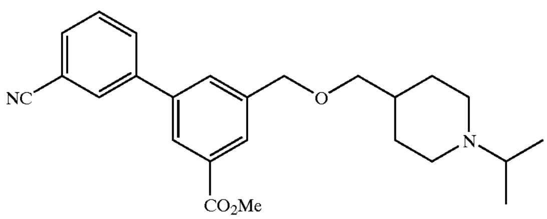 | ¹H-NMR(270MHz, CDCl₃)δ 1.04(d, 6H, J=6.6Hz), 1.6~1.9(m, 4H), 2.13(dt, 2H, J=11.6, 2.3Hz), 2.70(quint., 1H, J=6.6Hz), 2.90(d, 2H, J=11.6Hz), 3.38(d, 2H, J=6.6Hz), 3.96(s, 3H), 4.60(s, 2H), 7.5~7.7(m, 2H), 7.74(s, 1H), 7.8~7.9(m, 1H), 7.90(s, 1H), 8.03(s, 1H). 8.15(s, 1H). |
| 11 | 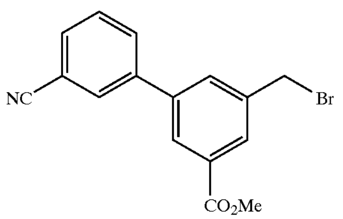 | ¹H-NMR(270MHz, CDCl₃)δ 3.97(s, 3H), 4.58(s, 2H), 7.5~7.9(m, 5H), 8.1~8.2(m, 2H). |
| 12 | 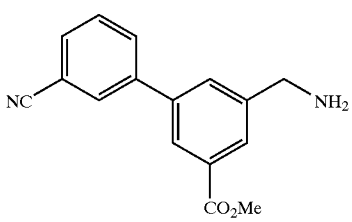 | MS 265[M−H] |
| 13 | 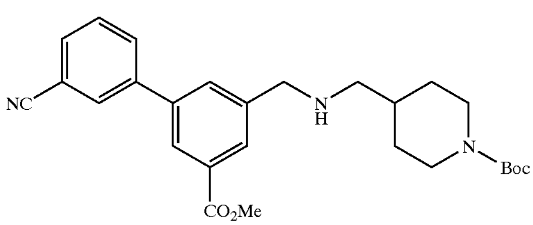 | ¹H-NMR(270MHz, CDCl₃)δ 1.0–1.3(m, 2H), 1.43(s, 9H), 1.7–2.0(m, 3H), 2.6–2.8(m, 4H), 3.95(s, 3H), 4.0–4.2(br S, 4H), 7.5–7.7(m, 2H), 7.9–8.0(m, 2H), 8.09(s, 2H), 8.20(s, 1H). |

TABLE 2-continued
| Production Example | Structure | Structural data |
|---|---|---|
| 14 | 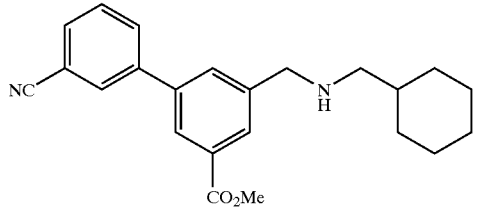 | ¹H-NMR(270MHz, CDCl₃)δ 0.8–1.0(m, 2H), 1.0–1.3(m, 3H), 1.4–1.8(m, 6H), 2.49(d, J=6.6Hz, 2H), 3.90(s, 2H), 3.96(s, 3H), 7.57(dd, J=7.8, 7.8Hz, 1H), 7.65(d, J=7.8Hz, 1H), 7.76(s, 1H), 7.85(d, J=7.8Hz, 1H), 7.91(s, 1H), 8.03(s, 1H), 8.12(s, 1H). |
| 15 | 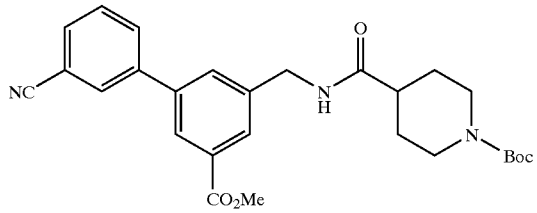 | MS 478[M+H] |
| 16 | 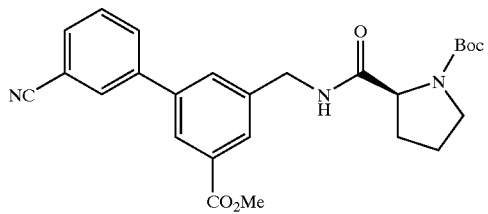 | MS 464[M+H] |
| 17 | 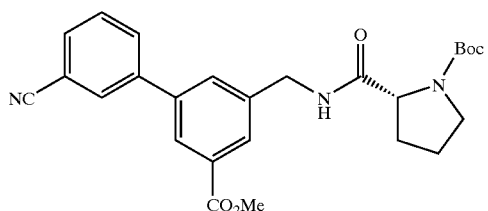 | MS 464[M+H] |
| 18 | 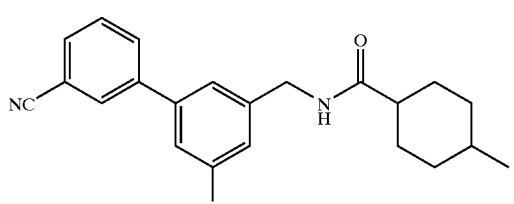 | MS 391[M+H] |
| 19 | 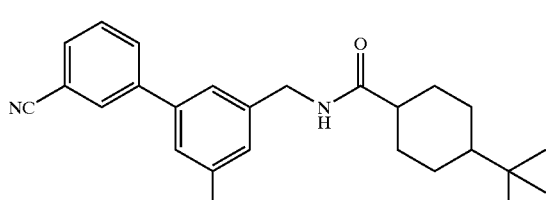 | MS 433[M+H] |

TABLE 2-continued

| Production Example | Structure | Structural data |
|---|---|---|
| 20 | 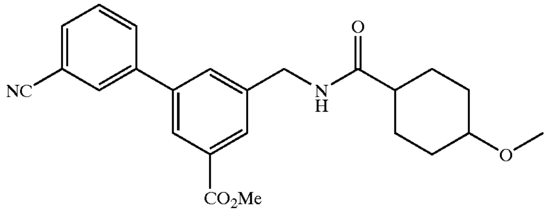 | MS 407[M+H] |
| 21 | 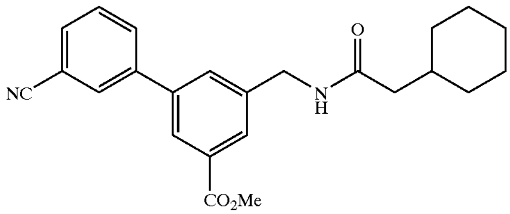 | MS 391[M+H] |
| 22 | 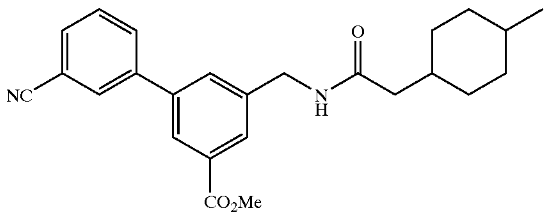 | MS 405[M+H] |
| 23 | 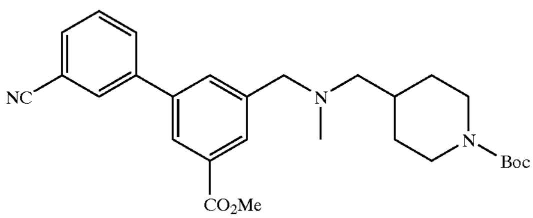 | $^{1}$H-NMR(270MHz, CDCl$_3$)δ 1.0~1.9(m, 5H), 1.49(s, 9H), 2.22(s, 3H), 2.2~2.3(m, 2H), 2.5~2.8(m, 2H), 2.70(t, 2H, J=12.0Hz), 3.57(s, 2H), 3.96(s, 3H), 4.0~4.2(m, 2H), 4.64 & 4.72(s, 2H), 7.5~7.7(m, 2H), 7.72(s, 1H), 7.85(d, 1H, J=7.6Hz), 8.01(s, 1H), 8.12(s, 1H). |
| 24 | 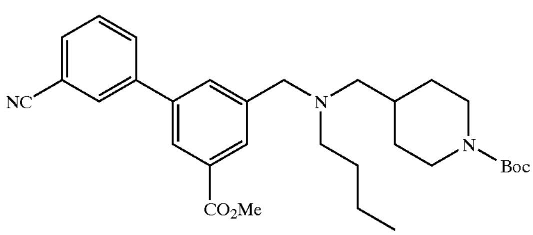 | $^{1}$H-NMR(270MHz, CDCl$_3$)δ 0.9~1.1(m, 5H), 1.2~1.8(m, 17H), 2.26(d, 2H, J=7.0Hz), 2.42(t, 2H, J=7.0Hz), 2.67(brt, 2H, J=11.3Hz), 3.63(s, 2H), 3.96(s, 3H), 4.0~4.2(m, 1H), 7.5~8.2(m, 7H). |
| 25 | 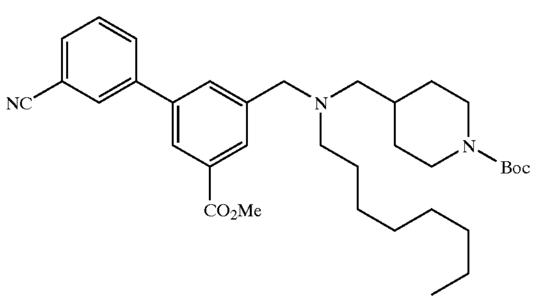 | $^{1}$H-NMR(270MHz, CDCl$_3$)δ 0.8–1.1(m, 5H), 1.1–1.7(m, 15H), 1.43(s, 9H), 1.76(d, J=13.8Hz, 2H), 2.2–2.3(m, 2H), 2.40(t, J=7.3Hz, 2H), 2.67(t, J=12Hz, 2H), 3.62(s, 2H), 3.96(s, 3H), 3.9–4.1(m, 2H), 7.57(dd, J=7.8, 7.8Hz, 1H), 7.67(d, J=7.8Hz, 1H), 7.72(s, 1H), 7.84(d, J=7.9Hz, 1H), 7.89(s, 1H), 8.02(s, 1H), 8.11(s, 1H). |

TABLE 2-continued

| Production Example | Structure | Structural data |
|---|---|---|
| 26 | 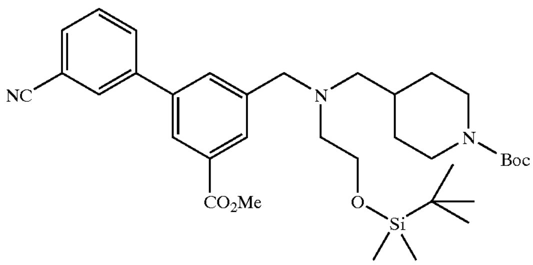 | ¹H-NMR(270MHz, CDCl₃)δ 0.02(s, 6H), 0.84(m, 9H), 0.8–1.1(m, 2H), 1.43(s, 9H), 1.5~2.0(m, 4H), 2.32(d, 2H, J=7.0Hz), 2.5~2.7(m, 4H), 3.5~3.7(m, 4H), 3.94(s 3H), 4.0~4.1(brs, 1H), 7.5~8.2(m, 7H). |
| 27 | 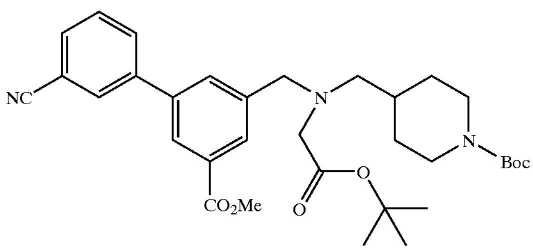 | ¹H-NMR(270MHz, CDCl₃)δ 0.9–1.1(m, 2H), 1.5–1.7(m, 1H), 1.7–1.8(m, 2H), 2.50(d, 2H), 2.68(m, 2H), 3.21(s, 2H), 3.88(s, 2H), 3.93(s, 3H), 4.04(m, 2H), 7.54(m, 1H), 7.64(d, 1H), 7.75(s, 1H), 7.82(d, 1H), 7.86(s. 1H), 8.00(s, 1H), 8.11(s, 1H). |
| 28 | 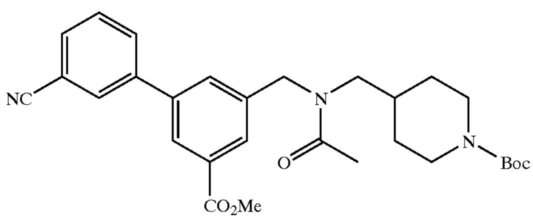 | ¹H-NMR(270MHz, CDCl₃)δ 1.0~2.0(m, 5H), 1.45 & 1.46(s, 9H), 2.15 & 2.21(s, 3H), 2.5~2.8(m, 2H), 3.2~3.3(m, 2H), 3.96 & 3.97(s, 3H), 4.0~4.3(m, 2H), 4.64 & 4.72(s. 2H), 7.4~8.0(m, 6H), 8.1~8.2(m, 1H). |
| 29 | 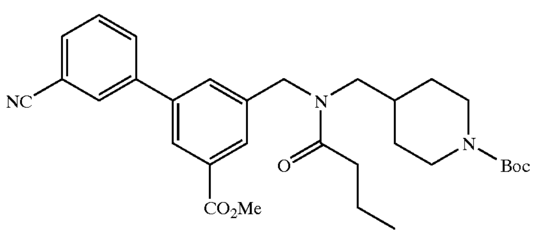 | ¹H-NMR(270MHz, CDCl₃)δ 0.93 & 1.00(t, 3H, J=7.6Hz), 1.0~2.0(m, 17H), 2.32 & 2.37(t, 2H, J=7.6Hz), 2.5~2.8(m, 2H), 3.18 & 3.21(s, 2H), 3.95 & 3.97(s, 3H), 4.0~4.3 (brs, 1H), 4.68 & 4.73(s, 2H), 7.4~8.3(m, 7H). |
| 30 | 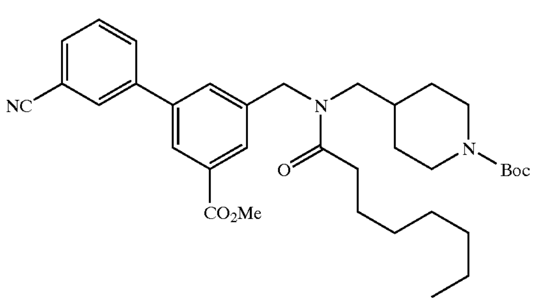 | ¹H-NMR(270MHz, CDCl₃)δ 0.86(brs, 3H), 1.0–1.7(m, 16H), 1.54(d, J=3.9Hz, 9H), 2.35(dt, J=7.5, 20.5Hz, 2H), 2.5–2.8(m, 2H), 3.19(d, J=7.6Hz, 1H), 3.96(d, J=3.7Hz, 3H), 4.0–4.3(m, 2H), 4.7(d, J=12Hz, 2H), 7.4–7.7(m, 3H), 7.8–7.9(m, 3H), 8.15(d, J=11Hz, 1H). |
| 31 | 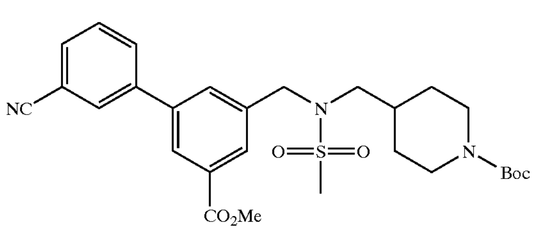 | ¹H-NMR(270MHz, CDCl₃)δ 1.0~1.8(m, 5H), 1.42(s, 9H), 2.53(t, 2H, J=13.0Hz), 2.88(s, 3H), 3.0~3.2(m, 2H), 3.9–4.2(m, 2H), 3.98(s, 3H), 4.50(s, 2H), 7.60(t, 1H, J=7.8Hz), 7.69(d, 1H, J=7.6Hz), 7.8–7.9(m, 1H), 7.89(s, 1H), 8.03(s, 1H), 8.20(s, 1H). |

TABLE 2-continued

| Production Example | Structure | Structural data |
|---|---|---|
| 32 | 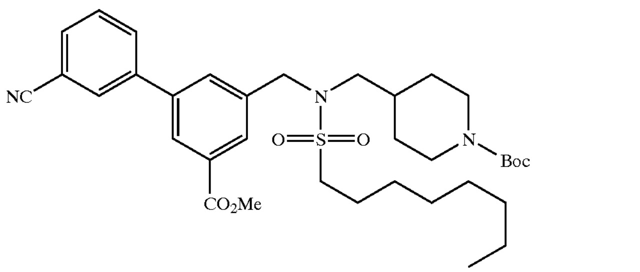 | $^1$H-NMR(270MHz, CDCl$_3$)δ 0.8–0.9( m, 3H), 0.9–1.2(m, 2H), 1.2–1.7(m, 15H), 1.42(s, 9H), 2.50(t, J=13Hz, 2H), 2.9–3.0(m, 2H), 3.1–3.2(m, 2H), 3.97(s, 3H), 3.9–4.2(m, 2H), 4.51(s, 2H), 7.61(dd, J=7.7, 7.7Hz, 1H), 7.70(d, J=7.7Hz. 1H), 7.8–7.9(m, 3H), 8.03(s, 1H), 8.19(s, 1H). |
| 33 | 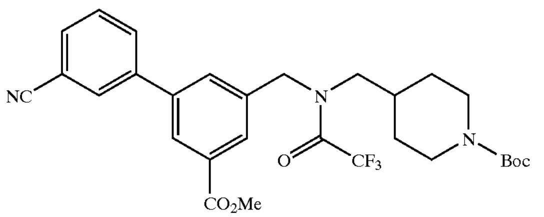 | MS 560[M +H] |
| 34 | 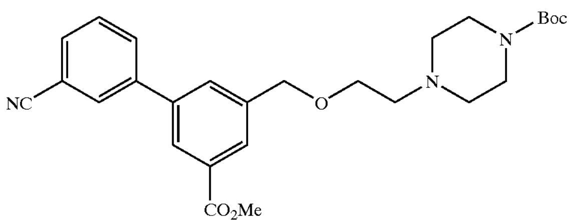 | $^1$H-NMR(270MHz, CDCl$_3$)δ 1.45(s, 9H), 2.4~2.5(m, 4H), 2.66(t, 2H, J=5.9Hz), 3.4~3.5(m, 4H), 3.66(t, 2H, J=5.8Hz), 3.97(s, 3H), 4.65(s, 2H), 7.5~8.2(m, 7H). |
| 35 | 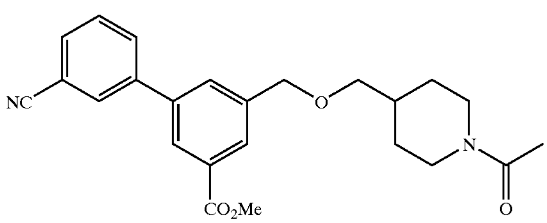 | $^1$H-NMR(270MHz, CDCl$_3$)δ 1.0~1.3(m, 2H), 1.7~2.0(m, 3H), 2.09(s, 3H), 2.56(td, 1H, J=12.8, 2.9Hz), 3.06(td, 1H, J=13.2, 2.0Hz), 3.2~3.5(m, 2H), 3.83(brd, 1H, J=13.5Hz), 3.97(s, 3H), 4.65(s, 2H), 4.5~4.8(m, 1H), 7.58(t, 1H, J=7.8Hz), 7.6–7.8(m, 1H), 7.72(s, 1H), 7.85(d, 1H, J=7.9Hz), 7.90(s, 1H), 8.03(s, 1H), 8 17(s, 1H). |
| 36 | 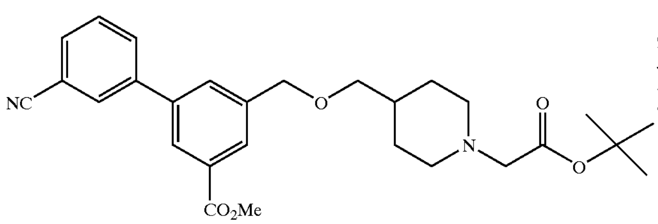 | $^1$H-NMR(270MHz, CDCl$_3$)δ 1.2–1.4(m, 2H), 1.46(s, 9H), 1.6–18(m, 3H), 2.17(d, J=11Hz, 2H), 2.96(d, J=9Hz, 2H), 3.11(s, 2H), 3.38(d, J=6.3Hz, 2H), 3.96(s, 3H), 4.60(s, 2H), 7.5–7.9(m, 5H), 8.03(s, 1H), 8.15(s, 1H). |
| 37 | 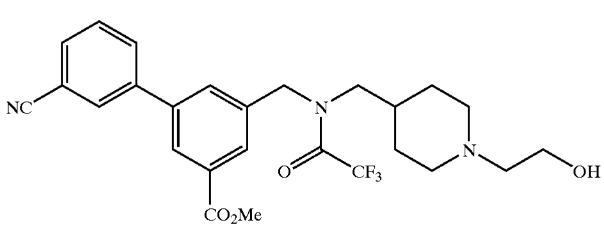 | MS 504[M+H] |

TABLE 2-continued

| Production Example | Structure | Structural data |
|---|---|---|
| 38 | 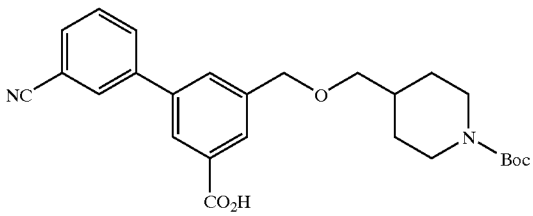 | $^1$H-NMR(270MHz, CDCl$_3$)δ 1.0~1.3(m, 2H), 1.46(s, 9H), 1.7~2.0(m, 3H), 2.56(td, 1H, J=12.8, 2.9Hz), 3.05(td, 1H, J=13.2, 2.0Hz), 3.2~3.5(m, 2H), 3.83(brd, 1H, J=13.5Hz), 4.65(s, 2H), 4.6~4.8(m, 1H), 7.60(t, 1H, J=7.8Hz), 7.6~7.8(m, 1H), 7.74(s, 1H), 7.85(d, 1H, J=7.9Hz), 7.90(s, 1H). 8.03(s, 1H), 8.16(s, 1H). |
| 39 | 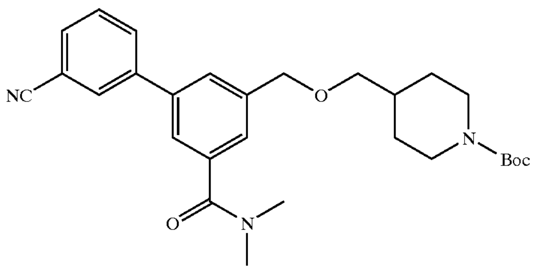 | $^1$H-NMR(270MHz, CDCl$_3$)δ 1.0~1.3(m, 2H), 1.46(s, 9H), 1.7~2.0(m, 3H), 2.56(td, 1H, J=12.8, 2.9Hz), 3.0(brs, 4H), 3.14(s, 3H), 3.2~3.5(m, 2H), 3.83(brd, 1H, J=13.5Hz), 4.65(s, 2H), 4.6~4.9(m, 1H), 7.60(t, 1H, J=7.8Hz), 7.6~7.8(m, 1H), 7.74(s, 1H), 7.86(d, 1H, J=7.8Hz), −7.92(s, 1H), 8.04(s, 1H). 8.17(s, 1H). |
| 40 | 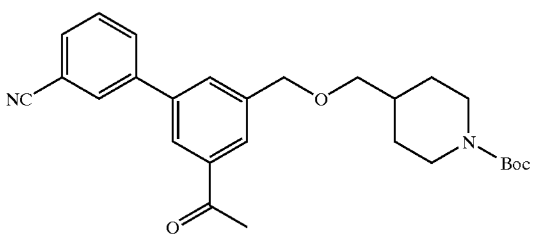 | $^1$H-NMR(270MHz, CDCl$_3$)δ 1.0~1.3(m, 2H), 1.46(s, 9H), 1.7~2.0(m, 3H), 2.09(s, 3H), 2.56(td, 1H, J=12.8, 2.9Hz), 3.06(td, 1H, J=13.2, 2.0Hz), 3.2~3.5(m, 2H), 3.8s(brd, 1H, J=13.5Hz), 4.65(s, 2H), 4.5~4.7(m, 1H), 7.60(t, 1H, J=7.9Hz), 7.6~7.8(m, 1H), 7.70(s, 1H), 7.85(d, 1H, J=7.9Hz), 7.90(s, 1H), 8.02(s, 1H), 8.16(s, 1H). |

TABLE 3

| Example | Structure | Structural data |
|---|---|---|
| 1 | 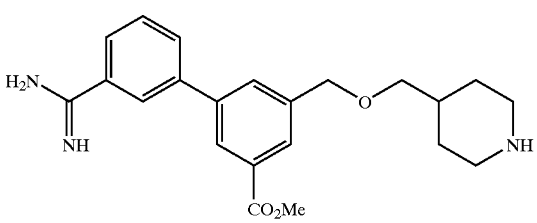 | $^1$H-NMR(DMSO-d$_6$)δ 1.3~1.5(m, 2H), 1.7~2.0(m, 3H), 2.7~2.9(m, 2H), 3.15~3.3(m, 2H), 3.38(d, 2H, J=6.3Hz), 3.91(s, 3H), 4.64(s, 2H), 7.69(t, 1H, J=7.9Hz), 7.86(d, 1H, J=7.9Hz), 7.99(s, 1H), 8.02(s, 1H), 8.07(d, 1H, J=7.6Hz), 8.15(s, 1H), 8.28(s, 1H), 8.55 & 8.85(brs, 1H), 9.19 & 9.52(s, 2H). |
| 2 | 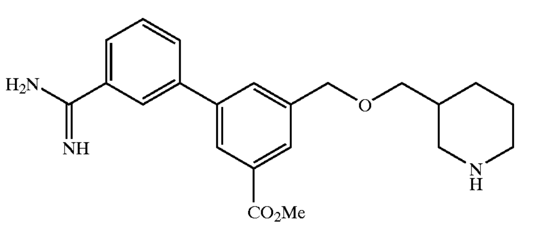 | $^1$H-NMR(DMSO-d$_6$)δ 1.1~2.3(m, 5H), 2.5~2.9(m, 2H), 3.1~3.6(m, 4H), 3.92(s, 3H), 4.63(s, 2H), 7.6~8.3(m, 7H), 9.1~9.6(m, 4H). |

TABLE 3-continued

| Example | Structure | Structural data |
|---|---|---|
| 3 | 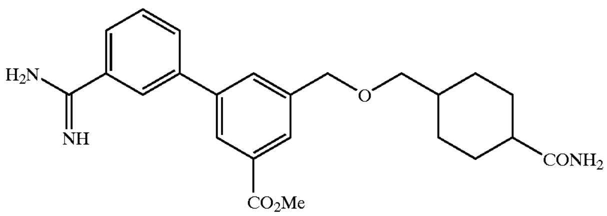 | $^1$H-NMR(DMSO-$d_6$)δ 0.8~2.2(m, 10H), 3.2~3.4(brs, 2H), 3.91(s, 2H), 6.6~6.7(brs, 1H), 7.1~7.2(brs, 1H), 7.7~8.3(m, 7H), 9.0~9.2(brs, 1H), 9.4~9.5(brs, 2H). |
| 4 | 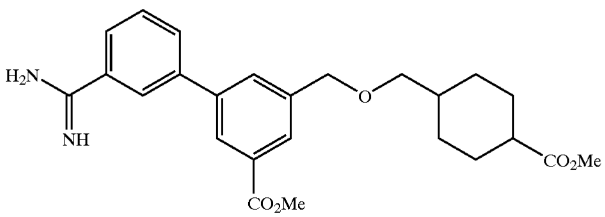 | $^1$H-NMR(DMSO-$d_6$)δ 0.9~2.3(m, 10H), 3.0~3.4(brs, 2H), 3.58(s, 3H), 3.91(s, 3H), 4.61(s, 2H), 7.6~8.4(m, 7H). |
| 5 | 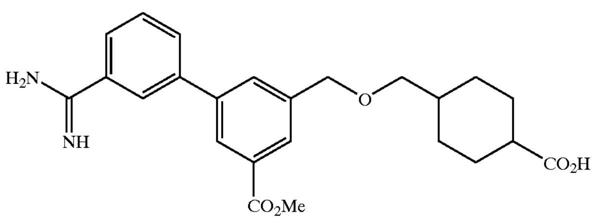 | $^1$H-NMR(DMSO-$d_6$)δ 0.8~2.2(m, 10H), 3.1~3.4(brs, 2H), 3.91(s, 3H), 4.61(s, 2H), 7.6~8.3(m, 7H). |
| 6 | 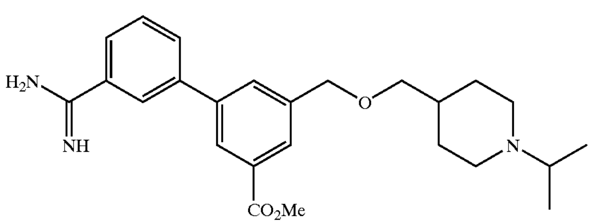 | $^1$H-NMR(DMSO-$d_6$)δ 1.26(d, 6H, J=6.9Hz), 1.6~2.0(m, 5H), 2.8~3.0(m, 2H), 3.1~3.5(m, 5H), 3.92(s, 3H), 4.65(s, 2H), 7.74(t, 1H, J=7.8Hz), 7.90(d, 1H, J=7.9Hz), 7.98(s, 1H), 8.07(s, 1H), 8.08(d, 1H, J=8.3Hz), 8.18(s, 1H), 8.27(s, 1H), 9.40 & 9.62(brs, 3H). |
| 7 | 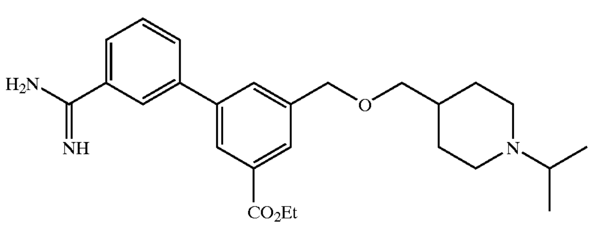 | $^1$H-NMR(DMSO-$d_6$)δ 1.25(d, 6H, J=6.9Hz), 1.36(t, 3H, J=7.1Hz), 1.6~2.0(m, 5H), 2.8~3.0(m, 2H), 3.1~3.5(m, 5H), 4.38(q, 2H, J=7.0Hz), 4.65(s, 2H), 7.74(t, 1H, J=7.9Hz), 7.87(d, 1H, J=7.9Hz), 7.98(s, 1H), 8.05(s, 1H), 8.07(d, 1H, J=12.2Hz), 8.17(s, 1H), 8.26(s, 1H), 9.33 & 9.58(brs, 3H). |
| 8 | 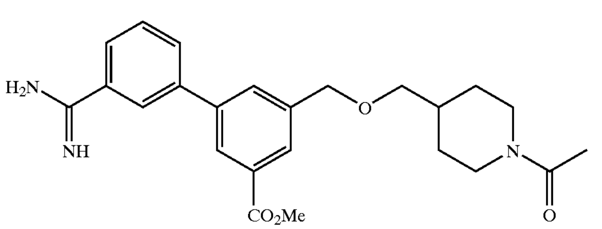 | $^1$H-NMR(DMSO-$d_6$)δ 0.9~1.3(m, 2H), 1.6~2.0(m, 3H), 1.97(s, 3H), 2.4~2.65(m, 1H), 3.00(brt, 1H, J=11.7Hz), 3.2~3.5(m, 2H), 3.80(brd; 1H, J=14.9Hz), 3.91(s, 3H), 4.37(brd, 1H, J=4.37Hz), 4.63(s, 2H), 7.71(t, 1H, J=7.7Hz), 7.83(d, 1H, J=7.9Hz), 7.98(s, 2H), 8.02(d, 1H, J=7.9Hz), 8.11(s, 1H), 8.25(s, 1H), 8.17(s, 1H), 9.4~10.0(br, 3H). |

TABLE 3-continued
| Example | Structure | Structural data |
|---|---|---|
| 9 | 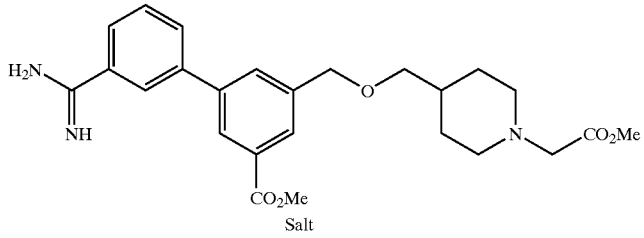 | ¹H-NMR(DMSO-d₆)δ 1.5~2.0(m, 5H), 2.9–3.7(m, 6H), 3.74(s, 3H), 3.92(s, 3H), 4.64(s, 2H), 7.7–8.3(m, 7H), 9.14(brs, 2H), 9.51(brs, 2H). |
| 10 | 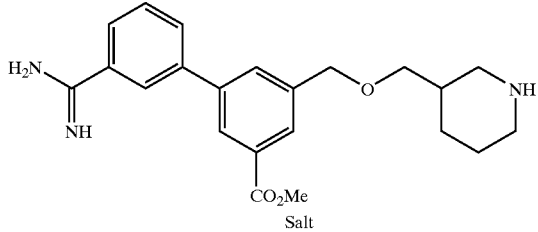 | ¹H-NMR(DMSO-d₆)δ 1.8–2.2(m, 4H), 2.8~3.3(m, 4H), 3.7~3.8(m, 1H), 3.92(s, 3H), 4.69(s, 2H), 7.7~8.3(m, 7H), 8.7~9.0(brs, 1H), 9.1~9.2(brs, 2H), 9.5~9.6(brs, 2H). |
| 11 | 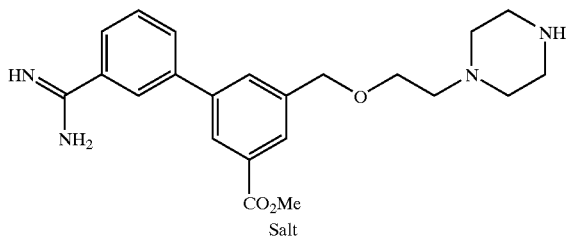 | ¹H-NMR(DMSO-d₆)δ 2.6~2.8(m, 6H), 3.0~3.2(m, 4H), 3.5~3.8(m, 2H), 3.92(s, 3H), 4.66(s, 2H), 7.6~8.3(m, 7H), 9.06 & 9.48(brs, 3H). |
| 12 | 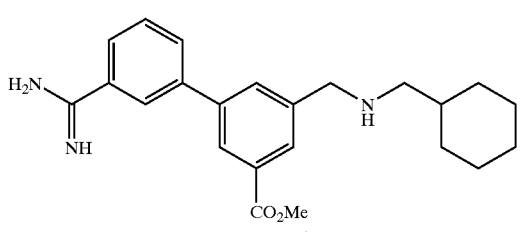 | ¹H-NMR(DMSO-d₆)δ 0.8~2.0(m, 11H), 2.82(brs, 2H), 3.94(s, 3H), 4.31(brs, 2H), 7.7~8.5(m, 7H), 9.1~9.6(m, 3H). |
| 13 | 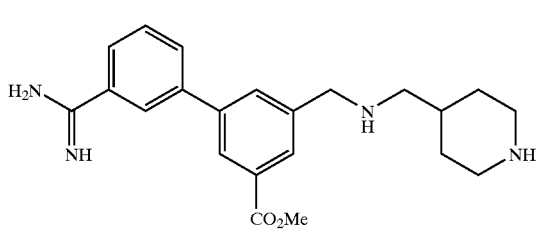 | ¹H-NMR(DMSO-d₆)δ 1.3–1.5(m,2H), 1.96–2.0(m, 2H), 2.1(brs, 1H), 2.7–3.0(m,4H), 3.97(s, 3H), 4.32(s, 2H), 7.76(t, J=7.8Hz, 1H), 7.89(d, J=7.8Hz, 1H), 8.1–8.5(m, 5H). |
| 14 | 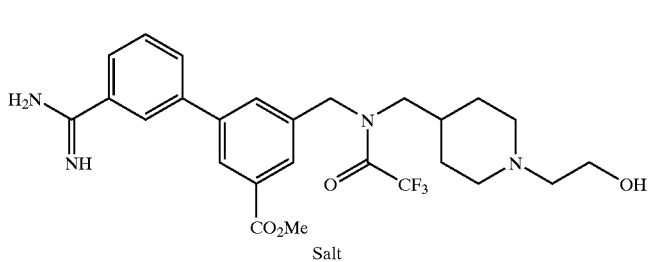 | ¹H-NMR(270MHz, DMSO-d₆+D₂O)δ 1.4–1.7(m, 2H), 1.7–1.9(m, 2H), 2.0–2.3(m, 1H), 2.8–3.2(m, 2H), 3.2–4.0(m, 8H), 3.88(s, 3H), 4.82(d, J=21Hz, 2H), 7.6–8.3(m, 7H). |

TABLE 3-continued

| Example | Structure | Structural data |
|---|---|---|
| 15 | 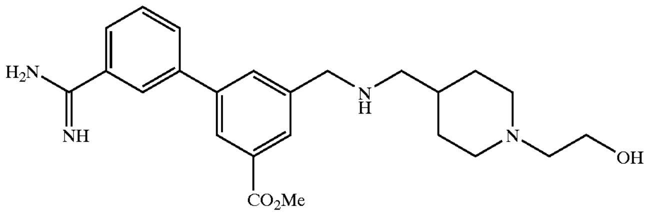 | ¹H-NMR(270MHz, DMSO-d₆+D₂O)δ 1.4–2.3(m, 5H), 2.7–4.0(m, 10H), 3.91(s, 3H), 4.30(s, 2H), 7.74(t, J=7.6Hz, 1H), 7.88(d, J=7.6Hz, 1H), 8.1–8.3(m, 3H), 8.37(s, 1H), 8.48(s, 1H). |
| 16 | 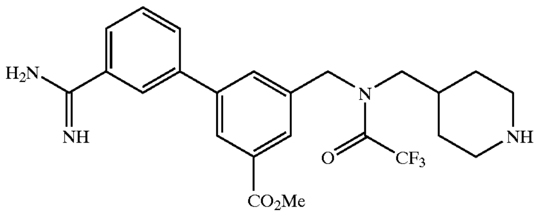 | ¹H-NMR(DMSO-d₆)δ 1.2~1.5(m, 2H), 1.6~1.8(m, 2H), 2.1(brs, 1H), 2.7~3.0(m, 2H), 3.2~3.4(m, 2H), 3.92(s, 3H), 4.85(d, J=20Hz, 2H), 7.7~8.5(m, 7H). |
| 17 | 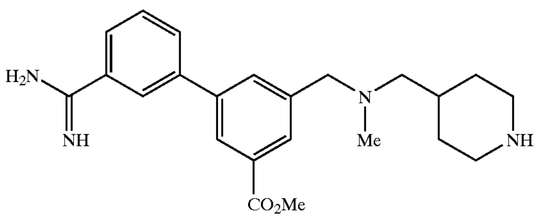 | ¹H-NMR(DMSO-d₆)δ 1.1~1.6(m, 2H), 1.8~2.3(m, 3H), 2.4~3.2(m, 9H), 3.93(s, 3H), 4.3~4.7(m, 3H), 7.8~8.0(m, 2H), 8.1~8.6(m, 4H), 9.2 & 9.55(brs, 3H). |
| 18 | 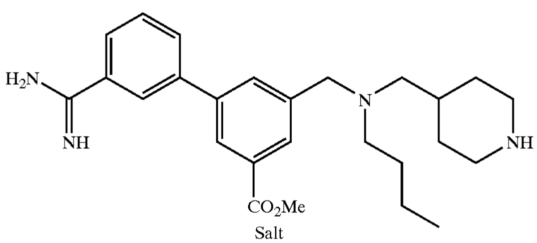 | ¹H-NMR(DMSO-d₆)δ 0.83(t, 3H, J=5.7Hz), 1.0~1.6(m, 6H), 1.8~2.0(m,H), 2.3~2.5(m, 4H), 3.0~3.5(m, 4H), 3.68(s, 2H), 3.91(s, 3H), 3.9~4.1(brs, 1H), 7.5~8.5(m, 7H). |
| 19 | 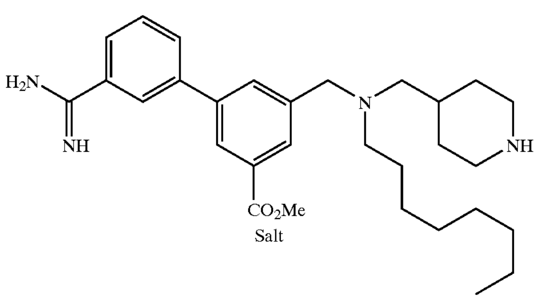 | ¹H-NMR(DMSO-d₆)δ 0.7–0.8(m, 3H), 1.1~2.2(m, 15H), 2.3~2.7(m, 4H), 2.8(brs, 2H), 3.2~3.4(m, 4H), 3.97(s, 3H), 4.5(brs, 2H), 7.7~8.3(m, 7H), 9.26(brs, 2H), 9.57(brs, 2H). |
| 20 | 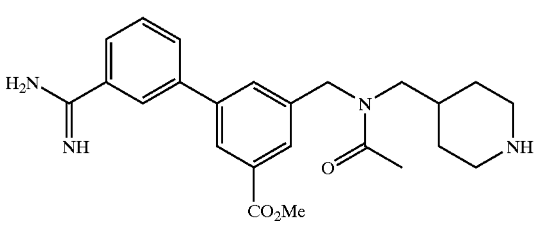 | ¹H-NMR(DMSO-d₆)δ 1.3~1.5(m, 2H), 1.7~2.2(m, 3H), 2.05 & 2.13(s, 3H), 2.7~2.9(m, 2H), 3.2~3.5(m, 2H), 3.91(s, 3H), 4.66 & 4.75(s, 2H), 7.4~8.3(m, 7H), 9.13(m, 3H). |

TABLE 3-continued

| Example | Structure | Structural data |
|---|---|---|
| 21 | 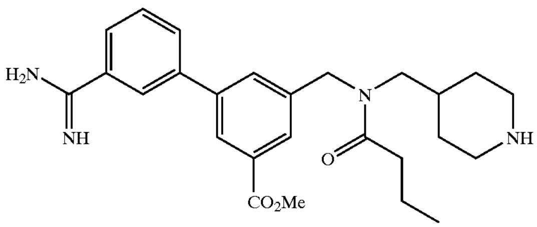 | $^1$H-NMR(DMSO-$d_6$)δ 0.84 & 0.92(t, 3H, J=7.3Hz), 1.0~1.3(m, 2H), 1.5~2.0(m, 5H), 2.31 & 2.36(t, 2H, J=7.6Hz), 2.4~2.6(m, 2H), 2.9~3.1(m, 2H), 3.20 & 3.25(d, 2H, J=7.6Hz), 3.91(s, 3H), 4.65 & 4.71(s, 2H), 7.2~8.2(m, 7H). |
| 22 | 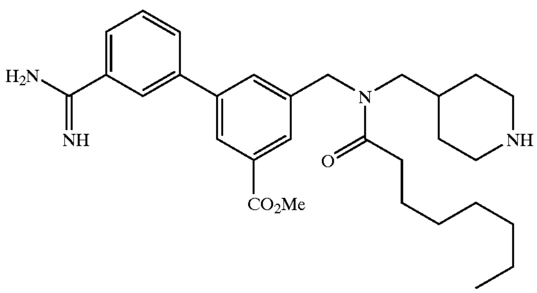 | $^1$H-NMR(DMSO-$d_6$)67 0.7–0.85(m, 3H), 1.1–2.2(m, 16H), 2.29(t, J=7.6Hz, 1H), 2.38(t, J=7.3Hz, 1H), 2.8(brs, 2H), 3.2–3.4(m, 3H), 3.89(d, J=2.7Hz, 3H), 4.70(d, J=25.9Hz, 2H), 7.7–8.3(m, 7H), 9.26(brs, 2H), 9.57(brs, 2H). |
| 23 | 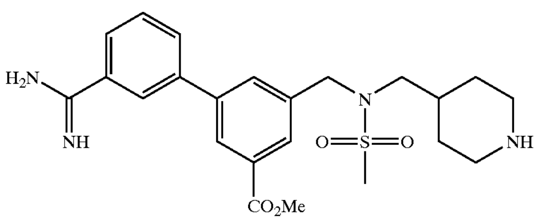 | $^1$H-NMR(DMSO-$d_6$)δ 1.2~1.4(m, 2H), 1.6~1.9(m, 3H), 2.64(t, 2H, J=11.5Hz), 3.02(s, 3H), 3.0~3.2(m, 6H), 3.92(s, 3H), 4.52(s, 2H), 7.75(t, 1H, J=7.7Hz), 7.90(d, 1H, J=7.8Hz), 8.05(d, 1H, J=10.5Hz), 8.07(s, 1H), 8.13(s, 1H), 8.20(s, 1H), 8.31(s, 1H). |
| 24 | 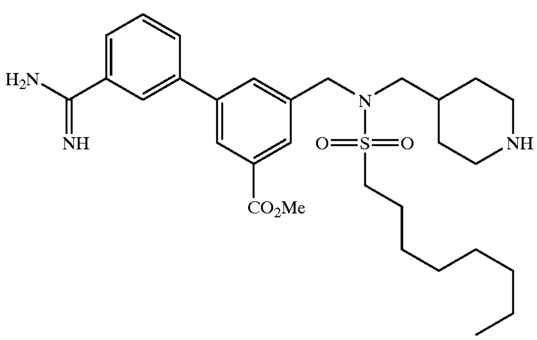 | $^1$H-NMR(DMSO-$d_6$)δ 0.7–0.85(m, 3H), 1.1–2.2(m, 16H), 2.29(t, J=7.6Hz, 1H), 2.38(t, J=7.3Hz, 1H), 2.8(brs, 2H), 3.2–3.4(m, 3H), 3.93(d, J=2.7Hz, 3H), 4.5–4.70(m, 4H), 7.74(dd, J=7.7, 7.7Hz, 1H), 7.90(d, J=7.7Hz, 1H), 8.05(d, J=7.8Hz, 1H), 8.08(s, 1H), 8.13(s, 1H), 8.20(s, 1H), 8.30(s, 1H), 9.26(brs, 2H), 9.57(brs, 2H). |
| 25 | 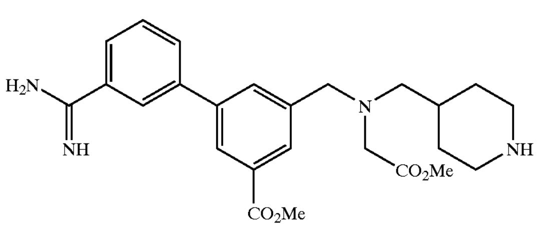 | $^1$H-NMR(DMSO-$d_6$)δ 1.8~1.9(m, 2H), 2.4~2.6(m, 2H), 2.8(m, 2H), 3.21(d, 2H), 3.53(brs, 2H), 3.63(s, 3H), 3.92(s, 3H), 4.00(brs, 2H), 7.75(t, 1H), 7.86(d, 1H), 8.0~8.1(brs, 3H), 8.14(s, 1H), 8.27(s, 1H), 9.22(s, 1H), 9.52(s. 2H). |

TABLE 3-continued

| Example | Structure | Structural data |
|---|---|---|
| 26 | (structure shown) Salt | MS 438[M+H] |
| 27 | (structure shown) Salt | $^1$H-NMR(DMSO-d$_6$)δ 1.0~1.3(m, 2H), 1.5~2.0(m, 3H), 2.30(d, 2H, J=6.5Hz), 2.4~2.6(m, 2H), 3.13(brd, 2H, J=12.4Hz), 3.50(t, 2H, J=5.9Hz), 3.73(s, 2H), 3.89(s, 3H), 7.5~8.4(m, 7H). |
| 28 | (structure shown) Salt | $^1$H-NMR(DMSO-d$_6$)δ 1.15(t, J=7.0Hz, 3H), 1.33~1.52(m, 2H), 1.73~1.95(m, 3H), 2.63~2.75(m, 2H), 2.75~3.00(m, 4H), 3.25~3.55(m, 4H), 4.08(q, J=7.0Hz, 2H), 4.53(s, 2H), 7.23(s, 1H), 7.52~7.63(m,2H), 7.64~7.72(m, 1H), 7.80~7.87(m, 1H), 7.98~8.03(m, 1H), 8.10(s, 1H), 9.2(brs, 3H). |
| 29 | (structure shown) Salt | MS 423[M+H] |
| 30 | (structure shown) Salt | MS 439[M+H] |
| 31 | (structure shown) Salt | $^1$H-NMR(DMSO-d$_6$)δ 1.3~1.5(m, 2H), 1.7~2.0(m, 3H), 2.7~2.9(m, 2H), 2.97(s, 3H), 3.15~3.3(m, 2H), 3.38(d, 2H, J=6.3Hz), 4.64(s, 2H), 7.69(t, 1H, J=7.9Hz), 7.86(d, 1H, J=7.9Hz), 7.99(s, 1H), 8.01(s, 1H), 8.07(d, 1H, J=7.6Hz), 8.14(s, 1H), 8.27(s, 1H). |

TABLE 3-continued
| Example | Structure | Structural data |
|---|---|---|
| 32 | 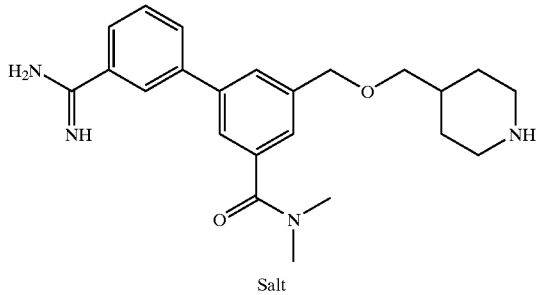<br>Salt | $^1$H-NMR(DMSO-$d_6$)δ 1.3~1.4(m, 2H), 1.7~2.0(m, 3H), 2.7~2.9(m, 2H), 2.97(s, 3H), 3.02(s, 3H), 3.1~3.3(m, 2H), 3.3~3.5(m, 2H), 4.62(s, 2H), 7.67(t, 1H, J=7.8Hz), 7.86(d, 1H, J=7.98Hz), 7.97(s, 1H), 8.00(s, 1H), 8.07(d, 1H, J=7.6Hz), 8.14(s, 1H), 8.27(s, 1H). |
| 33 | 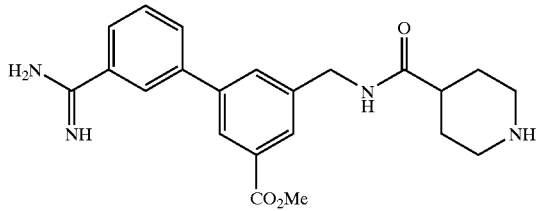<br>Salt | MS 395[M+H] |
| 34 | 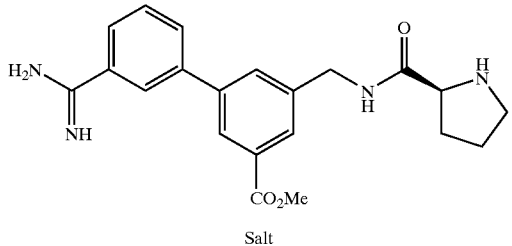<br>Salt | Ms 381[M+H] |
| 35 | 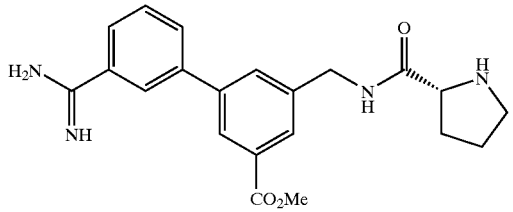<br>Salt | MS 381[M+H] |
| 36 | 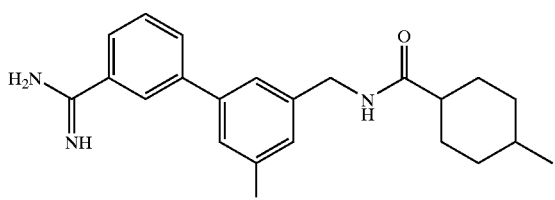<br>Salt | MS 408[M+H] |

TABLE 3-continued

| Example | Structure | Structural data |
|---|---|---|
| 37 | (structure shown) Salt | MS 450[M+H] |
| 38 | (structure shown) Salt | MS 424[M+H] |
| 39 | (structure shown) Salt | MS 408[M+H] |
| 40 | (structure shown) Salt | MS 422[M+H] |
| 41 | (structure shown) Salt | $^1$H-NMR(270MHz, DMSO-$d_6$)δ 1.1~1.4(m, 2H), 1.7~2.1(m, 3H), 2.50(s, 3H), 3.0~3.5(m, 4H), 3.8~4.0(m, 1H), 3.91(s, 3H), 4.0~4.2(m, 1H), 4.64(s, 2H), 7.74(t, 1H, J=7.8Hz), 7.87(d, 1H, J=7.6Hz), 8.00(s, 1H), 8.03(s, 1H), 8.07(d, 1H, J=7.6Hz), 8.16(s, 1H), 8.28(s, 1H), 8.64 & 9.20(brs, 1H), 9.25 & 9.54(brs, 2H). |
| 42 | (structure shown) Salt | $^1$H-NMR(270MHz, DMSO-$d_6$)δ 1.3~2.1(m, 5H), 2.27(s, 3H), 2.9~3.2(m, 2H), 3.44(d, 2H, J=5.6Hz), 3.92(s, 3H), 3.7~4.1(m, 3H), 4.65(s, 2H), 7.7~8.3(m, 7H), 9.1~9.6(m, 4H). |

TABLE 3-continued
| Example | Structure | Structural data |
|---|---|---|
| 43 | 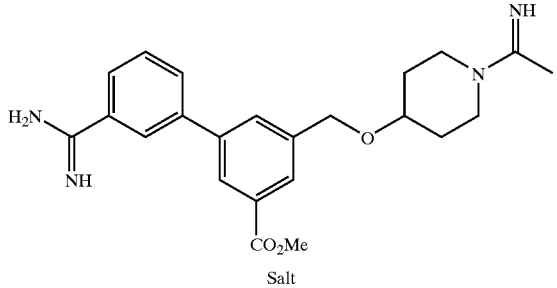 Salt | ¹H-NMR(270MHz, DMSO-d₆)δ 1.6~2.2(m, 4H), 2.28(s, 3H), 3.2~3.8(m, 5H), 3.92(s, 3H) 4.71(s, 2H), 7.6~8.4(m, 7H). |
| 44 | 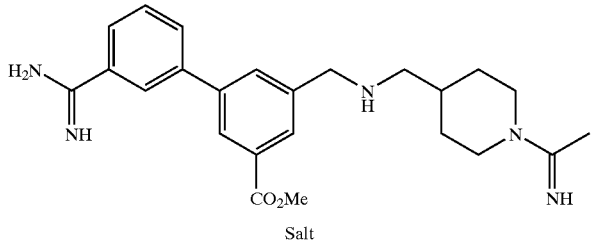 Salt | ¹H-NMR(270MHz, DMSO-d₆+D₂O)δ 1.2~1.5(m, 2H), 1.8~2.0(m, 2H), 2.1(brs, 1H), 2.26(s, 3H), 2.9~3.2(m, 4H), 3.94(s, 3H), 3.9~4.1(m, 2H), 4.35(s, 2H), 7.8~8.2(m, 6H). 8.43(s, 1H). |
| 45 | 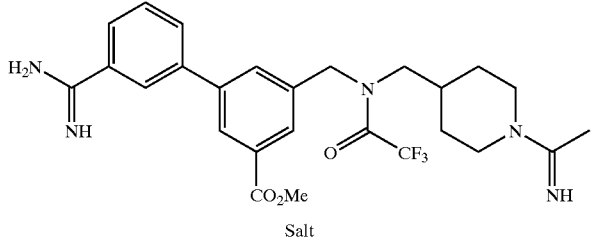 Salt | ¹H-NMR(270MHz, DMSO-d₆+D₂O)δ 1.1~1.5(m, 2H), 1.9~1.7(m, 2H), 2.26(s, 3H), 2.1~2.3(m, 2H), 3.0~3.5(m, 4H), 3.92(s, 3H), 3.9~4.1(m, 2H), 4.8~5.0(m, 2H), 7.7~8.1(m, 5H), 8.13(s, 1H), 8.3(m, 1H). |
| 46 | 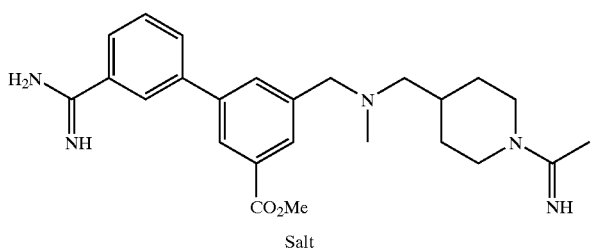 Salt | ¹H-NMR(270MHz, DMSO-d₆)δ 1.1~1.4(m, 2H), 1.8~2.3(m, 3H), 2.27(s, 6H), 3.0~4.3(m, 8H), 3.93(s, 3H), 7.7~8.8(m, 7H), 9.47 & 9.70(brs, 3H). |
| 47 | 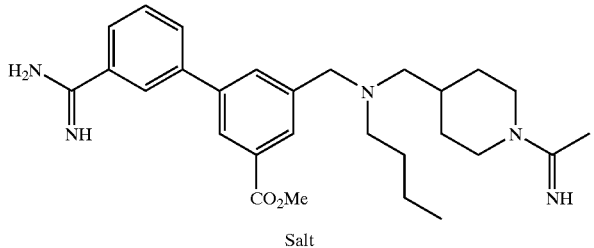 Salt | ¹H-NMR(270MHz, DMSO-d₆)δ 0.83(t, 3H, J=5.7Hz), 1.0~1.6(m, 6H), 1.8~2.0(m, H), 2.24(s, 3H), 2.3~2.5(m, 4H), 3.0~3.5(m, 4H), 3.68(s, 2H), 3.91(s, 3H), 3.9~4.1(brs, 1H), 7.5~8.5(m, 7H). |

TABLE 3-continued

| Example | Structure | Structural data |
|---|---|---|
| 48 | 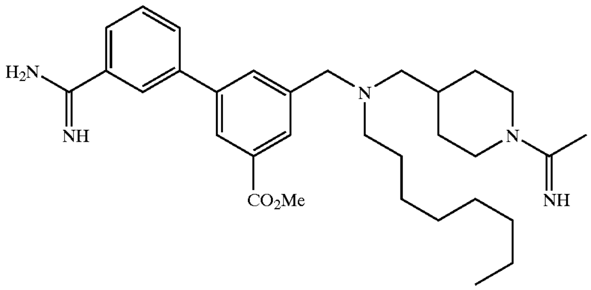 | ¹H-NMR(270MHz, DMSO-d₆)δ 0.7–0.8(m, 3H), 1.1–2.2(m, 15H), 2.24(s, 3H), 2.3–2.6(m, 2H), 2.6–3.4(m, 4H), 3.7–4.2(m, 2H), 3.93(s, 3H), 4.45(brs, 2H), 7.8–8.3(m, 7H), 9.3(brs, 2H), 9.6(brs, 2H). |
| 49 | 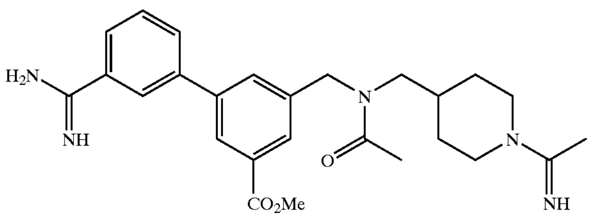 | ¹H-NMR(270MHz, DMSO-d₆)δ 1.1~1.5(m, 2H), 1.7~1.9(m, 2H), 2.09 & 2.14(s, 3H), 2.0~2.3(m, 1H), 2.21 & 2.29(s, 3H), 3.0~4.3(m, 6H), 3.91(s, 3H), 4.67 & 4.77(s, 2H), 7.7~8.4(m, 7H), 9.41(brs, 3H). |
| 50 | 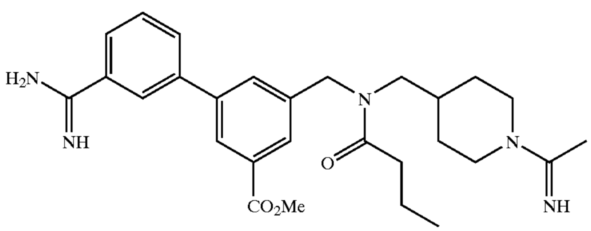 | ¹H-NMR(270MHz, DMSO-d₆)δ 0.84 & 0.92(t, 3H; J=7.3Hz), 1.0~1.3(m, 2H), 1.5~2.0(m, 5H), 2.22 & 2.24(s, 3H), 2.31 & 2.36(t, 2H, J=7.6Hz), 2.4~2.6(m, 2H), 2.9~3.1(m, 2H), 3.20 & 3.25(d, 2H, J=7.6Hz), 3.91(s, 3H), 4.65 & 4.71(s, 2H), 7.2~8.2(m, 7H). |
| 51 | 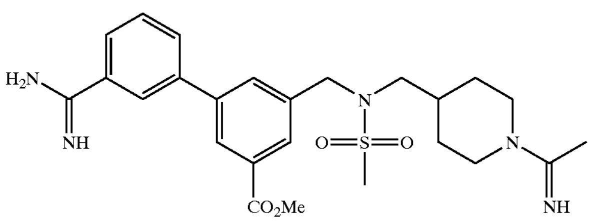 | ¹H-NMR(270MHz, DMSO-d₆)δ 1.0~1.3(m, 2H), 1.6~2.0(m, 3H), 2.24(s, 3H), 2.8~3.5(m, 6H), 3.02(s, 3H), 3.93(s, 3H), 4.54(s, 2H), 7.75(t, 1H, J=7.7Hz), 7.91(d, 1H, J=8.1Hz), 8.03(d, 1H, J=7.8Hz), 8.08(s, 1H), 8.18(s, 1H), 8.23(s, 1H), 8.29(s, 1H), 9.4(m, 3H). |
| 52 | 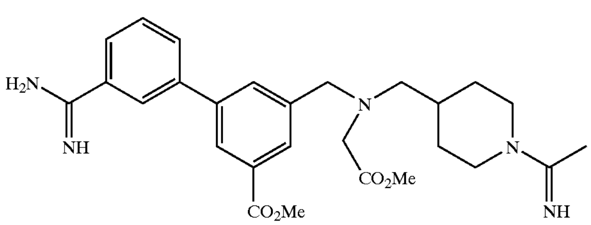 | ¹H-NMR(270MHz, DMSO-d₆)δ 1.1~1.3(m, 2H), 1.8~1.9(m, 3H), 2.22(s, 3H), 2.5~2.8(m, 4H), 3.2~3.4(m, 4H), 3.62(s, 3H), 3.9~4.0(brs, 2H), 3.91(s, 3H), 7.76(t, 1H), 7.85(d, 1H), 7.9~8.1(m, 3H), 8.25(s, 1H), 8.44(s, 1H), 9.00(s, 1H), 9.19(s, 1H), 9.44(s, 2H). |

TABLE 3-continued

| Example | Structure | Structural data |
|---|---|---|
| 53 | 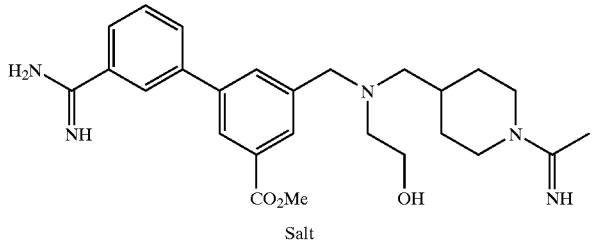 | ¹H-NMR(270MHz, DMSO-d₆)δ 1.0~1.3(m, 2H), 1.5~2.0(m, 3H), 2.24(s, 3H), 2.30(d, 2H, J=6.5Hz), 2.4~2.6(m, 2H), 3.13(brd, 2H, J=12.4Hz), 3.50(t, 2H, J=5.9Hz), 3.73(s, 2H), 3.89(s, 3H), 7.5~8.4(m, 7H). |
| 54 | 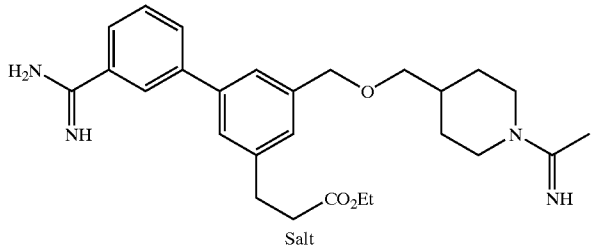 | ¹H-NMR(270MHz, DMSO-d₆)δ 1.16(t, J=7.0Hz, 3H), 1.17~1.45(m, 2H), 1.79~1.88(m, 2H), 2.27(s, 3H), 2.65~2.75(m, 2H), 2.27(s, 3H), 2.65~2.75(m, 2H), 2.89~3.00(m, 2H), 3.00~3.35(m, 2H), 3.95~4.0(m, 1H), 4.1(q, J=7.0Hz, 2H), 4.55(s, 2H), 7.22(s, 1H), 7.55~7.59(m, 2H), 7.65~7.73(m, 1H), 7.78~7.85*(m, 1H), 7.98~8.02(m, 1H), 8.03~8.08(m, 1H), 8.14(s, 1H), 9.2(brs, 1H). 9.55(brs, 1H). |
| 55 | 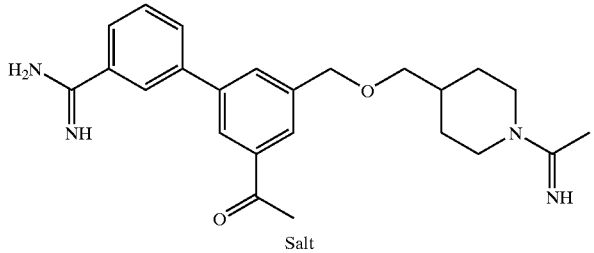 | ¹H-NMR(270MHz, DMSO-d₆+D₂O)δ 1.1~1.4(m, 2H), 1.7~2.1(m, 3H), 2.28(s, 3H), 2.67(s, 3H), 3.0~3.5(m,4H), 3.8~4.0(m, 1H), 4.0~4.2(m, 1H), 4.64(s, 2H), 7.74(t, 1H, J=7.8Hz), 7.87(d, 1H, J=7.6Hz), 8.00(s, 1H), 8.03(s, 1H), 8.07(d, 1H, J=7.6Hz), 8.16(s, 1H), 8.28(s, 1H). |
| 56 | 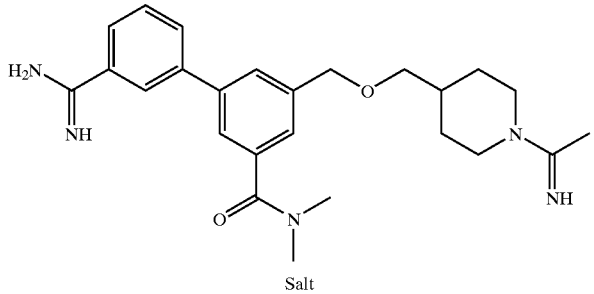 | ¹H-NMR(270MHz, DMSO-d₆+D₂O)δ 1.1~1.4(m, 2H), 1.7~2.1(m, 3H), 2.28(s, 3H), 2.95(s, 3H), 3.01(s, 3H), 3.0~3.5(m,4H), 3.8~4.0(m, 1H), 4.0~4.2(m, 1H), 4.63(s, 2H), 7.74(t, 1H, J=7.8Hz), 7.87(d, 1H, J=7.6Hz), 8.00(s, 1H), 8.03(s, 1H), 8.07(d, 1H, J=7.7Hz), 8.15(s, 1H), 8.30(s, 1H). |
| 57 | 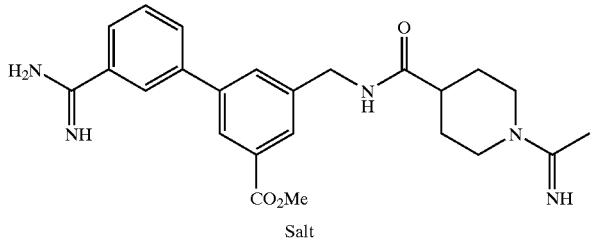 | MS 436[M+H] |

TABLE 3-continued

| Example | Structure | Structural data |
|---|---|---|
| 58 | Salt | $^1$H-NMR(270MHz, DMSO-$d_6$+$D_2$O)δ 1.52(t, 3H, J=7.6Hz), 1.6~1.8(brs, 2H), 1.9~2.1(brs, 2H), 2.61(q, 2H, J=7.6Hz), 3.3~3.8(m, 5H), 3.92(s, 3H), 4.72(s, 2H), 7.6~8.3(m, 7H). |
| 59 | Salt | MS 480[M+H] |
| 60 | Salt | MS 438[M+H] |
| 61 | Hydrochloride | $^1$H-NMR(270MHz, DMSO-$d_6$)δ 1.2~1.6(m, 2H), 1.9~2.2(m, 3H), 2.31(s, 3H), 3.0~3.4(m, 2H), 3.47(d, 2H, J=5.9Hz), 3.9~4.1(m, 2H), 4.65(s, 2H), 7.6~7.8(m, 3H), 8.0~8.1(m, 2H), 8.10(s, 1H), 8.24(s, 1H). |
| 62 | Hydrochloride | $^1$H-NMR(270MHz, DMSO-$d_6$)δ 1.3~1.5(m, 2H), 1.7~2.0(m, 3H), 2.85(t, 2H, J=11.5Hz), 3.2~3.4(m, 4H), 4.62(s, 2H), 7.74(t, 1H, J=7.8Hz), 7.85(d, 1H, J=7.9Hz), 7.9~8.0(m, 2H), 8.06(d, 1H, J=7.9Hz), 8.14(s, 1H), 8.27(s, 1H), 9.45(brs, 3H). |
| 63 | 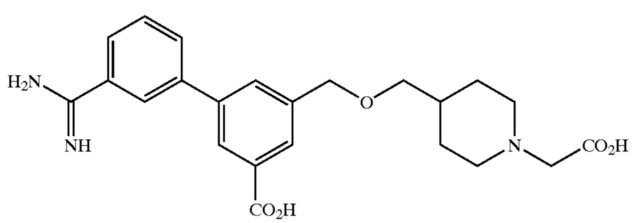 | $^1$H-NMR(270MHz, DMSO-$d_6$+$D_2$O)δ 1.4–1.6(m, 2H), 1.83(brd, J=12Hz, 3H), 2.86(t, J=12Hz, 2H), 3.3–3.5(m, 6H), 4.59(s, 2H), 7.6~8.1(m, 6H), 8.21(s, 1H). |

TABLE 3-continued

| Example | Structure | Structural data |
|---|---|---|
| 64 | 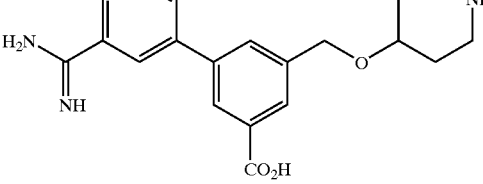 Hydrochloride | $^1$H-NMR(270MHz, DMSO-$d_6$)δ 1.8~2.2(m, 4H), 2.9~3.3(m, 4H), 3.6~3.8(m, 1H), 4.65(s, 2H), 7.4~7.5(brs, 1H), 7.6~8.5(m, 7H), 8.8~9.0(brs, 1H), 9.1~9.3(brs, 2H), 9.6~9.7(brs, 2H). |
| 65 | 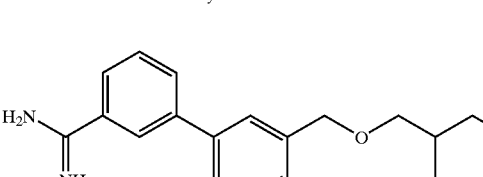 Hydrochloride | $^1$H-NMR(270MHz, DMSO-$d_6$)δ 1.18(d, 6H, J=6.6Hz), 1.4~1.65(m, 2H), 1.75~1.95(m, 3H), 2.6~2.9(m, 2H), 3.1~3.5(m, 5H), 4.33(m, 2H), 4.62(s, 2H), 7.73(t, 1H, J=7.9Hz). 7.84(d, 1H, J=7.6Hz), 7.94(s, 1H), 7.97(s, 1H), 8.06(d, 1H, J=7.6Hz), 8.13(s, 1H), 8.27(s, 1H), 9.45(brs, 3H). |
| 66 | 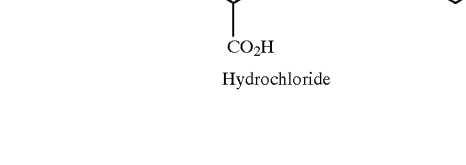 Hydrochloride | $^1$H-NMR(270MHz, DMSO-$d_6$)δ 1.6~1.8(m, brs, 2H), ~1.9~2.1(brs, 2H), 2.28(s, 3H), 3.2~3.5(m, 2H), 3.6~3.9(m, 3H), 4.70(s, 2H), 7.6~8.4(m, 7H). |
| 67 | 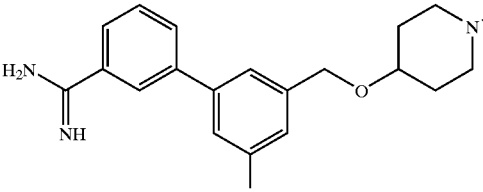 Hydrochloride | $^1$H-NMR(270HMz, DMSO-$d_6$)δ 1.16(t, 3H, J=7.6Hz), 2.53(q, 2H, J=7.6Hz), 3.2~4.0(m, 5H), 4.69(s, 2H), 7.6~8.3(m, 7H). |
| 68 | 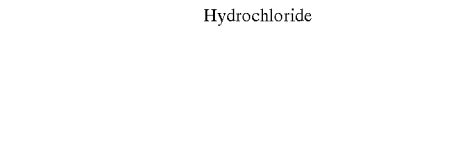 Hydrochloride | $^1$H-NMR(270HMz, DMSO-$d_6$+$D_2$O)δ 1.3–1.5(m, 2H), 1.96(d, J=14Hz, 2H), 2.11(brs, 1H), 2.7–3.0(m, 4H), 4.30(s, 2H), 7.74(t, J=7.7Hz, 1H), 7.87(d, J=7.7Hz, 1H), 8.1–8.5(m, 5H). |

TABLE 3-continued

| Example | Structure | Structural data |
|---|---|---|
| 69 | (structure) Salt | MS 424[M+H] |
| 70 | (structure) Hydrochloride | $^1$H-NMR(270MHz, DMSO-d$_6$+D$_2$O)δ 1.2–1.5(m, 2H) 1.9~2.0(m, 2H), 2.28(s, 3H), 2.1~2.3(m, 1H), 2.9~3.4(m, 4H), 4.02(dd, J=13.5, 53Hz, 2H), 4.34(s, 2H), 7.7~8.0(m, 2H), 8.1~8.3(m, 3H), 8.41(s, 1H), 8.47(s, 1H). |
| 71 | (structure) Salt | MS 465[M+H] |
| 72 | (structure) Hydrochloride | $^1$H-NMR(270MHz, DMSO-d$_6$+D$_2$O)δ 1.4–2.3(m, 5H), 2.9–3.9(m, 10H), 4.33(s, 2H), 7.80(t, J=7.6Hz, 1H), 7.89(d, J=7.6Hz, 1H), 8.1–8.3(m, 4H), 8.41(s, 1H). |
| 73 | (structure) Hydrochloride | $^1$H-NMR(270MHz, DMSO-d$_6$)δ 0.8~2.0(m, 11H), 2.81(d, 2H, J=5.9Hz), 4.29(s, 2H), 7.7–8.5(m, 7H), 9.1~9.7(m, 3H). |

TABLE 3-continued

| Example | Structure | Structural data |
|---|---|---|
| 74 | 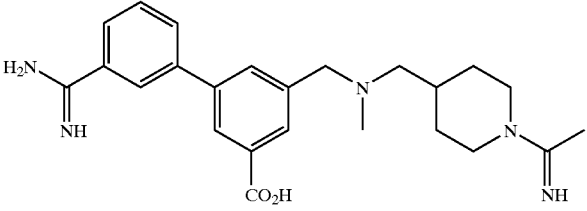 Hydrochloride | ¹H-NMR(270MHz, DMSO-d₆)δ 1.1~1.4(m, 2H), 1.8~2.3(m, 3H), 2.25(s, 6H), 3.0~4.3(m, 8H), 7.7~8.6(m, 7H), 9.16 & 9.51(brs, 3H). |
| 75 | 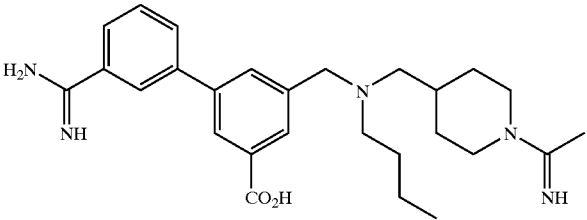 Hydrochloride | ¹H-NMR(270MHz, DMSO-d₆)δ 0.83(t, 3H, J=5.7Hz), 1.0~1.6(m, 6H), 1.8~2.0(m,H), 2.24(s, 3H), 2.3~2.5(m, 4H), 3.0~3.5(m, 4H), 3.68(s, 2H), 3.9~4.1(brs, 1H), 7.5~8.5(m, 7H). |
| 76 | 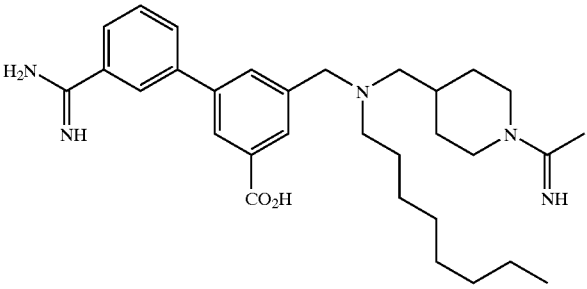 Hydrochloride | ¹H-NMR(270MHz, DMSO-d₆)δ 0.85(brs, 3H), 1.0–2.0(m, 15H), 2.23(s, 3H), 2.3–2.6(m, 2H), 2.7–3.3(m, 4H), 3.8–4.2(m, 2H), 4.67(brs, 2H), 7.74(dd, 7.9, 7.9Hz, 1H), 7.88(d, 7.8Hz, 1H), 7.9–8.3(m, 3H), 8.46(brs, 1H), 8.56(brs, 1H). |
| 77 | 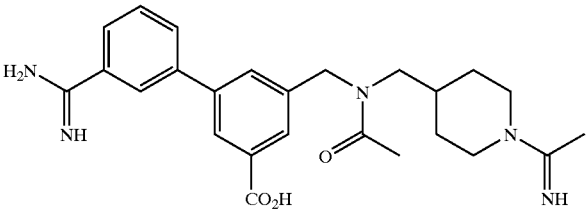 Hydrochloride | ¹H-NMR(270MHz, DMSO-d₆)δ 1.1~1.5(m, 2H), 1.7~1.9(m, 2H), 2.0~2.3(m, 1H), 2.08 & 2.14(s, 3H), 2.27(s, 3H), 3.0~4.3(m, 6H), 4.66 & 4.73(s, 2H), 7.7~8.5(m, 7H), 9.28(brs, 3H). |
| 78 | 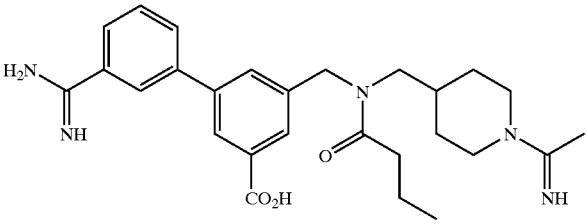 Hydrochloride | ¹H-NMR(270MHz, DMSO-d₆)δ 0.92 & 0.97(t, 3H, J=7.3Hz), 1.2~1.5(m, 2H), 1.5~2.0(m, 4H), 2.0~2.2(m, 2H), 2.30(s, 3H), 2.4~2.5(m, 2H), 3.0~3.5(m, 4H), 4.00(brs, 1H), 4.67(s, 2H), 7.0~8.3(m, 7H). |

TABLE 3-continued

| Example | Structure | Structural data |
|---|---|---|
| 79 | 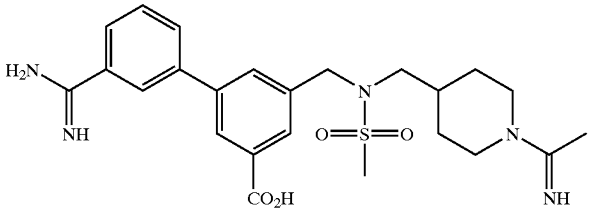 | $^1$H-NMR(270MHz, DMSO-$d_6$)δ 1.1~1.3(m, 2H), 1.7~2.0(m, 3H), 2.21(s, 3H), 2.8~3.5(m, 6H), 3.00(s, 3H), 4.49(s, 2H), 7.7~7.9(m, 2H), 7.86(s, 1H), 8.04(s, 1H), 8.0~8.1(m, 1H), 8.22(s, 1H), 8.46(s, 1H), 9.21(m, 3H). |
| 80 | 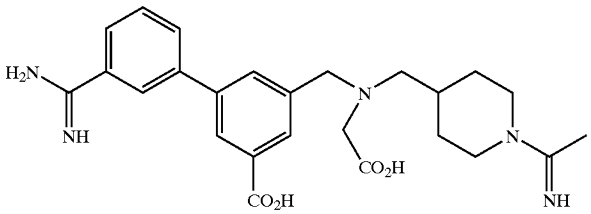 | $^1$H-NMR(270MHz, DMSO-$d_6$)δ 1.1~1.3(m, 2H), 1.8~1.9(m, 3H), 2.25(s, 3H), 2.5~2.9(m, 4H), 3.2~3.4(m, 4H), 3.38(brs, 1H), 4.09(brs, 1H), 7.75(t, 1H), 7.89(d, 1H), 8.08(brs, 2H), 8.32(brs, 2H), 8.67(brs, 1H), 9.23(s, 1H), 9.39(s, 1H), 9.58(s, 2H). |
| 81 | 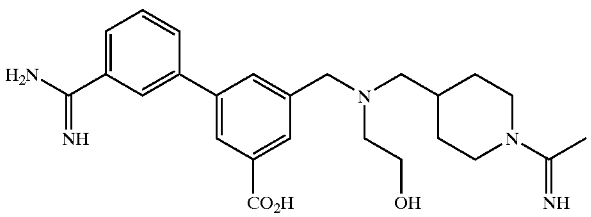 | $^1$H-NMR(270MHz, DMSO-$d_6$)δ 1.0~1.3(m, 2H), 1.5~2.0(m, 3H), 2.24(s, 3H), 2.30(d, 2H, J=6.5Hz), 2.4~2.6(m, 2H), 3.13(brd, 2H, J=12.4Hz), 3.50(t, 2H, J=5.9Hz), 3.73(s, 2H), 7.5~8.4(m, 7H). |
| 82 | 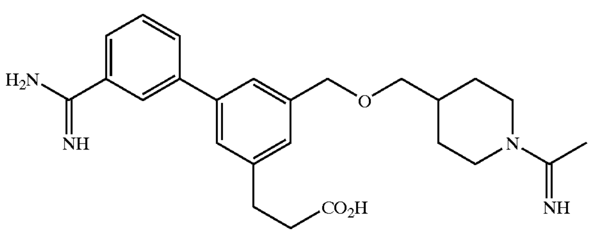 | $^1$H-NMR(270MHz, DMSO-$d_6$)δ 1.21~1.43(m, 2H), 1.78~1.90(m, 2H), 1.90~2.08(m, 1H), 2.25(S, 3H), 2.45~2.55(m, 5H), 2.88~2.98(m, 2H), 3.5(brs, 6H), 4.0(m, 1H), 4.55(s, 2H), 7.25(s, 1H), 7.50(s, 1H), 7.61(s, 1H) 7.60~7.78(m, 2H), 7.92(m, 2H), 8.3(s, 1H). |
| 83 | 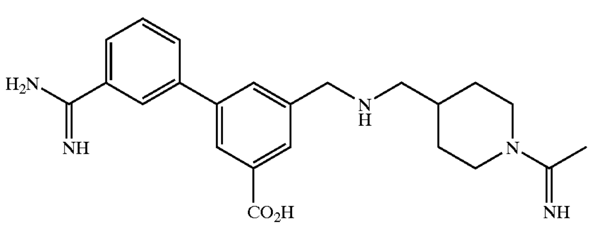 | MS 424[M+H] |

TABLE 4

| | Fxa inhibition activity IC$_{50}$ ($\mu$M) | Thrombin inhibition activity IC$_{50}$ ($\mu$M) | APTT CT2 ($\mu$M) | AChE inhibition activity IC$_{50}$ ($\mu$M) | Mouse BA (%) |
|---|---|---|---|---|---|
| Compound of Example 61 | 0.063 | >1000 | 0.76 | 49 | 10 |
| Compound of Example 70 | 0.19 | >1000 | 2.0 | 140 | 11 |
| Compound of Example 72 | 1.2 | >1000 | 11 | >250 | 13 |
| Compound of Example 73 | 1.7 | >1000 | 13 | >250 | ND |
| Compound of Example 74 | 0.59 | >1000 | 5.4 | 150 | 13 |
| Compound of Example 81 | 0.21 | 820 | 2.8 | 130 | 7 |
| Compound of Example 82 | 0.13 | >1000 | 1.9 | 170 | 11 |
| Compound of Example 83 | 0.16 | >1000 | 1.9 | 760 | 12 |

What is claimed is:

1. A biphenylamidine derivative of general formula (1):

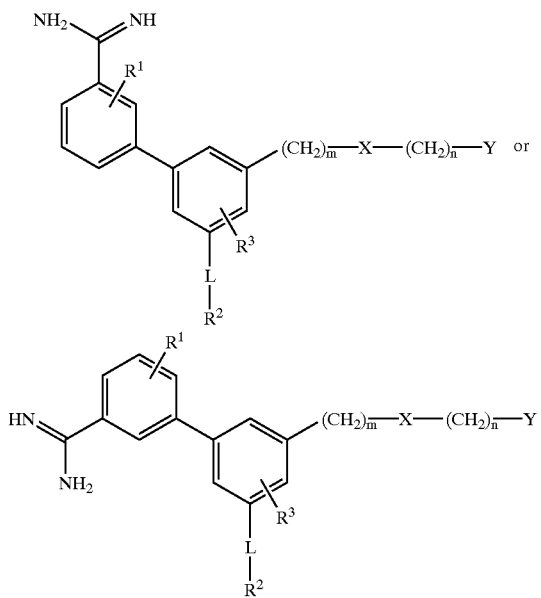

(1)

wherein
R$^1$ is a hydrogen atom, a fluorine atom, a chlorine atom, a bromine atom, a hydroxyl group, an amino group, a nitro group, a C$_{1-8}$ alkyl group, or a C$_{1-8}$ alkoxy group;
L is a direct bond or a C$_{1-4}$ alkylene group;
R$^2$ is a fluorine atom; a chlorine atom; a bromine atom; a hydroxyl group; an amino group; a C$_{1-8}$ alkoxy group; a carboxyl group; a C$_{1-8}$ alkoxycarbonyl group; an aryloxycarbonyl group; an aralkoxycarbonyl group; a carbamoyl group wherein a nitrogen atom constituting the carbamoyl group may be substituted with a mono- or di-C$_{1-8}$ alkyl group or may be a nitrogen atom in an amino acid; a C$_{1-8}$ alkylcarbonyl group; a C$_{1-8}$ alkylsulfenyl group; a C$_{1-8}$ alkylsulfinyl group; a C$_{1-8}$ alkylsulfonyl group; a mono- or di-C$_{1-8}$ alkylamino group; a mono- or di-C$_{1-8}$ alkylaminosulfonyl group; a sulfo group; a phosphono group; a bis(hydroxycarbonyl) methyl group; a bis(alkoxycarbonyl)methyl group; or a 5-tetrazolyl group;
R$^3$ is a hydrogen atom, a fluorine atom, a chlorine atom, a bromine atom, a hydroxyl group, an amino group, a nitro group, a C$_{1-8}$ alkyl group, a C$_{1-8}$ alkoxy group, a carboxyl group, or a C$_{1-8}$ alkoxycarbonyl group;
X is any of the formulae:

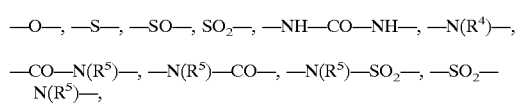

wherein
R$^4$ is a hydrogen atom, a C$_{1-10}$ alkyl group, a C$_{1-10}$ alkylcarbonyl group, a C$_{1-10}$ alkylsulfonyl group, a C$_{3-8}$ cycloalkyl group, or an aryl group,
R$^5$ is a hydrogen atom, a C$_{1-10}$ alkyl group, a C$_{3-8}$ cycloalkyl group, or an aryl group,
wherein an alkyl group in the R$^4$ and R$^5$ may be substituted with an aryl group, a hydroxyl group, an amino group, a fluorine atom, a chlorine atom, a bromine atom, a C$_{1-8}$ alkoxy group, a carboxyl group, a C$_{1-8}$ alkoxycarbonyl group, an aryloxycarbonyl group, an aralkoxycarbonyl group, a carbamoyl group, or a 5-tetrazolyl group;
Y is a C$_{4-8}$ cycloalkyl group wherein a methylene group in the C$_{4-8}$ cycloalkyl may be replaced with a carbonyl group, or may be substituted with a fluorine atom, a chlorine atom, a bromine atom, a hydroxyl group, an amino group, a C$_{1-8}$ alkyl group, a C$_{1-8}$ alkoxy group, a carbamoyl group, a C$_{1-8}$ alkoxycarbonyl group, a carboxyl group, an aminoalkyl group, a mono- or di-alkylamino group, or a mono- or di-alkylaminoalkyl group; or the following 5-8-membered ring of the formulae I-1 or I-2:

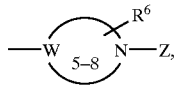

[I-1]

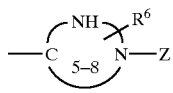

[I-2]

wherein, in the formulae I-1 and I-2,
in each cyclic system, the methylene group may be replaced with a carbonyl group, and the cycle may have unsaturated bonds,
R$^6$ is a hydrogen atom, a fluorine atom, a chlorine atom, a bromine atom, a hydroxyl group, an amino group, a nitro group, a C$_{1-8}$ alkyl group, or a C$_{1-8}$ alkoxy group,
W is C—H, or a nitrogen atom, with the proviso that W is not a nitrogen atom when the cycle is a 5-membered ring,
Z is a hydrogen atom; a C$_{1-10}$ alkyl group wherein the alkyl group may be substituted with a hydroxyl group except when Z is a C$_1$ alkyl group, an amino group, a C$_{1-8}$ alkoxy group except when Z is a C$_1$ alkyl group, a carboxyl group, a C$_{1-8}$ alkoxycarbonyl group, an aryloxycarbonyl group or an aralkoxycarbonyl group; a C$_{1-8}$ alkylcarbonyl group; an arylcarbonyl group; an aralkylcarbonyl group; an amidino group; or the following group of the formula I-3:

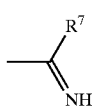
[I-3]

wherein, in the formula I-3,
R$^7$ is a C$_{1-8}$ alkyl group wherein the alkyl group may be substituted with a hydroxyl atom or a C$_{1-8}$ alkoxy group; an aralkyl group; or an aryl group;
m is an integer of 1–3;
n is an integer of 0–3, with the proviso that W is not a nitrogen atom when n is 0–1;
or a pharmaceutically acceptable salt thereof.

2. A biphenylamidine derivative according to claim 1 wherein, in said formula (1),
R$^1$ is a hydrogen atom, a fluorine atom, a chlorine atom, a bromine atom, a hydroxyl group, an amino group, a C$_{1-4}$ alkyl group, or a C$_{1-4}$ alkoxy group;
L is a direct bond or a C$_{1-4}$ alkylene group;
R$^2$ is a fluorine atom; a chlorine atom; a bromine atom; a hydroxyl group; an amino group; a C$_{1-8}$ alkoxy group; a carboxyl group; a C$_{1-8}$ alkoxycarbonyl group; an aryloxycarbonyl group; an aralkoxycarbonyl group; a carbamoyl group wherein a nitrogen atom in the carbamoyl group may be substituted with a mono- or di-C$_{1-8}$ alkyl group or may be a nitrogen atom in an amino acid; a C$_{1-8}$ alkylcarbonyl group; a C$_{1-8}$ alkylsulfenyl group; a C$_{1-8}$ alkylsulfinyl group; a C$_{1-8}$ alkylsulfonyl group; a mono- or di-C$_{1-8}$ alkylamino group; a mono- or di-C$_{1-8}$ alkylaminosulfonyl group; a sulfo group; a phosphono group; a bis(hydroxycarbonyl)methyl group; a bis(alkoxycarbonyl)methyl group; or a 5-tetrazolyl group;
R$^3$ is a hydrogen atom;
X is any of the formulae:

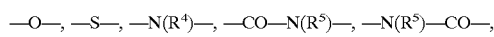

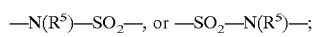

wherein
R$^4$ is a hydrogen atom, a C$_{1-10}$ alkyl group, a C$_{1-10}$ alkylcarbonyl group, or a C$_{1-10}$ alkylsulfonyl group,
R$^5$ is a hydrogen atom, or a C$_{1-10}$ alkyl group, wherein an alkyl group in the R$^4$ and R$^5$ may be substituted with an aryl group, a hydroxyl group, an amino group, a fluorine atom, a chlorine atom, a bromine atom, a C$_{1-8}$ alkoxy group, a carboxyl group, a C$_{1-8}$ alkoxycarbonyl group, an aryloxycarbonyl group, an aralkoxycarbonyl group, a carbamoyl group, or a 5-tetrazoyl group;
Y is a C$_{4-8}$ cycloalkyl group wherein a methylene group constituting the C$_{4-8}$ cycloalkyl group may be replaced with a carbonyl group, or may be substituted with a fluorine atom, a chlorine atom, a bromine atom, a hydroxyl group, an amino group, a C$_{1-8}$ alkyl group, a C$_{1-8}$ alkoxy group, a carbamoyl group, a C$_{1-8}$ alkoxycarbonyl group, a carboxyl group, an aminoalkyl group, a mono- or di-alkylamino group, or a mono- or di-alkylaminoalkyl group; or the following 5-8-membered ring of the formula II-1:

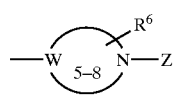
[II-1]

wherein, in formula II-1,
in the cyclic system, the methylene group may be replaced with a carbonyl group,
R$^6$ is a hydrogen atom, a fluorine atom, a chlorine atom, a bromine atom, a hydroxyl group, an amino group, a C$_{1-4}$ alkyl group, or a C$_{1-4}$ alkoxy group;
W is C—H, or a nitrogen atom, with the proviso that W is not a nitrogen group when the cycle is a 5-membered ring,
Z is a hydrogen atom; a C$_{1-10}$ alkyl group wherein the alkyl group may be substituted with a hydroxyl group except when Z is a C$_1$ alkyl group, an amino group, a C$_{1-8}$ alkoxy group except when Z is a C$_1$ alkyl group, a carboxyl group, a C$_{1-8}$ alkoxycarbonyl group, an aryloxycarbonyl group, or an aralkoxycarbonyl group; a C$_{1-8}$ alkylcarbonyl group; an arylcarbonyl group; an aralkylcarbonyl group; an amidino group; or the following group of the formula II-2:

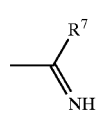
[II-2]

wherein, in formula II-2,
R$^7$ is a C$_{1-8}$ alkyl group wherein the alkyl group may be substituted with a hydroxyl group or a C$_{1-4}$ alkoxy group; an aralkyl group; or an aryl group;
m is an integer of 1–3;
n is an integer of 0–3, with the proviso that W is not a nitrogen atom when n is 0–1;
or a pharmaceutically acceptable salt thereof.

3. A biphenylamidine derivative according to claim 1 or 2, of general formula (2):

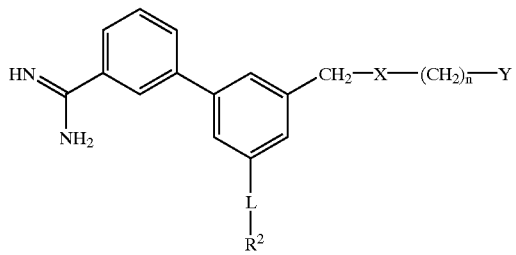
(2)

wherein
L is a bond or a C$_{1-4}$ alkylene group;
R$^2$ is a carboxyl group; a C$_{1-4}$ alkoxycarbonyl group; an aralkoxycarbonyl group; a carbamoyl group wherein a nitrogen atom constituting the carbamoyl group may be substituted with a mono- or di-C$_{1-4}$ alkyl group or may be a nitrogen atom in an amino acid; or a C$_{1-4}$ alkylcarbonyl group;
X is —O—, —N(R$^4$)—, or —NH—CO—,
wherein
R$^4$ is a hydrogen atom, a C$_{1-10}$ alkyl group, a C$_{1-10}$ alkylcarbonyl group or a C$_{1-10}$ alkylsulfonyl group, the alkyl being optionally substituted with a hydroxyl group, an amino group, a fluorine atom, a carboxyl group or a $C_{1-8}$ alkoxycarbonyl group;

Y is a $C_{5-6}$ cycloalkyl group wherein a methylene group constituting the $C_{5-6}$ cycloalkyl group may be substituted with a carbamonyl group, a $C_{1-4}$ alkoxy group or a carboxyl group; or the following 5-6-membered ring of the formula III-1:

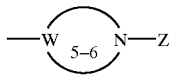
[III-1]

wherein, in formula III-1:

W is C—H, or a nitrogen atom, with the proviso that W is not a nitrogen atom when the cycle is a 5-membered ring, Z is a hydrogen atom; a $C_{1-4}$ alkyl group wherein the alkyl group may be substituted with a hydroxyl group except when Z is a $C_1$ alkyl group, an amino group, a carboxyl group or a $C_{1-4}$ alkoxycarbonyl group; a $C_{1-4}$ alkylcarbonyl group; an amidino group; or the following group of the formula III-2:

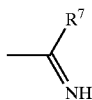
[III-2]

wherein, in formula III-2, $R^7$ is a $C_{1-4}$ alkyl group wherein the alkyl group may be substituted with a hydroxyl group;

n is an integer of 0–2; with the proviso that W is not a nitrogen group when n is 0–1;

or a pharmaceutically acceptable salt thereof.

4. A biphenylamidine derivative according to claim 3, wherein, in said formula (2), X is —O—, or —N($R^4$)—, wherein $R^4$ is a hydrogen atom, a $C_{1-10}$ alkyl group, a $C_{1-10}$ alkylcarbonyl group or a $C_{1-10}$ alkylsulfonyl group, the alkyl group being optionally substituted with a hydroxyl group, an amino group, a fluorine atom, a carboxyl group or a $C_{1-8}$ alkokycarbonyl group;

or a pharmaceutically acceptable salt thereof.

5. A biphenylamidine derivative according to claim 3, wherein, in said formula (2), X is —NH—CO—, or a pharmaceutically acceptable salt thereof.

6. A biphenylamidine derivative according to claim 3, wherein, in general formula (2), L is a bond;

$R^2$ is a carboxyl group or a methoxycarbonyl group;

X is —O—, or —N($R^4$)—, wherein $R^4$ is a hydrogen atom, a methyl group or a 2-hydroxyethyl group;

Y is any of the formulae:

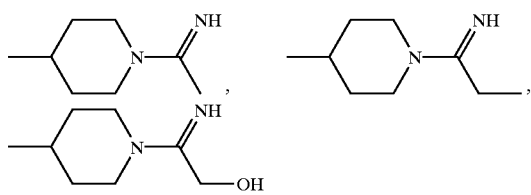

n is 1;

or a pharmaceutically acceptable salt thereof.

7. A method of inhibiting blood coagulation, comprising administering to a subject in need thereof at least a biphenylamidine derivative or a pharmaceutically acceptable salt thereof according to claim 1 or 2.

8. A method of preventing thrombosis or embolus, comprising administering to a subject in need thereof at least a biphenylamidine derivative or a pharmaceutically acceptable salt thereof according to claim 1 or 2.

9. A method of treating thrombosis or embolus, comprising administering to a subject in need thereof at least a biphenylamidine derivative or a pharmaceutically acceptable salt thereof according to claim 1 or 2.

* * * * *